(12) United States Patent
Bassarab et al.

(10) Patent No.: US 7,727,962 B2
(45) Date of Patent: *Jun. 1, 2010

(54) POWDER COMPRISING NEW COMPOSITIONS OF OLIGOSACCHARIDES AND METHODS FOR THEIR PREPARATION

(75) Inventors: Stefan Bassarab, Biberach (DE); Karoline Bechtold-Peters, Biberach (DE); Richard Fuhrherr, Nuremberg (DE); Wolfgang Friess, Iffeldorf (DE); Patrick Garidel, Norderstedt (DE); Torsten Schultz-Fademrecht, Biberach (DE)

(73) Assignee: Boehringer Ingelheim Pharma GmbH & Co. KG, Ingelheim am Rhein (DE)

( * ) Notice: Subject to any disclaimer, the term of this patent is extended or adjusted under 35 U.S.C. 154(b) by 719 days.

This patent is subject to a terminal disclaimer.

(21) Appl. No.: 11/119,957

(22) Filed: May 2, 2005

(65) Prior Publication Data

US 2005/0250704 A1 Nov. 10, 2005

Related U.S. Application Data

(60) Provisional application No. 60/572,306, filed on May 18, 2004.

(30) Foreign Application Priority Data

May 10, 2004 (DE) .................. 10 2004 022 928

(51) Int. Cl.
A61K 31/715 (2006.01)
A61K 38/05 (2006.01)
A61K 38/04 (2006.01)

(52) U.S. Cl. .................... 514/18; 514/19; 514/61
(58) Field of Classification Search .......... 514/18, 514/19, 61
See application file for complete search history.

(56) References Cited

U.S. PATENT DOCUMENTS

| | | | |
|---|---|---|---|
| 3,634,582 A | 1/1972 | Hartley et al. | |
| 3,894,146 A | 7/1975 | Tsuyama | |
| 3,906,950 A | 9/1975 | Cocozza | |
| 4,013,075 A | 3/1977 | Cocozza | |
| 4,570,630 A | 2/1986 | Elliott et al. | |
| 4,811,731 A | 3/1989 | Newell et al. | |
| 5,035,237 A | 7/1991 | Newall et al. | |
| 5,296,473 A | 3/1994 | Hara et al. | |
| 5,320,094 A | 6/1994 | Laube et al. | |
| 5,458,135 A | 10/1995 | Patton et al. | |
| 5,489,577 A | 2/1996 | Ikeda et al. | |
| 5,505,945 A | 4/1996 | Gristina et al. | |
| 5,522,385 A | 6/1996 | Lloyd et al. | |
| 5,626,874 A | 5/1997 | Conte et al. | |
| 5,672,581 A | 9/1997 | Rubsamen et al. | |
| 5,753,469 A * | 5/1998 | Nakada et al. .......... 435/99 | |
| 5,785,049 A | 7/1998 | Smith et al. | |
| 5,922,324 A | 7/1999 | Aga et al. | |
| 5,947,118 A | 9/1999 | Hochrainer et al. | |
| 5,972,388 A | 10/1999 | Sakon et al. | |
| 6,453,795 B1 | 9/2002 | Eicher et al. | |
| 2003/0059511 A1 | 3/2003 | Ishii | |
| 2005/0250705 A1 | 11/2005 | Bassarab et al. | |
| 2005/0255119 A1 | 11/2005 | Bassarab et al. | |
| 2006/0008574 A1 | 1/2006 | Begli et al. | |

FOREIGN PATENT DOCUMENTS

| | | |
|---|---|---|
| CA | 2273241 | 7/1998 |
| CA | 2273277 | 7/1998 |
| CA | 2297174 A1 | 2/1999 |
| CA | 2565019 A1 | 12/2005 |
| DE | 1792207 | 11/1971 |
| DE | 3625685 A1 | 3/1987 |
| DE | 19732351 | 2/1999 |
| DE | 19953727 A1 | 5/2001 |
| EP | 129985 A1 | 1/1985 |
| EP | 237507 A1 | 9/1987 |
| EP | 467172 A1 | 1/1992 |
| EP | 00630651 A2 | 12/1994 |
| EP | 0739986 | 10/1996 |

(Continued)

OTHER PUBLICATIONS

G. Xie, et al., "The thermodynamic mechanism of protein stabilization by trehalose". Biophysical Chemistry, vol. 64, No. 1, 1997, pp. 25-43.

G. Xie, et al., "Mechanism of the stabilization of ribonuclease A by sorbitol: Preferential hydration is greater for the denatured than for the native protein". Protein Science, vol. 6, 1997, pp. 211-221.

S. N. Timasheff. "The control of protein stability and association by weak interactions with water: How do solvents affect these processes?". Annual Rev. Biophysics and Biomolecular Structure, vol. 22, 1993, pp. 67-97.

A. M. Boctor, et al., "Enhancement of the stability of thrombin by polyols: microcalorimetric studies". Journal of Pharmacy and Pharmacology, vol. 44, No. 7, 1992, pp. 600-603.

(Continued)

*Primary Examiner*—Shaojia Anna Jiang
*Assistant Examiner*—Ganapathy Krishnan
(74) *Attorney, Agent, or Firm*—Michael P. Morris; Mary-Ellen M. Devlin; Anthony P. Bottino

(57) ABSTRACT

The present invention concerns powders containing a pharmaceutical active substance and a combination of excipients comprising at least one 1,4 O-linked saccharose derivative selected from the compounds: 1,4 O-linked D-Gal-saccharose (lactosucrose), 1,4 O-linked D-Glu-saccharose (glucosyl sucrose), or 1,4 O-linked Glu-Glu-saccharose (maltosyl sucrose) in combination with at least one further excipient. The other excipient is preferably an amino acid, a peptide and/or a mono-, di- and/or oligosaccharide, wherein the oligosaccharide may be a second 1,4 O-linked saccharose derivative, provided that this is different from the first.

45 Claims, 14 Drawing Sheets

FOREIGN PATENT DOCUMENTS

| EP | 0745382 A1 | 12/1996 |
|---|---|---|
| EP | 0911037 A1 | 4/1999 |
| EP | 0974358 A2 | 1/2000 |
| EP | 1174148 A1 | 1/2002 |
| EP | 1223175 A1 | 7/2002 |
| WO | 11297 A1 | 11/1989 |
| WO | 13328 A1 | 11/1990 |
| WO | 14468 A1 | 10/1991 |
| WO | 07607 A1 | 4/1994 |
| WO | 28958 A1 | 12/1994 |
| WO | 31479 A1 | 11/1995 |
| WO | 09814 A1 | 4/1996 |
| WO | 32096 A1 | 10/1996 |
| WO | 32149 A1 | 10/1996 |
| WO | 04801 A1 | 2/1997 |
| WO | 12683 | 4/1997 |
| WO | 12687 A1 | 4/1997 |
| WO | 20590 A1 | 6/1997 |
| WO | 41031 A1 | 11/1997 |
| WO | 41833 A1 | 11/1997 |
| WO | 44013 A1 | 11/1997 |
| WO | 16205 A2 | 4/1998 |
| WO | WO 98/16205  * | 4/1998 |
| WO | 31346 A1 | 7/1998 |
| WO | 07340 A1 | 2/1999 |
| WO | 99/27071 | 6/1999 |
| WO | 66903 A2 | 12/1999 |
| WO | 00/09164 | 2/2000 |
| WO | 10541 A1 | 3/2000 |
| WO | 13893 A2 | 3/2000 |
| WO | 00263 A2 | 1/2001 |
| WO | 32144 A1 | 10/2001 |
| WO | 43750 A2 | 6/2002 |
| WO | 03/041512 | 5/2003 |
| WO | 03/064473 | 8/2003 |
| WO | 03/080027 | 10/2003 |
| WO | 104473 A2 | 12/2003 |
| WO | 112996 A1 | 12/2005 |

OTHER PUBLICATIONS

B. S. Chang, et al., "Stablization of lyophilized porcine pancreatic elastase". Pharmaceutical Research, vol. 10, No. 10, 1993, pp. 1478-1483.

A. C. Herman, et al., "Characterization, formulation, and stability of neupogen (Filgrastim), a recombinant human granulocyte-colony stimulating factors". Pharmaceutical Biotechnology, vol. 9, 1996, pp. 303-328.

H.K. Chan, et al., "Effects of additives on heat denaturation of rhDNase in solutions". Pharmaceutical Research, vol. 13, No. 5, 1996, pp. 756-761.

J. Zhang, et al., "NMR study of the cold, heat, and pressure unfolding of ribonuclease A". Biochemistry, 1995, vol. 34, No. 27, pp. 8631-8641.

R. L. Remmele, Jr., et al., "Interleukin-1 receptor (IL-1R) liquid formulation development using differential scanning calorimetry". Pharmaceutical Research, vol. 15, No. 2, 1998, pp. 200-208.

Y. F. Maa, et al., "Effect of spray drying and subsequent processing conditions on residual moisture content and physical/biochemical stability of protein inhalation powders". Pharmaceutical Research, vol. 15, No. 5, 1998, pp. 768-775.

J. Broadhead, et al., "The effect of process and formulation variables on the properties of spray-dried b-galactosidase". Journal Pharm. Pharmacol, 1994, vol. 46, No. 6, pp. 458-467.

M. T. Vidgren, et al., "Comparison of physical and inhalation properties of spray-dried and mechanically micronized disodium cromoglycate". Int. J. Pharmaceutics, vol. 35, 1987, pp. 139-144.

R. W. Niven, et al., "Pulmonary delivery of powders and solutions containing recombinant human granulocyte colony-stimulating factor (rhG-CSF) to the rabbit". Pharmaceutical Research, vol. 11, No. 8, 1994, pp. 1101-1109.

Y. F. Maa, et al., "The effect of operating and formulation variables on the morphology of spray-dried protein particles". Pharmaceutical Development and Technology, vol. 2, No. 3, 1997, pp. 213-223.

H. R. Costantino, et al., "Effect of mannitol crystallization on the stability and aerosol performance of a spray-dried pharmaceutical protein, recombinant humanized anti-IgE monoclonal antibody". Journal of Pharmaceutical Sciences, Vo.87, No. 11, 1998, pp. 1406-1411.

C. Bosquillon, et al., "Influence of formation excipients and physical characteristics of inhalation dry powders on their aerosolization performance". Journal of Controlled Release, vol. 70, No. 3, 2001, pp. 329-339.

J. S. Huston, et al., "Protein engineering of antibody binding sites: recovery of specific activity in an anti-digoxin single-chain Fv analogue produced in *Escherichia Coli*". Proc. Natl. Acad. Sci., USA, vol. 85, 1988, pp. 5879 ff.

O. Perisic, et al., "Crystal structure of a diabody, a bivalent antibody fragment". Structure, vol. 2, 1994, pp. 1217 ff.

S. Z. Hu., et al., "Minibody: a novel engineered anti-carcinoembryonic antigen antibody fragment (single-chain Fv-CH3) which exhibits rapid, high-level targeting of xenografts". Cancer Research, vol. 56, 1996, pp. 3055 ff.

A. A. Kortt, et al., "Single-chain Fv fragments of anti-neuraminidase antibody NC10 containing five-and ten-residue linkers form dimmers and with zero-residue linker a trimer". Protein Engineering, vol. 10, No. 4, 1997, pp. 423 ff.

B. Lovejoy, et al. "Crystal structure of a synthetic triple-standard a-Helical bundle". Science, vol. 259, 1993, pp. 1288 ff.

P. Pack, et al., "Tetravalent miniantibodies with high avidity assembling in *Escherichia coli*". Journal Mo. Biol., 1995, 1995, 246, p. 28-34.

P. Pack, et al., "Improved bivalent miniantibodies, with identical avidy as whole antibodies, produced by high cell density fermentation of *Escherichia coli*". Bio/technology, vol. 11, 1993, pp. 1271 ff.

M. Adler, et al., "Stability and surface activity of lactate dehydrogenase in spray-dried trehalone". Journal of Pharmaceutical Sciences, vol. 88, No. 2, 1999, pp. 199-108.

S. N. Timasheff, et al., "Control of protein stability and reactions by weakly interacting cosolvents: the simplicity of the complicated". Advances in Protein Chemistry, vol. 51, p. 355, 1998.

ISR for PCT/EP2005/004807 dated May 5, 2005.

V. Windisch, et al. "Degradation Pathways of Salmon Calcitonin in Aqueous Solutions". Journal of Pharmaceutical Sciences, vol. 86, No. 3, Mar. 1997, pp. 359-364.

K. Masters. Spray Drying Handbook. 4$^{th}$ Edition, Longman Scientific & Technical. Copublished in the US with John Wiley & Sons, Inc., NY. Boehringer Ingelheim Vetmedica GmbH. pp. 1-696, Parts 1 through 5, 1985.

M. Willmann. Dissertation Stabilization of Pharmaceutical Protein Solutions by Vacuum Drying, pp. 14-23, 2003.

D. B. Dix, et al. "Increasing the Physical Stability of a Hydrophobic Protein: RHCNTF". Pharmaceutical Research (Supplement), 1995, BIOTEC 2074, 12, S-97.

S. M. Chamow, et al., Editors. "Antibody Fusion Proteins". Wiley-Liss Publication. Copyright 1999. pp. 1-316.

"Handbook of Pharmaceutical Excipients". American Pharmaceutical Association & The Pharmaceutical Society of Great Britain. 1986. pp. 153-162, 304-308, 231.

Alexander A. Kortt, et al., "Single-chain Fv fragments of anti-neuraminidase antibody NC10 containing five- and ten- residue linkers form dimers and with zero-residue linker a trimer" Protein Engineering, vol. 10, No. 4 pp. 423-433 (1997).

International Search Report for PCT/EP2005/004806 mailed Aug. 1, 2005.

International Search Report for PCT/EP2005/004808 mailed Jul. 17, 2006.

Bauer, et al. Basic Physical-Chemicals Principles for Dosage Forms, Edition 6, Chapter 4, pp. 70-73, 1999.

Bauer, et al. Basic Physical-Chemicals Principles for Dosage Forms, Edition 6, Chapter 2, pp. 103-107, 1999.

Bauer, et al. Basic Physical-Chemicals Principles for Dosage Forms, Edition 7, Chapter 6, pp. 167-191, 2002.

M. Adler. Dissertation, Spray Embedding of Proteins In Structure-Forming Agents: Stability and Surface Analysis, Chapter 2.3, Changes in Protein Structure, pp. 11-19, Jul. 23, 1999.

M. Adler. Dissertation, Spray Embedding of Proteins In Structure-Forming Agents: Stability and Surface Analysis, Chapter 4, Materials and Methods, pp. 41-56, Jul. 23, 1999.

M. Adler. Dissertation, Spray Embedding of Proteins In Structure-Forming Agents: Stability and Surface Analysis, Chapter 5.1, Sugars and Sugar Alcohols, pp. 58-70, Jul. 23, 1999.

M. Adler. Dissertation, Spray Embedding of Proteins In Structure-Forming Agents: Stability and Surface Analysis, Chapter 5.2, Amino Acids, pp. 71-83, Jul. 23, 1999.

M. Adler. Dissertation, Spray Embedding of Proteins In Structure-Forming Agents: Stability and Surface Analysis, Chapter 5.4, Spray Drying of Structure Forming Agents, pp. 84-102, Jul. 23, 1999.

M. Adler. Dissertation, Spray Embedding of Proteins In Structure-Forming Agents: Stability and Surface Analysis, Chapter 6.3, Influence of polysorbate 80 and Lipoid E80 On the Process and Storage Stability of LDH, pp. 111-123, Jul. 23, 1999.

M. Adler; Foreword, Spray Embedding of Proteins In Structure-Forming Agents: Stability and Surface Analysis, Table of Contents & Symbols indexing sections 4-9 listed above, Jul. 23, 1999.

* cited by examiner

Figure: 1
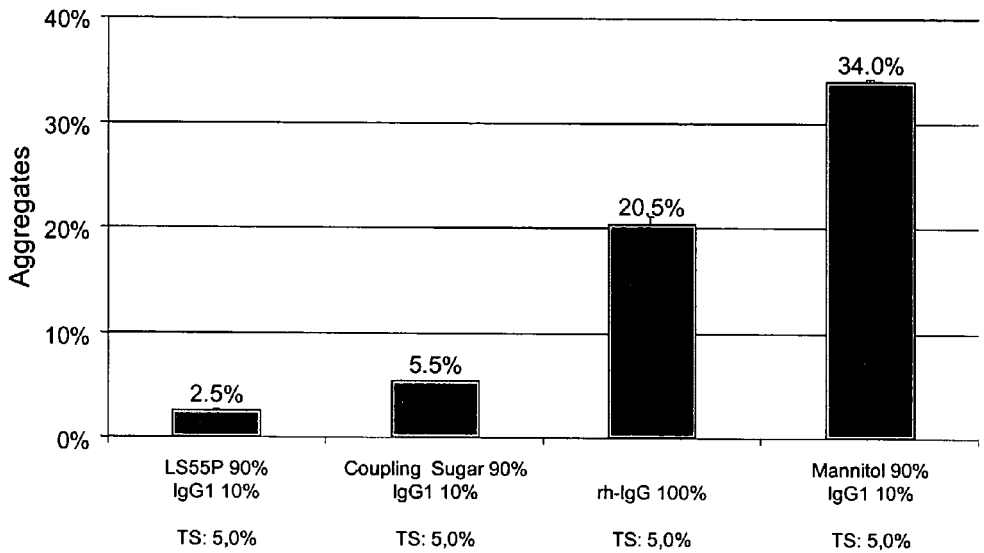
Figure: 2
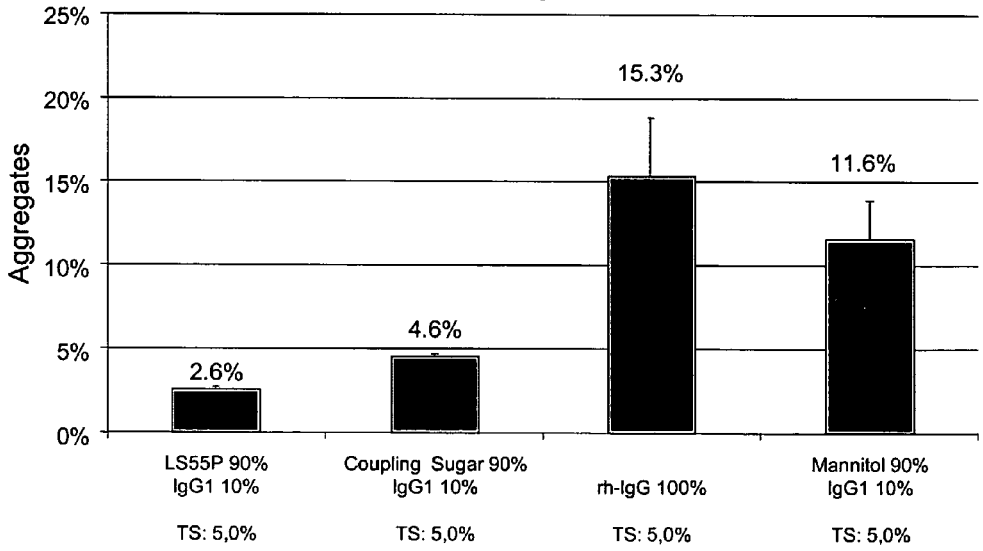

Figure: 3
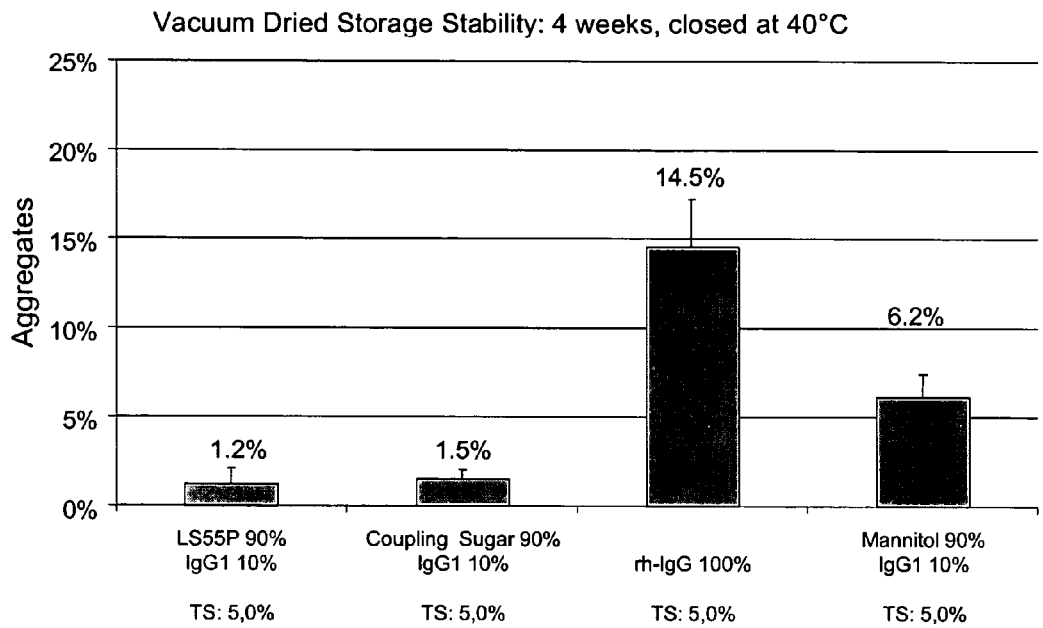
Figure: 4
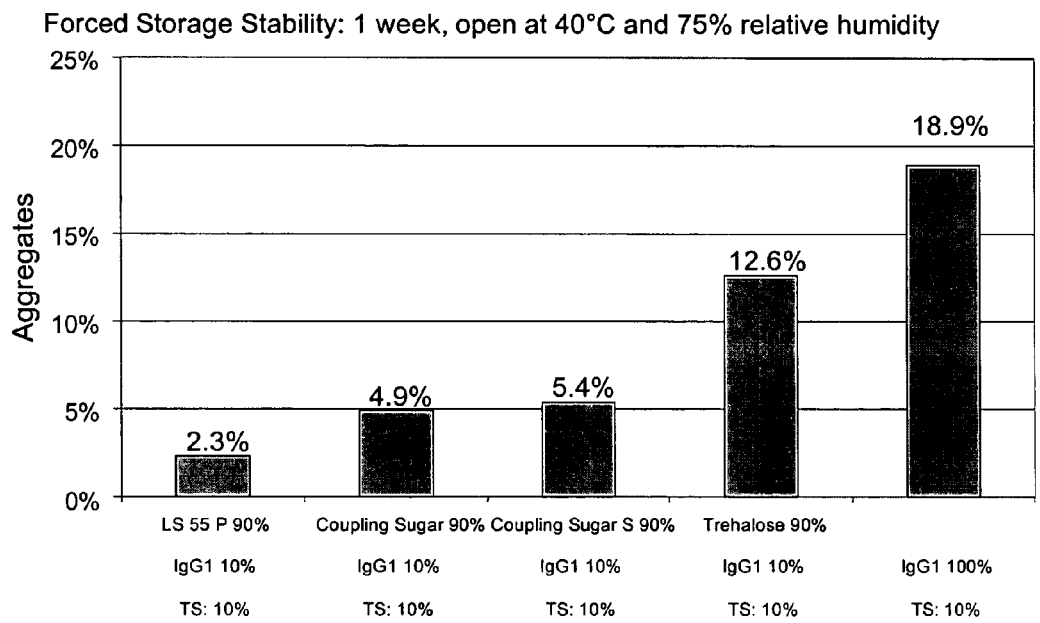

Figure: 5
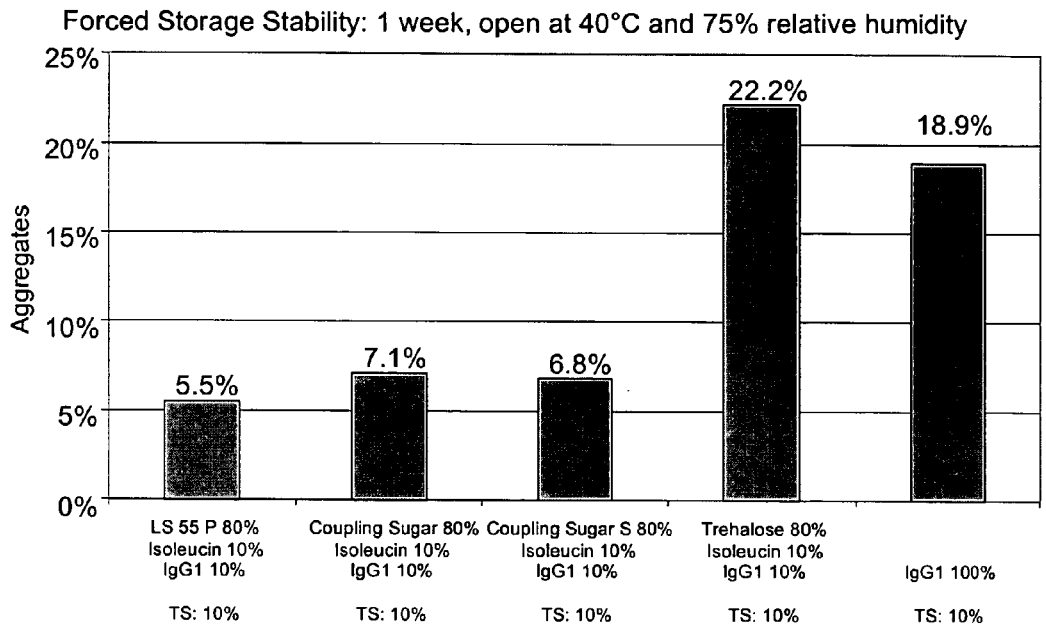
Figure: 6
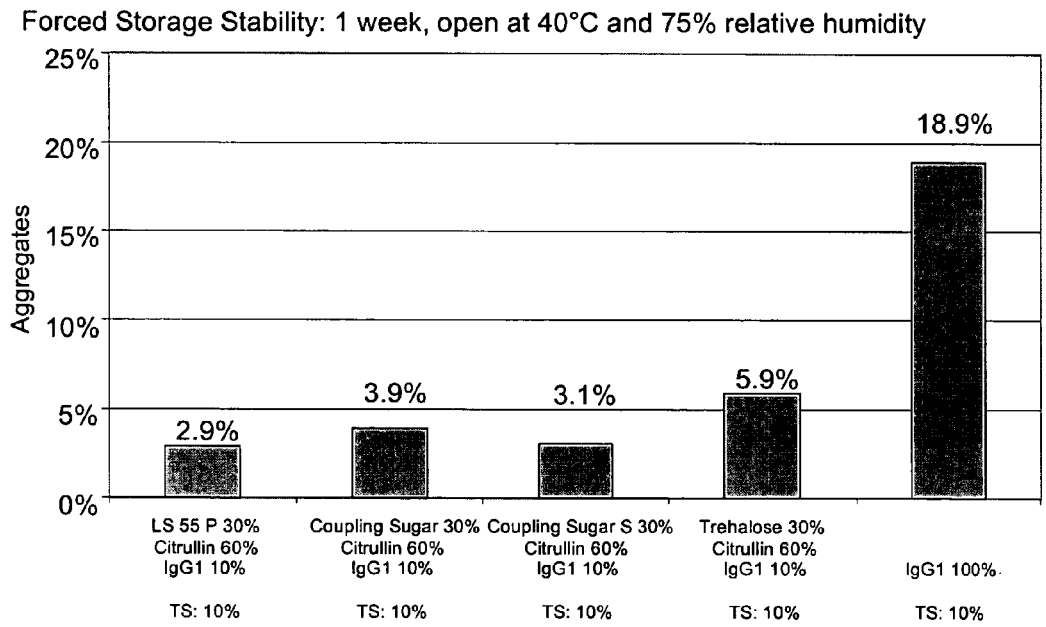

Figure: 7
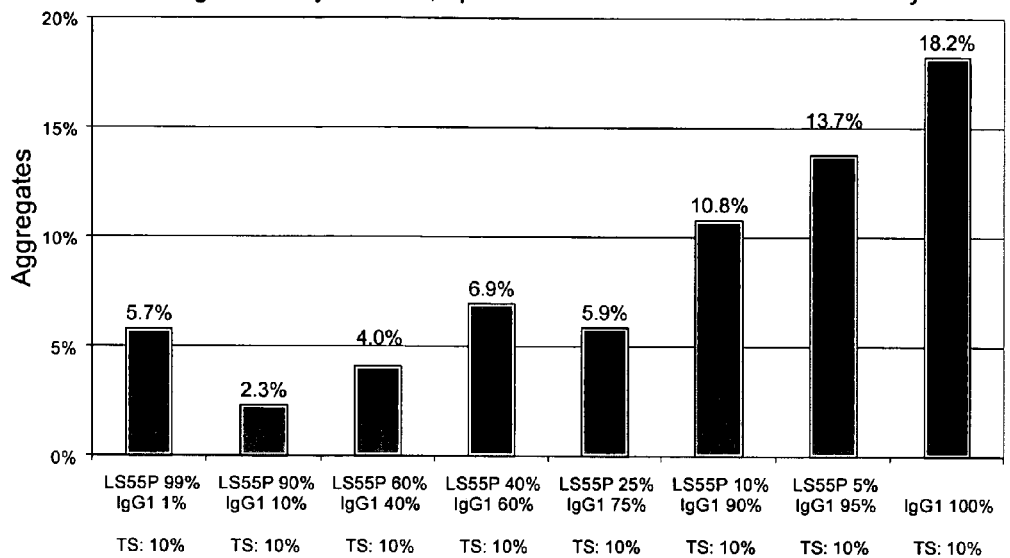
Figure: 8
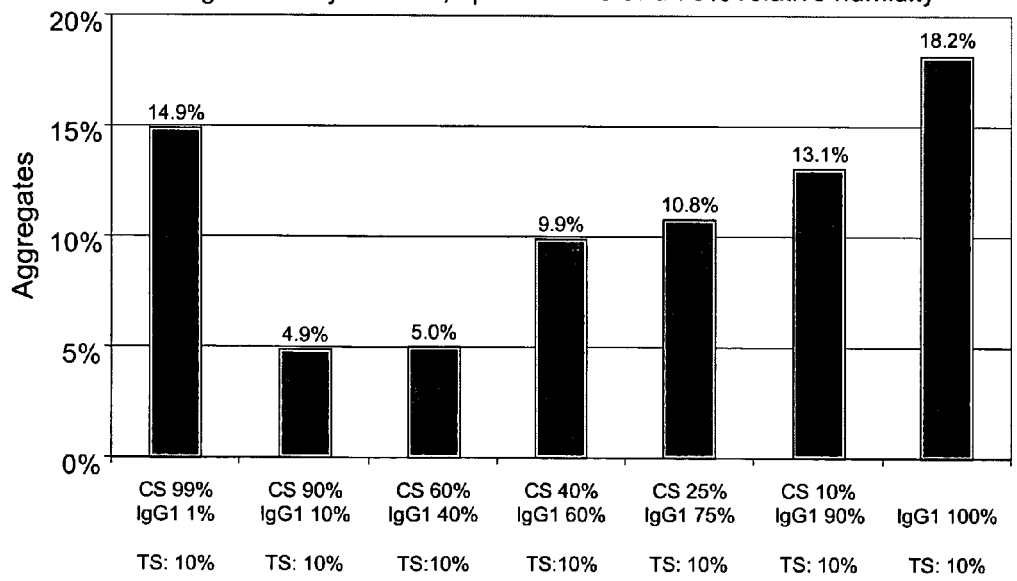

Figure: 9
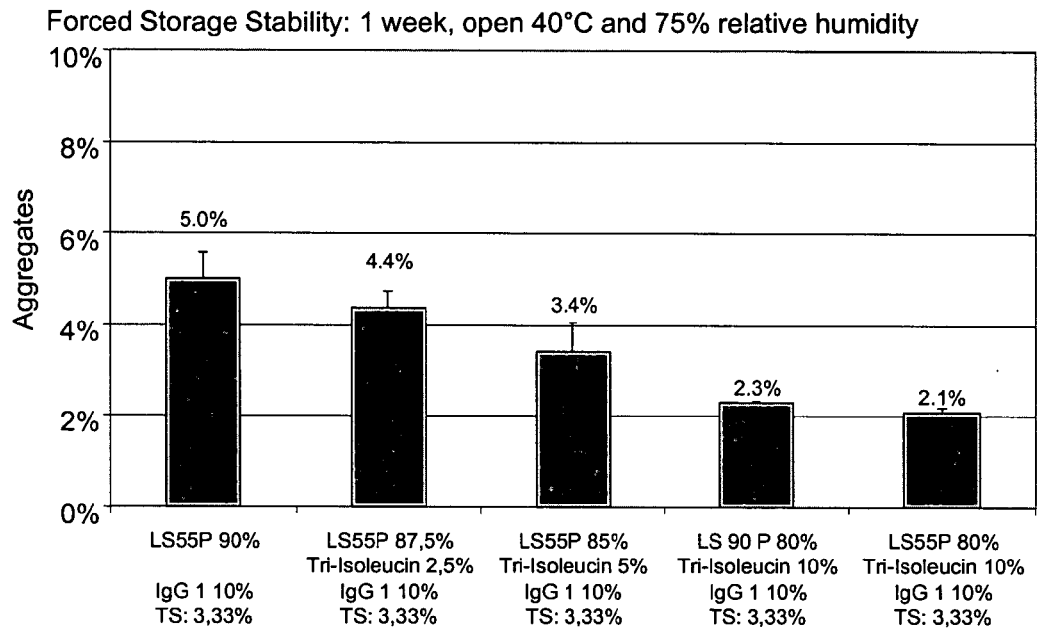
Figure: 10
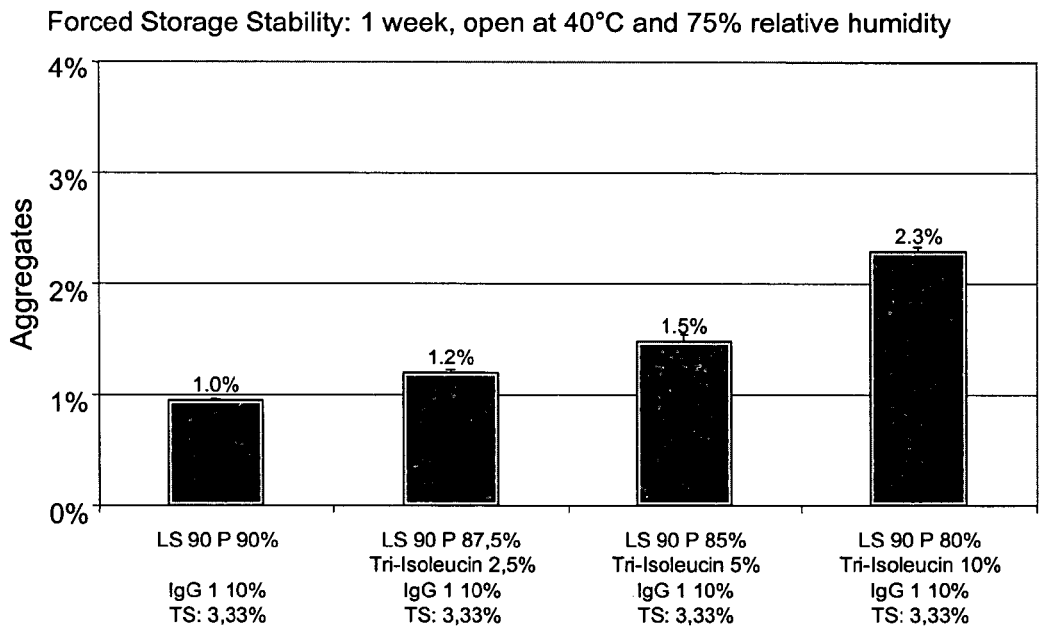

Figure: 11
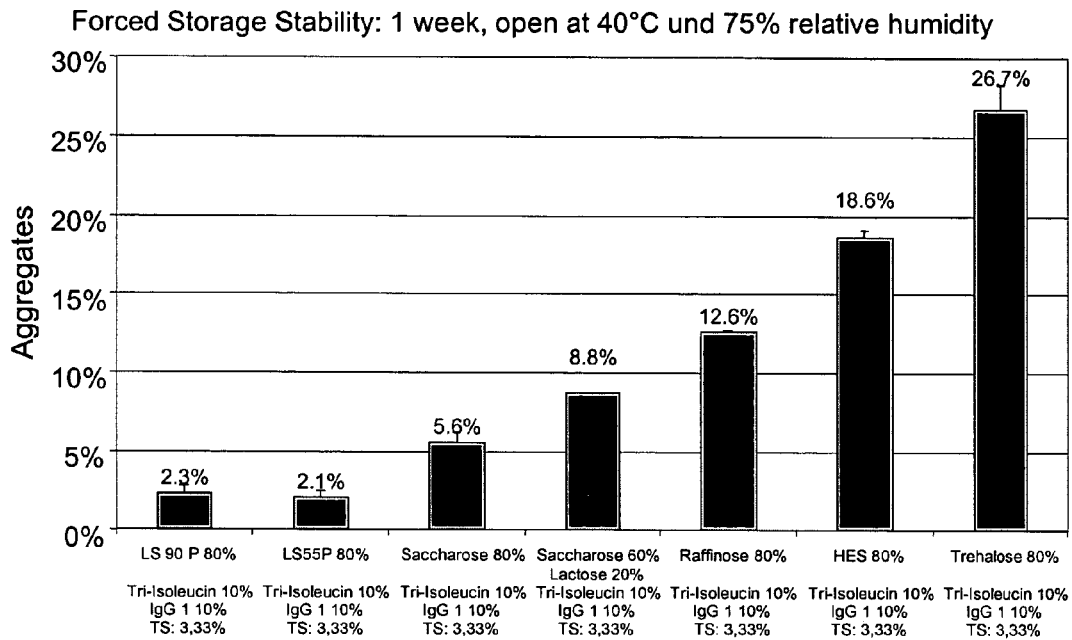
Figure: 12
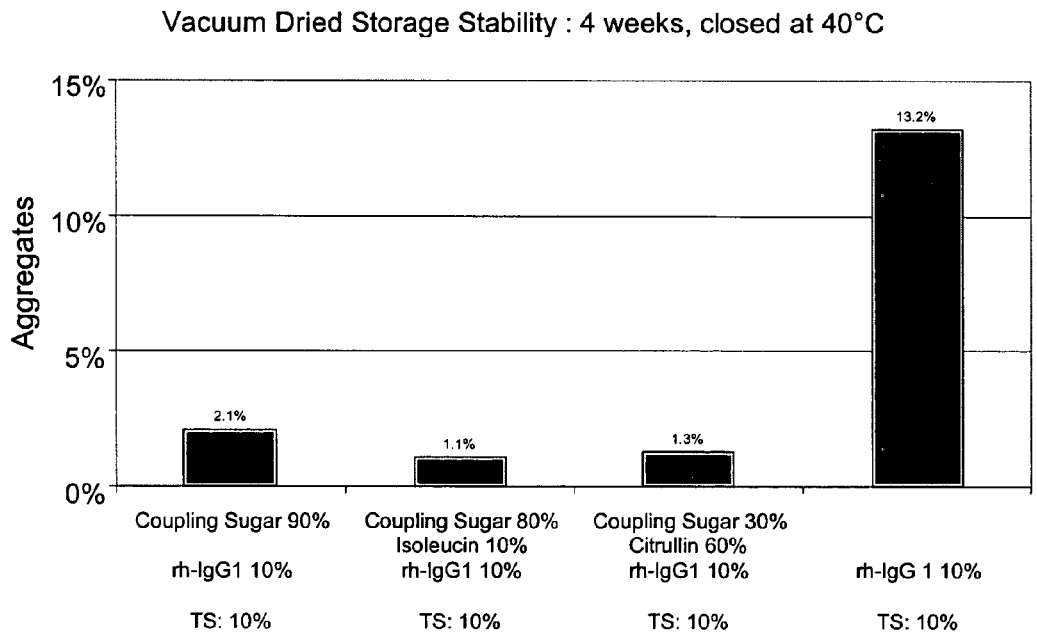

Figure: 13
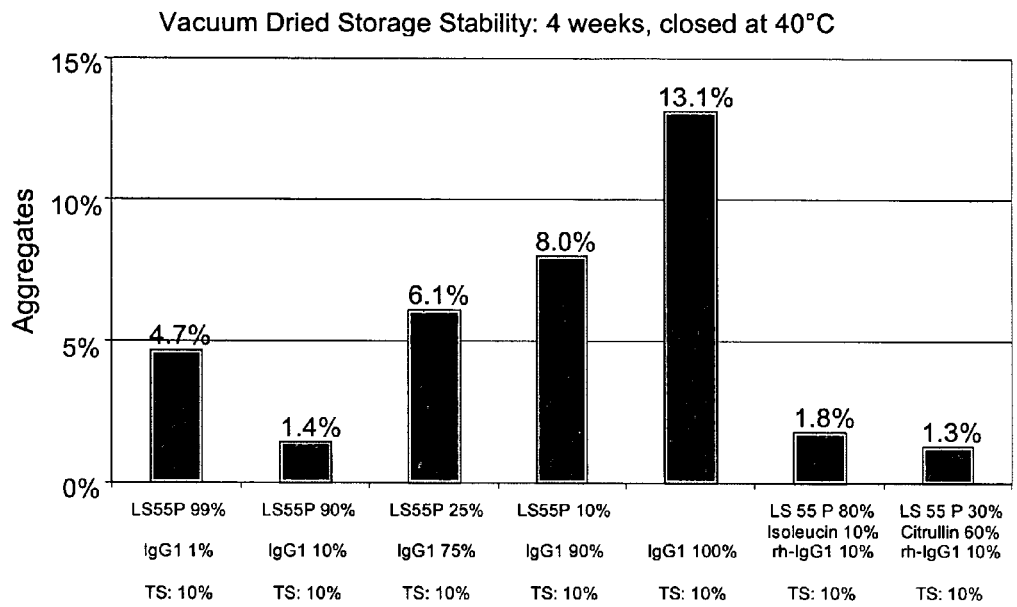
Figure: 14a
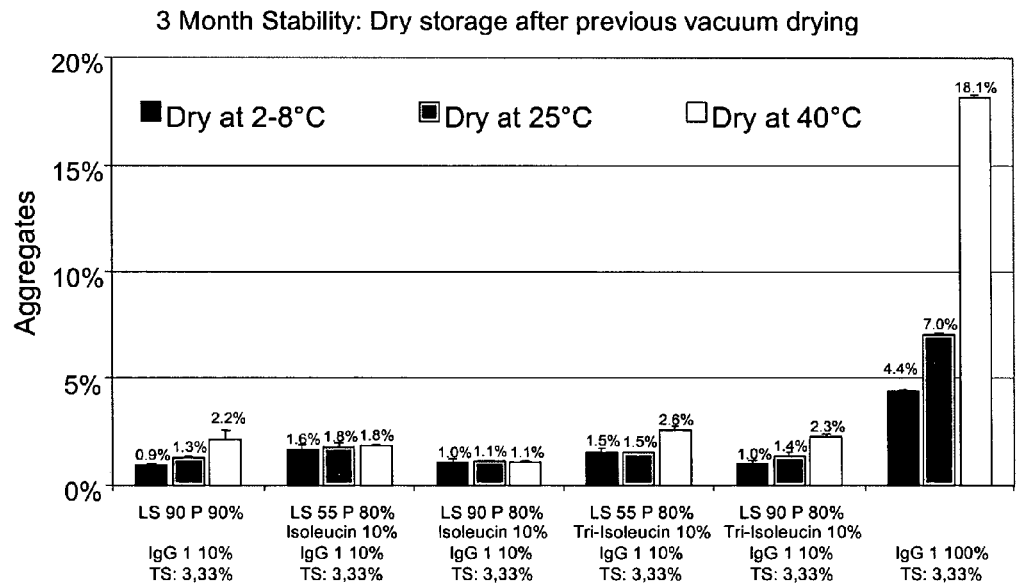

Figure: 14b
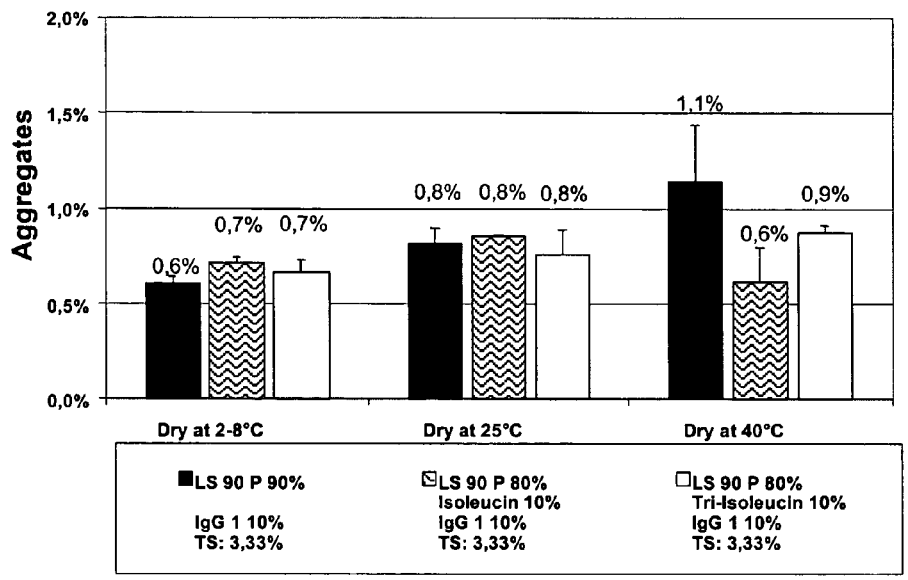
Figure: 15a
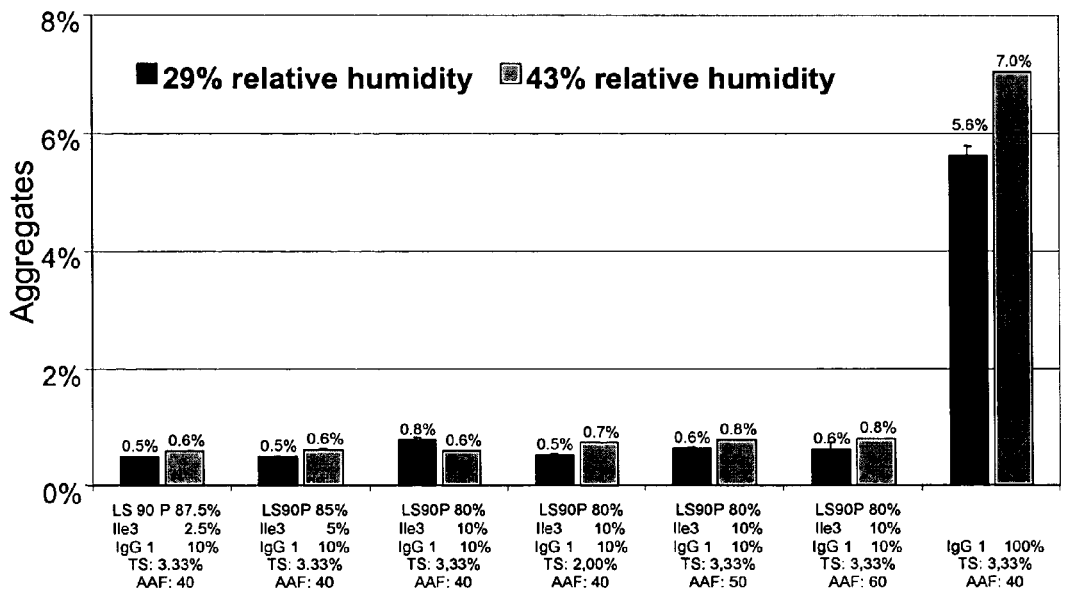

Figure: 15b
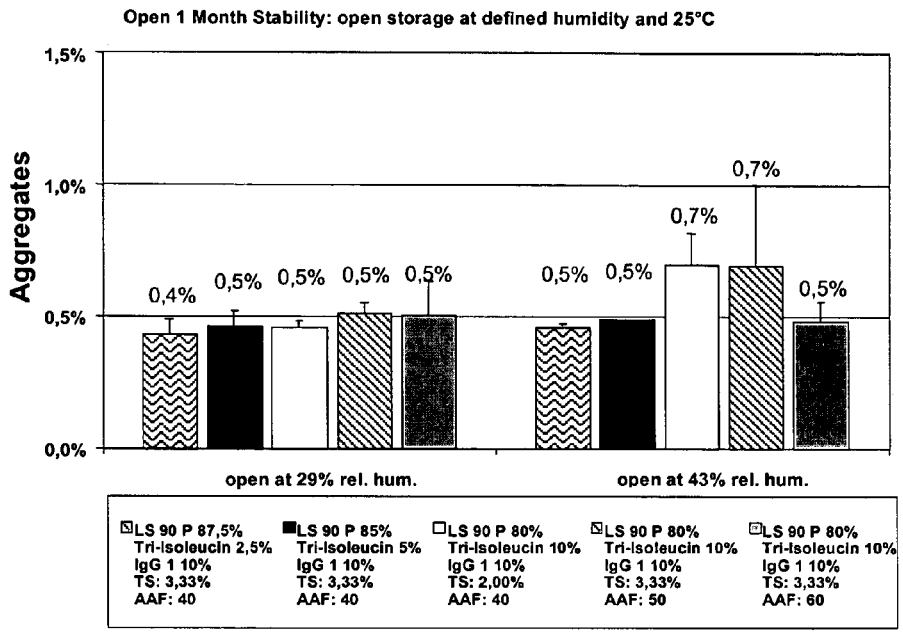
Figure: 16
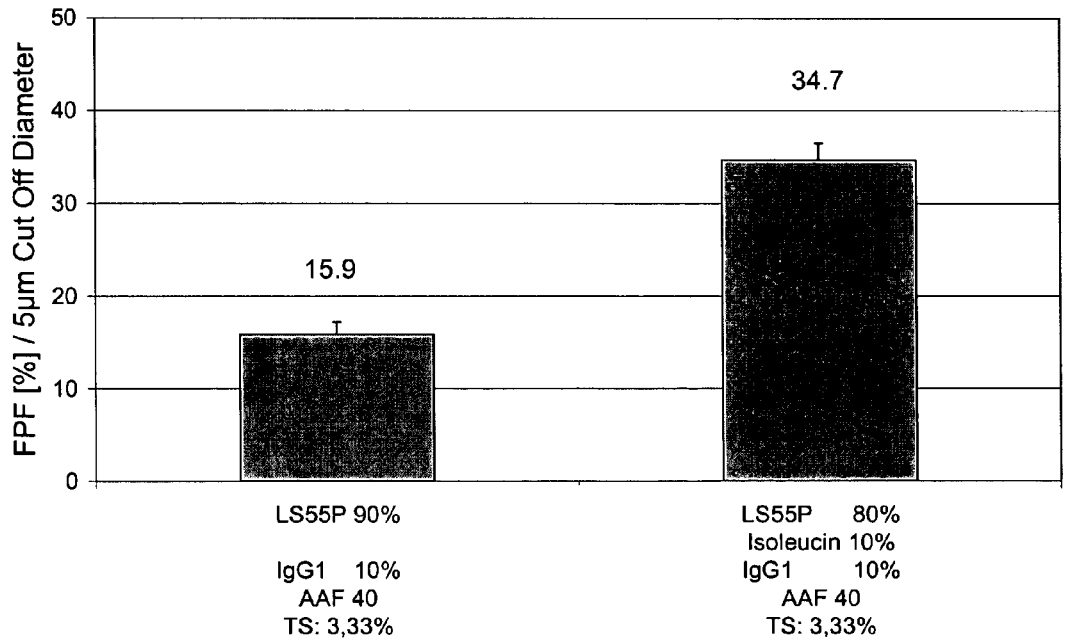

Figure: 17
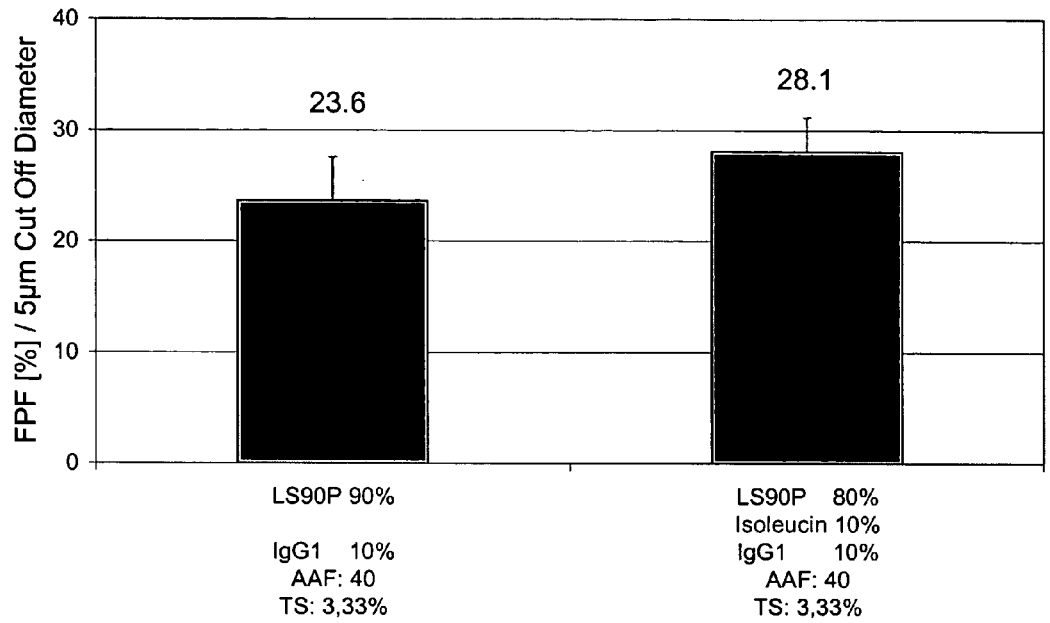
Figure: 18
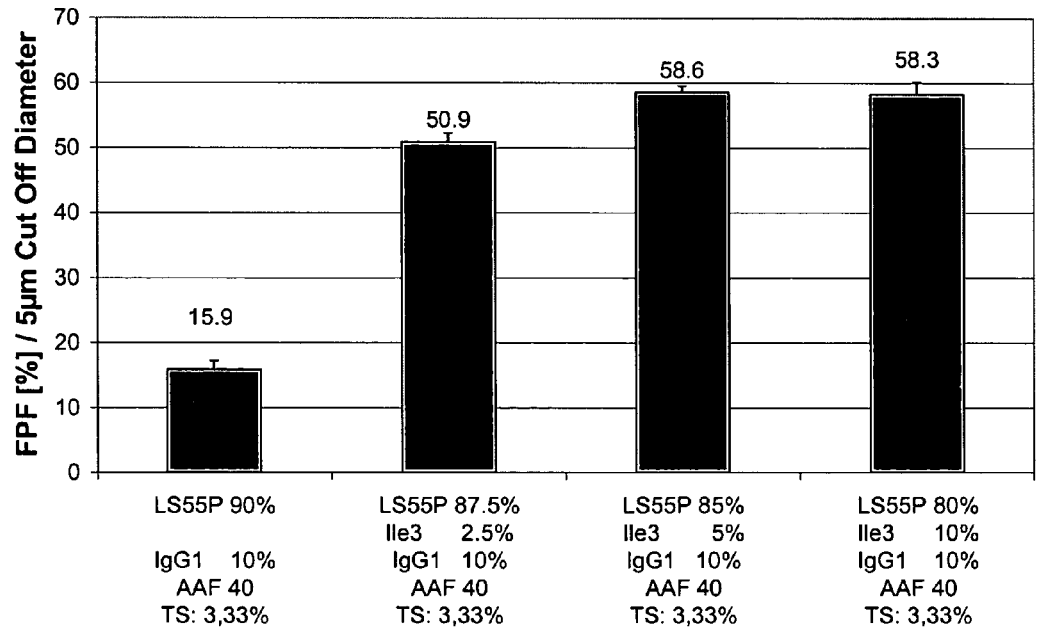

Figure: 19
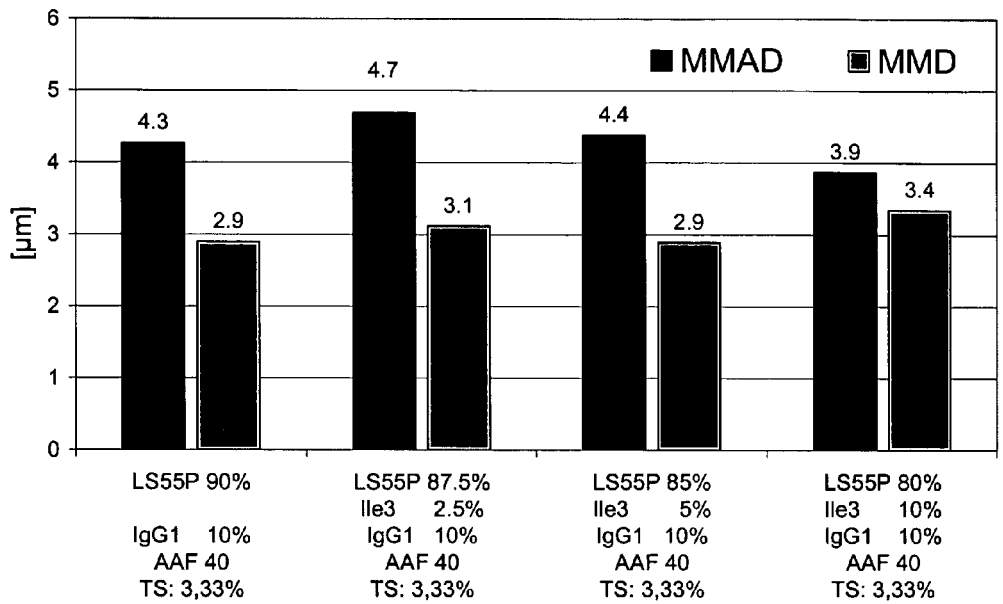
Figure: 20
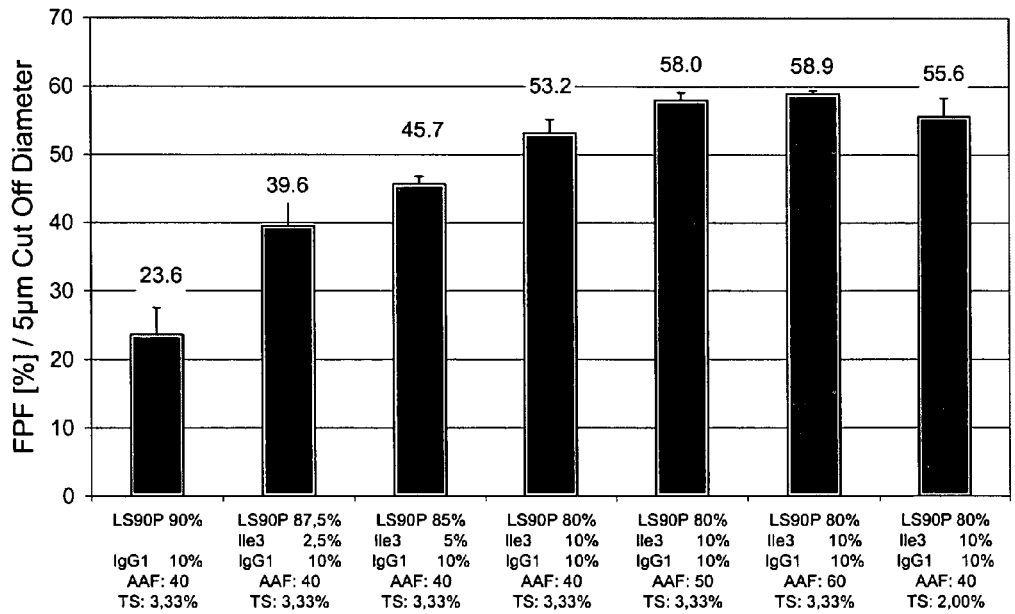

Figure: 21
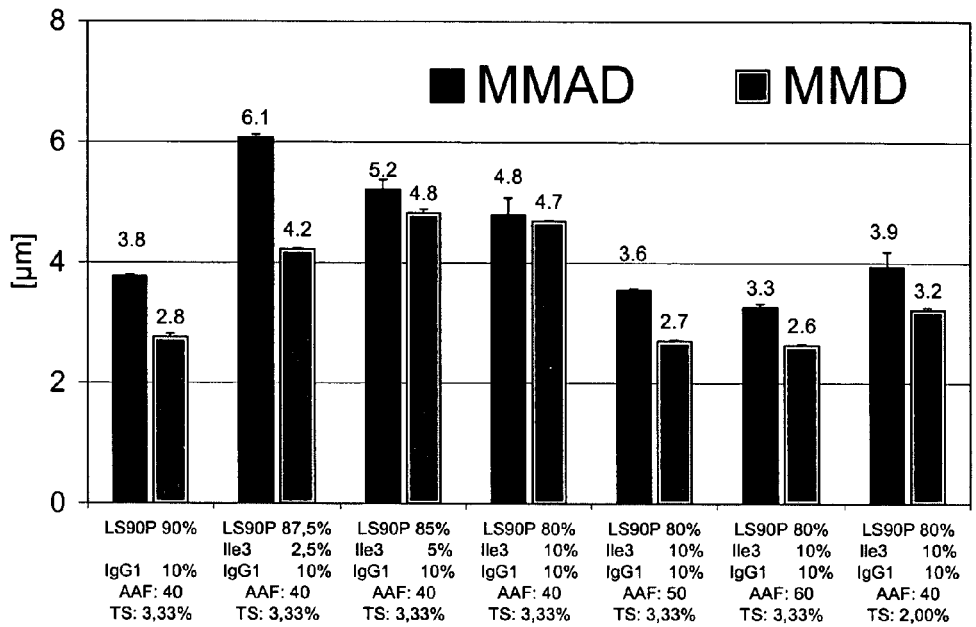
Figure: 22
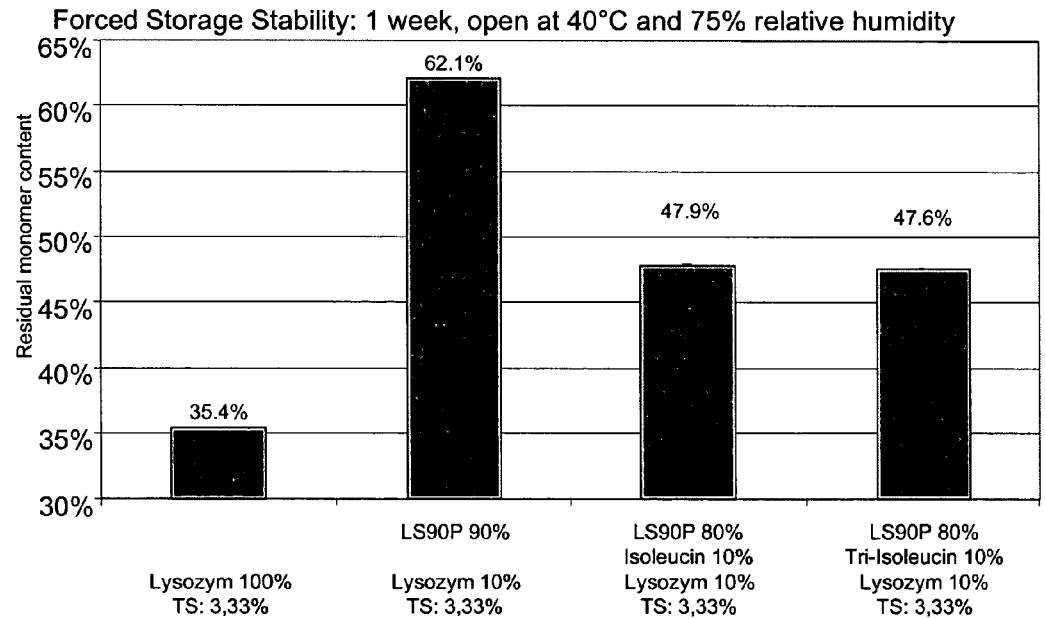

Figure: 23
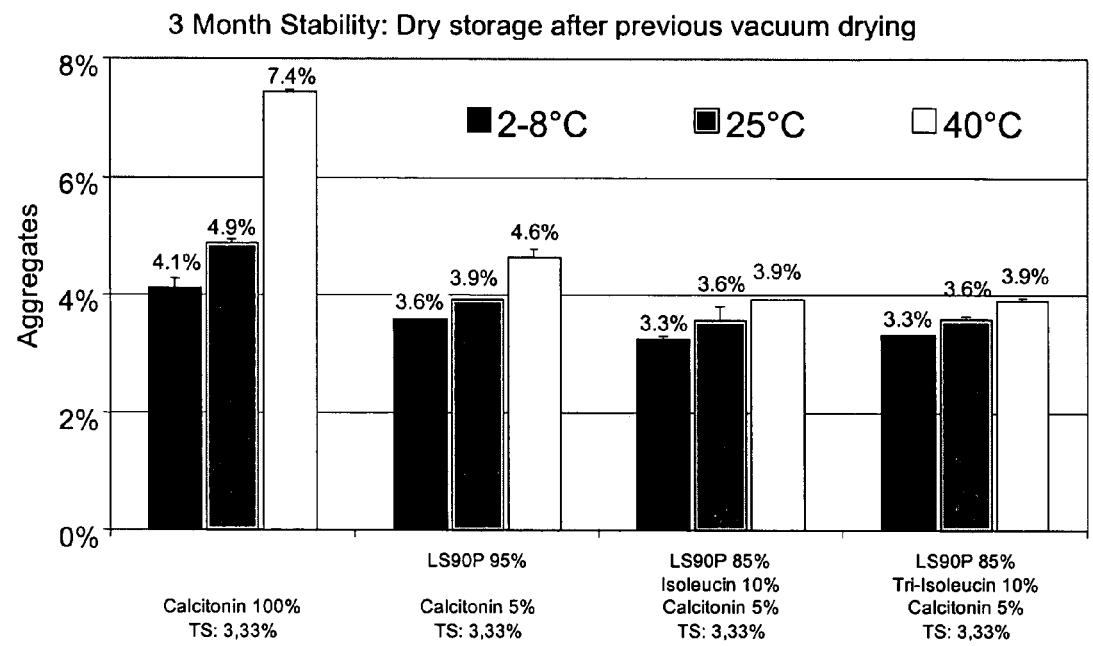

Figure: 24
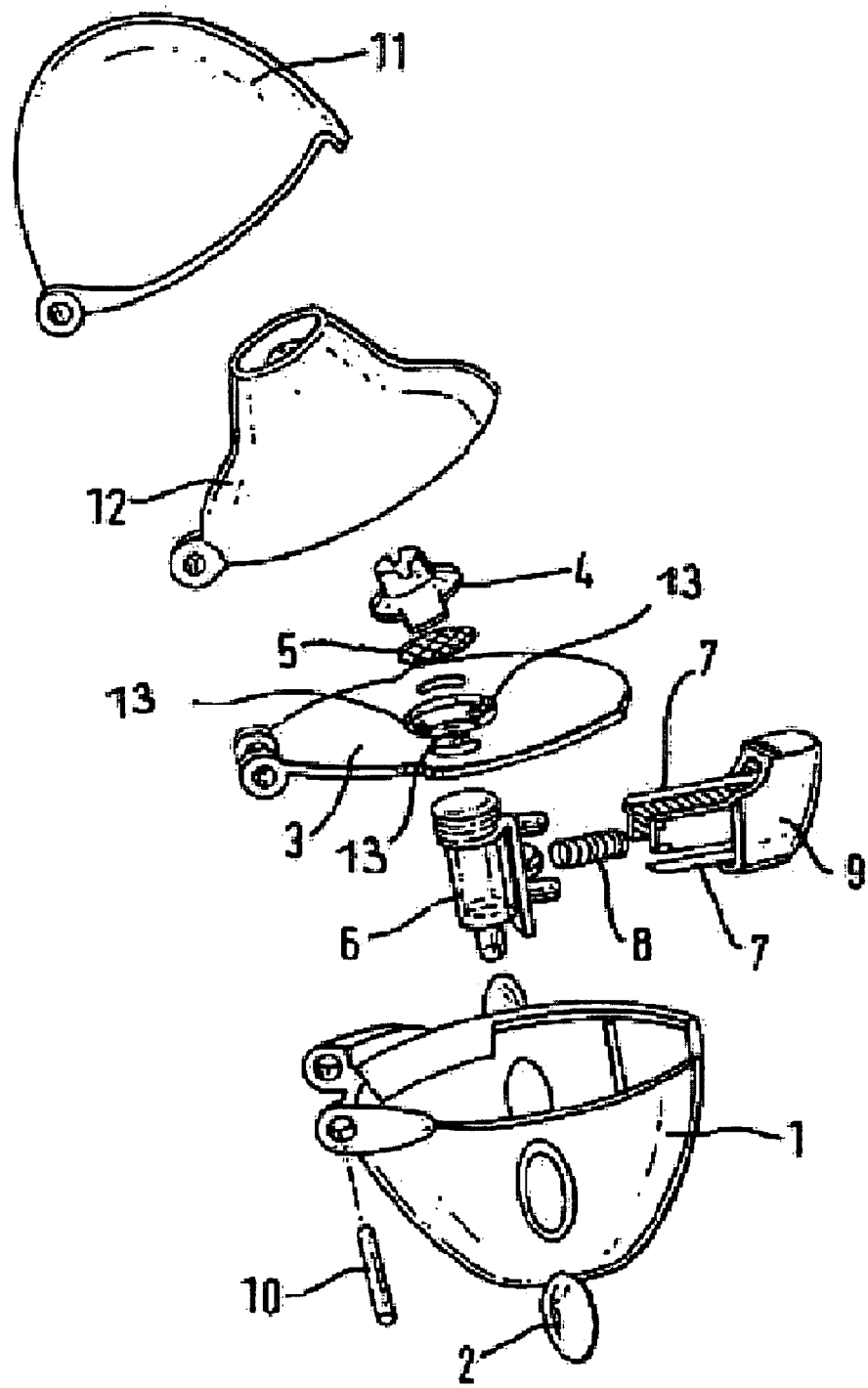

POWDER COMPRISING NEW COMPOSITIONS OF OLIGOSACCHARIDES AND METHODS FOR THEIR PREPARATION

APPLICATION DATA

This application claims benefit to German application no. DE 102004022928.7 filed May 10, 2004, and U.S. provisional application No. 60/572,306 filed May 18, 2004.

FIELD OF THE INVENTION

The invention concerns the use of new oligosaccharides/compositions of oligosaccharides for the preparation and stabilization of pharmaceutical formulations, predominantly of powders which contain a pharmaceutical active substance. The powders are prepared preferably by spray-drying or freeze-drying. The present invention concerns, in particular, the corresponding powders containing antibodies and methods for their preparation.

BACKGROUND

Active substances/active substance formulation formulated in aqueous solutions are in some cases subject to instabilities which can lead to reduced efficacy or bioactivity and increased toxicity or intolerance. This applies both to classical pharmaceutical agents and to active substances containing peptides or proteins. The stability of pharmaceutical active substances can be improved by a change in the structure (internally) or by the addition of suitable excipients (externally).

A common method of external stabilization of pharmaceutical active substances is the use of suitable excipients. Excipients which stabilize active substances can be roughly classified as follows: sugars and polyols, amino acids, amines, salts, polymers and tensides.

Sugars and polyols are frequently used as non-specific stabilizers. Their stabilizing effect is attributed mainly, in the case of biological active substances, to "preferential exclusion" (Xie and Timasheff, 1997a, Biophysical Chemistry, 64(1-3), 25-43; Xie and Timasheff, 1997b, Protein Science, 6(1), 211-221; Timasheff, 1993, Annual review of biophysics and biomolecular structure, 22, 67-97). With regard to the choice of sugars, in the case of biological active substances, reducing sugars are in most cases avoided.

Saccharose and trehalose, as non-reducing sugars, are used in preference. Further examples of suitable excipients are glucose, sorbitol and glycerol (Boctor and Mehta, 1992, Journal of Pharmacy and Pharmacology, 44 (7), 600-3; Timasheff, 1993 (supra); Chang et al., 1993 Pharmaceutical Research, 10(10), 1478-83) and Mannitol (Hermann et al. 1996, Pharmaceutical Biotechnology, 9 (Formulation, Characterization, and Stability of Protein Drugs), 303-328; Chan et al. 1996 Pharmaceutical Research, 13 (5), 756-761). Furthermore, it is known that a wide variety of polymers have a stabilizing effect on pharmaceutical active substances, predominantly on proteins, for example, antibodies. Human serum albumin (HAS), which was frequently used in the past, has very good stabilizing and aggregation-inhibiting properties, but has since come to be regarded as unsuitable owing to its potential contamination with "blood-borne" pathogens. Among the polymers known so far, hydroxypropyl-β-cyclodextrin (HP-β-CD) proves especially suitable, since it can safely be administered parenterally. Further examples are high-molecular dextrans (18 to 82 kD), PVP, heparin, gelatines of type A and B and hydroxyethyl starch (HES), heparin, dextran sulphate, polyphosphoric acid, poly-L-glutamic acid, poly-L-lysine.

Alongside sugars and polyols, amino acids can also be used as stabilizers, alone or in combination with other excipients. Amino acids are preferably used in the stabilization of proteins. For example, the addition of histidine, glycine, sodium aspartate (Na-Asp), glutamate and lysine hydrochloride (Lys-HCl) inhibits the aggregation of rhKGF in 10 mM sodium phosphate buffer (pH 7.0) together with 5% mannitol (Zhang et al., 1995 Biochemistry, 34 (27), 8631-41). The combination of amino acids and propylene glycol improves, for example, the structural stability of rhCNTF (Dix et al., 1995, Pharmaceutical Research (Supplement), 12, p.97). Lysine and arginine enhance the thermostability of IL-1R (increase in Tm), whereas glycine and alanine have a destabilizing effect (Remmele et al., 1998 Pharmaceutical Research, 15(2), 200-208).

Furthermore, the stability of pharmaceutical active substances is enhanced by various drying methods. However, drying is mostly performed in the presence of excipients which are intended to maintain the stability of the active substances and improve the properties of the dry powder. A decisive factor in stabilization by drying is the immobilization of the active substance in an amorphous matrix. The amorphous state has high viscosity with low molecular motility and low reactivity. Beneficial excipients must thus be capable of forming an amorphous matrix with the highest possible glass transition temperature, into which matrix the active substance is embedded. The choice of excipients thus depends particularly on their stabilization capacities. However, besides this, factors such as the pharmaceutical acceptability of the excipient and its influence on particle formation, dispersibility and flow property also play a decisive role, especially when spray-drying methods are being used.

Spray-drying represents an especially suitable method of enhancing the chemical and physical stability of peptide-/protein-type pharmaceutical active substances (Maa et al., 1998, Pharmaceutical Research, 15(5), 768-775). Especially in the area of pulmonary therapy, spray-drying is being increasingly used (U.S. Pat. No. 5,626,874; U.S. Pat. No. 5,972,388; Broadhead et al., 1994, J. Pharm. Pharmacol., 46(6), 458-467), since administration by inhalation now represents an alternative, even in the treatment of systemic diseases (WO 99/07340). It is a prerequisite that the mean particle size of the powder is in the range of 1-10 µm, preferably 1-7.5 µm, so that the particles can reach the deeper sections of the lungs and thus the bloodstream. The DE-A-179 22 07 gives an exemplary description of the preparation of such spray-dry particles. In the meantime a large number of methods for the preparation of such powders have been described (WO 95/31479; WO 96/09814; WO 96/32096; WO 96/32149; WO 97/41833; WO 97/44013; WO 98/16205; WO 98/31346; WO 99/66903; WO 00/10541; WO 01/13893; Maa et al., 1998, supra; Vidgrén et al., 1987, Int. J. Pharmaceutics, 35, 139-144; Niven et al., 1994, Pharmaceutical Research, 11(8), 1101-1109).

Also suitable as excipients are sugars and their alcohols (e.g. trehalose, lactose, saccharose or mannitol) and various polymers (Maa et al., 1997, Pharm. Development and Technology, 2(3), 213-223; Maa et al., 1998, supra; Dissertation Adler, 1998, University of Erlangen; Costantino et al., 1998, J. Pharm. Sci., 87(11), 1406-1411). However, the excipients chiefly used have various drawbacks. The addition of trehalose and mannitol, for example, has a detrimental effect on the flow properties of spray-dry formulations (C. Bosquillon et al., 2001, Journal of Controlled Release, 70(3), 329-339).

Mannitol is additionally prone to recrystallization when the content is more than 20 per cent by weight (Costantino et al., 1998, supra), with the result that stabilizing effects decrease dramatically. Lactose, a frequently used excipient, certainly improves the flow properties of spray-dry formulations (C. Bosquillon et al., 2001, supra), but is problematic, especially in the formulation of peptide-/protein-containing active substances, since lactose can enter into destabilizing Maillard reactions with peptides/proteins, owing to its reducing property.

In the spray-drying of antibodies without the addition of stabilizers, the native secondary structure regularly develops as a result of dehydration, heat and shear and this leads to dramatic loss of bioactivity. Hydrophobic parts of the antibody, which were previously turned inward, turn outwards in this process. This occurs to a greater extent at the hydrophobic interfaces between the water droplets arising in the course of spray-drying and the air. In addition, antibodies within the aqueous phase aggregate to dimmers or aggregates of a high order. This aggregation is often irreversible. Furthermore, the high temperature at which the proteins are sprayed represents a critical parameter. As a result of the high input of energy there can be destabilization of the peptide bonds and denaturing of the antibody. Furthermore, aggregation of spray-dried antibodies occurs during storage of the powder. The residual water content in the powder, in particular, has negative effects in this regard. Protein aggregates are distinguished by reduced or absent biological activity and increased antigenicity.

Oligosaccharides known as Coupling Sugars with the main components maltosyl sucrose and glucosyl sucrose and lactosucrose are used in foodstuffs. They are used as fillers and dispersing agents together with sweeteners such as aspartame, as moderately sweet components in chewing gums, to stabilize trehalose syrups against crystallization or as so-called NDOs (non-digestible oligosaccharides). An improvement and stabilization of the sweetening quality of asparagyl peptides or of the sweet-sour ratio in drinks containing roughage and sweeteners is also known (US 2003/0059511, EP 1 223 175, DE 199 53 727). The use of oligosaccharides for the stabilization of suspensions of therapeutic proteins and fat or oil bases is also known from U.S. Pat. No. 5,489,577 and EP 0630 651. It is explained that without premixing with the oligosaccharides, with blending and kneading with the hydrophobic, semi-solid masses, the proteins would lose their activity. The stabilization potential during storage, in hydrophilic mixtures or in powders, is not mentioned in any way.

An object of the invention was to make available new excipients/mixtures of excipients for the preparation of pharmaceutical formulations. The corresponding formulations should be distinguished, inter alia, by good long-term stability.

A further object of the present invention was to provide new excipients/excipient mixtures for the preparation of dried pharmaceutical formulations. The corresponding powder-type pharmaceutical formulations should be distinguished by good long-term stability and, if possible, by inhalability.

A further object of the present invention was to provide new excipients/excipient mixtures for the preparation of peptide-/protein-containing pharmaceutical formulations, in particular for such as are produced by spray-drying. The corresponding peptide-/protein-containing pharmaceutical formulations should again be distinguished by good long-term stability and, if possible, by inhalability.

A further object of the present invention was to provide new excipients/excipient mixtures for preparing formulations of therapeutic antibodies or antibody derivatives, especially for those produced by spray-drying. The corresponding antibody-containing pharmaceutical formulations should again be distinguished by good long-term stability and, if possible, by inhalability.

A further object of the present invention was to provide appropriate pharmaceutical formulations for administration by inhalation, whether in the form of a dry powder, a propellent-gas-containing metered dose aerosol or a propellent-gas-free inhalation solution.

The objects forming the basis of the patent are achieved by the following embodiments and by the subject matter/methods disclosed in the patent claims.

SUMMARY OF THE INVENTION

The present invention concerns powders containing a pharmaceutical active substance and a combination of excipients comprising at least one 1,4 O-linked saccharose derivative selected from the compounds: 1,4 O-linked D-Gal-saccharose (lactosucrose), 1,4 O-linked D-Glu-saccharose (glucosyl sucrose), or 1,4 O-linked Glu-Glu-saccharose (maltosyl sucrose) in combination with at least one further excipient. The other excipient is preferably an amino acid, a peptide and/or a mono-, di- and/or oligosaccharide, wherein the oligosaccharide may be a second 1,4 O-linked saccharose derivative, provided that this is different from the first.

The term lactosucrose means molecules with the following structure:

In the terms of the present invention, the term glucosyl sucrose means molecules with the following structure:

The term maltosyl sucrose means molecules with the following structure:

A combination of excipients according to the invention is, for example, a mixture of sugars which contains, together with at least one 1,4 O-linked saccharose derivative, at least one further sugar in the form of a mono-, di-, and/or oligosaccharide. According to a preferred embodiment the mixture of sugars will be, for example, lactosucrose in combination with lactose and saccharose or a combination of glucosyl and maltosyl sucrose, which may in turn contain further mono-, di- or oligosaccharides.

According to a further embodiment, the combination of excipients according to the invention is a mixture of at least one 1,4 O-liked saccharose derivative in combination with an amino acid, preferably isoleucine.

A further combination of excipients according to the invention is a mixture of at least one 1,4 O-linked saccharose derivative in combination with a peptide which is not the identical to the pharmaceutical active substance. Preferably, the peptide contains one or several isoleucine residues. According to a further preferred embodiment, the peptide is a di- or tripeptide, an isoleucine-containing tripeptide or dipeptide being particularly preferred, the use of tri-isoleucine being particularly preferred.

According to a further embodiment of the present invention, the combination of excipients is a mixture of sugars containing at least one 1,4 O-linked saccharose derivative and at least one further mono-, di- and/or oligosaccharide in combination with an amino acid, preferably isoleucine, and/or a peptide, preferably a di- or tripeptide, which in turn preferably contains at least one isoleucine residue or, according to an particularly preferred embodiment, is composed of isoleucine residues.

Surprisingly, it has been found that the corresponding powders, after drying, i) form an amorphous structure, ii) show a relatively high yield (at least 75% referred to the solid used), iii) have a very high glass transition temperature, higher than 40° C. and iv) have a very low tendency to recrystallization.

The pharmaceutical active substance is preferably a biological macromolecule which can be a polypeptide or a protein, for example a growth factor, enzyme or antibody. Accordingly, the following are particularly in keeping with the invention: powders with (a) a content amounting to 25 to 99.99% (w/w), preferably of 80 to 90% (w/w) (referred to the dry mass of the powder) of one of the excipient combinations according to the invention containing at least 1,4 O-linked saccharose derivative and (b) with a biological macromolecule as the pharmaceutical active substance, preferably in a concentration of between 0.1 and 75% (w/w), again referred to the dry mass of the powder, the sum of weight percentages of the excipient combination containing at least 1,4 O-linked saccharose derivative and the biological macromolecule being a maximum of 100% (w/w).

According to a further embodiment, the present invention thus concerns powders which, referred to their dry mass, (a) have a content amounting to between 25 and 90% (w/w) of at least one 1,4 O-linked saccharose derivative or a sugar mixture containing at least one 1,4 O-linked saccharose derivative, (b) have a content amounting to between 1 and 39.99% (w/w) of at least one amino acid and/or at least one peptide as the further excipient and (c) have a content amounting to at least 0.01% (w/w) of a pharmaceutical active substance. Preferably the further excipient is the amino acid isoleucine or a di- or tripeptide, preferably with at least one isoleucine residue.

According to a special embodiment, the present invention concerns powders which, referred to their dry mass, have (a) a content amounting to about 25 to 80% (w/w) of at least one 1,4 O-linked saccharose derivative or a sugar mixture containing at least one 1,4 O-linked saccharose derivative, (b) a content amounting to about 10 to 19.99% (w/w) of an amino acid, preferably isoleucine and (c) a content amounting to about 0.01 to 65% (w/w) of a pharmaceutical active substance, preferably a peptide/protein, for example, an antibody.

According to a further special embodiment, the present invention concerns powders which, referred to their dry mass, have (a) a content amounting to about 25 to 90% (w/w) of at least one 1,4 O-linked saccharose derivative or a sugar mixture containing at least one 1.O-linked saccharose derivative, (b) a content amounting to about 1 to 19.99% (w/w) or a peptide, preferably an isoleucine-containing peptide, even more preferably an isoleucine-containing tripeptide, tri-isoleucine being particularly preferred, and (c) a content amounting to 0.01 to 74% (w/w) of a pharmaceutical active substance, preferably a peptide/protein, for example and antibody. The corresponding powders, especially after addition of an amino acid such as isoleucine, for example, or a peptide, preferably a tripeptide containing isoleucine, show very good flow properties and are distinguished by a very high proportion of inhalable particles. Furthermore the corresponding powders have very good stability to processing and storage.

According to a further embodiment, the present invention concerns powders which contain one of the excipient combinations described in this application, which contain one or several 1,4 O-linked saccharose derivative(s) or a sugar mixture containing at least one 1,4 O-linked saccharose derivative and at least one pharmaceutical active substance, the corresponding powder having a glass transition temperature above 40° C., preferably above 45° C., more preferably above 50° C., even more preferably above 55° C., a temperature of above 60° C. being particularly preferred. Usually the corresponding powders according to the invention have a maximum glass transition temperature of about 96 to 110° C. However in individual cases the value may be even higher. The content of added excipient, in particular the content of 1,4 O-linked saccharose derivative or the content of the mixture of derivatives in the powder is primarily responsible for the corresponding glass transition temperature.

The powders according to the invention are preferably spray-dried or freeze-dried powders, wherein spray-dried powders are particularly preferred.

According to a further embodiment the present invention concerns pharmaceutical formulations for administration by inhalation, which contain one of the powders according to the invention described here or are made up of these or a prepared from these. In this connection, preferred formulations are pharmaceutical formulations which contain the powders according to the invention as powders for inhalation, metered dose aerosols containing propellent gas or as propellent-gas-free inhalation solutions after reconstitution. The dried, preferably spray-dried powders according to the invention used for the preparation of the pharmaceutical formulation are distinguished, according to a further embodiment, by a high content of inhalable particles with a median aerodynamic particle diameter (MMAD) of less than 10 μm, preferably of 0.5-7.5 μm, more preferably 0.5-5.5 μm, 0.5-5.0 μm being particularly preferred.

The invention further makes available methods of preparing the corresponding powders according to the invention, characterized in that a solution or suspension which contains at least one or several 1,4 O-linked saccharose derivative(s) from among the above-described compounds or a sugar mixture containing these and at least one pharmaceutical active substance is prepared and that this is sprayed under suitable conditions. The temperature for the spraying process is preferably between 50 and 200° C. (inlet temperature) and between 30 and 150° C. (outlet temperature)

DESCRIPTION OF THE FIGURES

All percentage data specified in the descriptions relate to concentrations of solids in solutions (w/w). All legends in the drawings described below relate to the percentage (w/w) composition of powders achieved by spray drying and freeze drying with ensuing pulverization. The legends further specify the total solids concentrations of solutions (total solids=TS) in percent (w/w). In the legend of FIG. 8, Coupling Sugar is abbreviated to CS. In the legends of FIGS. 18, 19, 20, and 21, tri-isoleucine is abbreviated to Ile3. FIGS. 15, 16, 17, 18, 19, 20, and 21 further specify the atomization rate (AAF=atomizing air flow) set during the spray drying process on the Büichi B-290. The FIG. 40 then corresponds to a real volume flow of ~0.67 m$^3$/h, 50 to a real volume flow of ~1.05 m$^3$/h, and 60 to a real volume flow of ~1.74 m$^3$/h. In all other drawings, the atomization rate of 40 corresponded to a real volume flow of ~0.67 m$^3$/h respectively.

FIG. 1 shows the aggregate content after freeze drying, pulverization, one week's open storage at 75% relative humidity and 40° C. (forced storage stability), and reconstitution. Aqueous solutions with a) 4.5% LS55P fraction and 0.5% IgG fraction, b) 4.5% Coupling Sugar fraction and 0.5% IgG fraction, c) 5.0% IgG fraction, and d) 4.5% mannitol fraction and 0.5% IgG fraction were freeze-dried. Both the LS55P- and Coupling Sugar-containing powders are distinguished by a low aggregate fraction.

FIG. 2 shows the aggregate content after freeze drying, pulverization, equilibration, and four weeks' dry storage at 40° C. (equilibrated storage stability), and reconstitution. Aqueous solutions with a) 4.5% LS55P fraction and 0.5% IgG fraction, b) 4.5% Coupling Sugar fraction and 0.5% IgG fraction, c) 5.0% IgG fraction, and d) 4.5% mannitol fraction and 0.5% IgG fraction were freeze-dried. Both the LS55P- and Coupling Sugar-containing powders are distinguished by a low aggregate fraction.

FIG. 3 shows the aggregate content after freeze drying, pulverization, vacuum drying, four weeks' dry storage at 40° C. (vacuum-dried storage stability), and reconstitution. Aqueous solutions with a) 4.5% LS55P fraction and 0.5% IgG fraction, b) 4.5% Coupling Sugar fraction and 0.5% IgG fraction, c) 5.0% IgG fraction, and d) 4.5% mannitol fraction and 0.5% IgG fraction were freeze-dried. Both the LS55P- and Coupling Sugar-containing powders are distinguished by a low aggregate fraction.

FIG. 4 shows the aggregate content after spray drying, one week's open storage at 75% relative humidity and 40° C. (forced storage stability), and reconstitution. Aqueous solutions with a) 9% LS55P fraction and 1% IgG fraction, b) 9% Coupling Sugar fraction and 1% IgG fraction, c) 9% Coupling Sugar S fraction and 1% IgG fraction, d) 9% trehalose fraction and 1% IgG fraction, and e) 10% IgG fraction were spray-dried. Both the LS55P- as well as the Coupling Sugar- and Coupling Sugar S-containing powders are distinguished by a low aggregate fraction.

FIG. 5 shows the aggregate content after spray drying, one week's open storage at 75% relative humidity and 40° C. (forced storage stability), and reconstitution. Aqueous solutions with a) 8% LS55P fraction, 1% isoleucine fraction, and 1% IgG fraction, b) 8% Coupling Sugar fraction, 1% isoleucine fraction, and 1% IgG fraction, c) 8% Coupling Sugar S fraction, 1% isoleucine fraction, and 1% IgG fraction, d) 8% trehalose fraction, 1% isoleucine fraction, and 1% IgG fraction, and e) 10% IgG fraction were spray-dried. Both the LS55P- as well as the Coupling Sugar- and Coupling Sugar S-containing powders are distinguished by a low aggregate fraction.

FIG. 6 shows the aggregate content after spray drying, one week's open storage at 75% relative humidity and 40° C. (forced storage stability), and reconstitution. Aqueous solutions with a) 3% LS55P fraction, 6% citrulline fraction, and 1% IgG fraction, b) 3% Coupling Sugar fraction, 6% citrulline fraction, and 1% IgG fraction, c) 3% Coupling Sugar S fraction, 16% citrulline fraction, and 1% IgG fraction, d) 3% trehalose fraction, 6% citrulline fraction, and 1% IgG fraction, and e) 10% IgG fraction were spray-dried. Both the LS55P- as well as the Coupling Sugar- and Coupling Sugar S-containing powders are distinguished by a low aggregate fraction.

FIG. 7 shows the aggregate content after spray drying, one week's open storage at 75% relative humidity and 40° C. (forced storage stability), and reconstitution. Aqueous solutions with a) 9.9% LS55P fraction and 0.1% IgG fraction, b) 9% LS55P fraction and 1% IgG fraction, c) 6% LS55P fraction and 4% IgG fraction, d) 4% LS55P fraction and 6% IgG fraction, e) 2.5% LS55P fraction and 7.5% IgG fraction, f) 9% LS55P fraction and 1% IgG fraction, g) 0.5% LS55P fraction and 9.5% IgG fraction, and h) 10% IgG fraction were spray-dried. The LS55P-containing powders are distinguished by a low aggregate fraction.

FIG. 8 shows the aggregate content after spray drying, one week's open storage at 75% relative humidity and 40° C. (forced storage stability), and reconstitution. Aqueous solutions with a) 9.9% Coupling Sugar fraction and 0.1% IgG fraction, b) 9% Coupling Sugar fraction and 1% IgG fraction, c) 6% Coupling Sugar fraction and 4% IgG fraction, d) 4% Coupling Sugar fraction and 6% IgG fraction, e) 2.5% Coupling Sugar fraction and 7.5% IgG fraction, f) 1% Coupling Sugar fraction and 9% IgG fraction, and g) 10% IgG fraction were spray-dried. The LS55P-containing powders are distinguished by a low aggregate fraction.

FIG. 9 shows the aggregate content after spray drying, one week's open storage at 75% relative humidity and 40° C. (forced storage stability), and reconstitution. Aqueous solutions with a) 3.00% LS55P fraction and 0.33% IgG fraction, b) 2.9166% LS55P fraction, 0.0833% tri-isoleucine fraction, and 0.33% IgG fraction, c) 2.833% LS55P fraction, 0.166% tri-isoleucine fraction, and 0.33% IgG fraction, and d) 2.66% LS55P fraction, 0.33% tri-isoleucine fraction, and 0.33% IgG fraction were spray-dried. The LS55P-containing powders are distinguished by a low aggregate fraction. Protein aggregation is further significantly reduced by an increase in the tri-isoleucine fraction from 0% to 10% in relation to the total solids content of the LS55P-containing powders.

FIG. 10 shows the aggregate content after spray drying, one week's open storage at 75% relative humidity and 40° C. (forced storage stability), and reconstitution. Aqueous solutions with a) 3.00% LS90P fraction and 0.33% IgG fraction, b) 2.9166% LS90P fraction, 0.0833% tri-isoleucine fraction, and 0.33% IgG fraction, c) 2.833% LS90P fraction, 0.166% tri-isoleucine fraction, and 0.33% IgG fraction, and d) 2.66% LS90P fraction, 0.33% tri-isoleucine fraction, and 0.33% IgG fraction were spray-dried. The LS90P-containing powders are distinguished by a low aggregate fraction.

FIG. 11 shows the aggregate content after spray drying, one week's open storage at 75% relative humidity and 40° C. (forced storage stability), and reconstitution. Aqueous solutions with a) 2.66% LS90P fraction, 0.33% tri-isoleucine fraction, and 0.33% IgG fraction, b) 2.66% LS55P fraction, 0.33% tri-isoleucine fraction, and 0.33% IgG fraction, c) 2.66% saccharose fraction, 0.33% tri-isoleucine fraction, and 0.33% IgG fraction, d) 2.00% saccharose fraction, 0.66% lactose fraction, 0.33% tri-isoleucine fraction, and 0.33% IgG fraction, e) 2.66% raffinose fraction, 0.33% tri-isoleucine fraction, and 0.33% IgG fraction, f) 2.66% hydroxyethyl starch (HES) fraction, 0.33% tri-isoleucine fraction, and 0.33% IgG fraction, and g) 2.66% trehalose fraction, 0.33% tri-isoleucine fraction, and 0.33% IgG fraction were spray-dried. The LS90P- and LS55P-containing powders are distinguished by a low aggregate fraction, particularly in comparison with raffinose and hydroxyethyl starch (HES) specified as state-of-the-art.

FIG. 12 shows the aggregate content after spray drying, vacuum drying, four weeks' dry storage at 40° C. (vacuum-dried storage stability), and reconstitution. Aqueous solutions with a) 9% Coupling Sugar fraction and 1% IgG fraction, b) 8% Coupling Sugar fraction, 1% (w/w) isoleucine fraction, and 1% IgG fraction, c) 3% Coupling Sugar fraction, 6% citrulline fraction, and 1% IgG fraction, and d) 10% IgG fraction were spray-dried. The Coupling Sugar-containing powders are distinguished by a low aggregate fraction.

FIG. 13 shows the aggregate content after spray drying, vacuum drying, four weeks' dry storage at 40° C. (vacuum-dried storage stability), and reconstitution. Aqueous solutions with a) 9.9% LS55P fraction and 0.1% IgG fraction, b) 9% LS55P fraction and 1% IgG fraction, c) 2.5% LS55P fraction and 7.5% IgG fraction, d) 1% LS55P fraction and 9% IgG fraction, e) 10% IgG fraction, f) 8% LS55P fraction, 1% isoleucine fraction, and 1% IgG fraction, and g) 3% LS55P fraction, 6% citrulline fraction, and 1% IgG fraction were spray-dried. The LS55P-containing powders are distinguished by a low aggregate fraction.

FIG. 14a+b shows the aggregate content after spray drying, vacuum drying, one or three months' dry storage at 2-8° C., 25° C., and 40° C. (1 or 3 months' stability), and reconstitution. Aqueous solutions with a) 3.00% LS90P fraction and 0.33% IgG fraction, b) 2.66% LS55P fraction, 0.33% isoleucine fraction, and 0.33% IgG fraction, c) 2.66% LS90P fraction, 0.33% isoleucine fraction, and 0.33% IgG fraction, d) 2.66% LS55P fraction, 0.33% tri-isoleucine fraction, and 0.33% IgG fraction, e) 2.66% LS90P fraction, 0.33% tri-isoleucine fraction, and 0.33% IgG fraction, and f) 3.33% IgG fraction were spray-dried. Both the LS90P- and LS55P-containing powders are distinguished by a particularly low aggregate fraction after three months' storage.

FIG. 15a+b shows the aggregate content after spray drying, vacuum drying, open one or three months' dry storage at 29% relative humidity and 43% relative humidity at 25° C. respectively (open 1 or 3 months' stability), and reconstitution. Aqueous solutions with a) 2.9166% LS90P fraction, 0.0833% tri-isoleucine fraction, and 0.33% IgG fraction at an AAF of 40, b) 2.833% LS90P fraction, 0.166% tri-isoleucine fraction, and 0.33% IgG fraction at an AAF of 40, c) 2.66% LS90P fraction, 0.33% tri-isoleucine fraction, and 0.33% IgG fraction at an AAF of 40, d) 1.60% LS90P fraction, 0.20% tri-isoleucine fraction, and 0.33% IgG fraction at an AAF of 40, e) 2.66% LS90P fraction, 0.33% tri-isoleucine fraction, and 0.33% IgG fraction at an AAF of 50, f) 2.66% LS90P fraction, 0.33% tri-isoleucine fraction, and 0.33% IgG fraction at an AAF of 60, and g) 3.33% IgG fraction at an AAF of 40 were spray-dried. The LS90P-containing powders are distinguished by a particularly low aggregate fraction after three months' storage.

FIG. 16 shows the fine particle fraction (FPF) with a cut-off diameter smaller than 5 μm for various powders. The powders were produced by spray drying of aqueous solutions which have contained LS55P and IgG1 or LS55P, isoleucine and IgG1. The solutions were produced and sprayed as described under EXAMPLES. Isoleucine-containing powder has a FPF of ~35%, whereas isoleucine-free powder only has a FPF of ~16%.

FIG. 17 shows the fine particle fraction (FPF) with a cut-off diameter smaller than 5 μm for various powders. The powders were produced by spray drying of aqueous solutions which have contained LS90P and IgG1 or LS90P, isoleucine and IgG1. The solutions were produced and sprayed as described under EXAMPLES. Isoleucine-containing powder has a FPF of ~28%, whereas isoleucine-free powder only has a FPF of ~23%.

FIG. 18 shows the fine particle fraction (FPF) with a cut-off diameter smaller than 5 μm for various powders. The powders were produced by spray drying of aqueous solutions which have contained LS55P and IgG1 or LS55P, tri-isoleucine and IgG1. The solutions were produced and sprayed as described under EXAMPLES. Tri-isoleucine-containing powders have a FPF of more than 50 or 58%, whereas tri-isoleucine-free powder only has a FPF of ~16%.

FIG. 19 shows the mass median aerodynamic diameter (MMAD) and mass median diameter (MMD) of various powders. The powders were produced by spray drying of aqueous solutions which have contained LS55P and IgG1 or LS55P, tri-isoleucine and IgG1. The solutions were produced and sprayed as described under EXAMPLES. All powders have a MMAD smaller than 5 μm and a MMD smaller than 3.5 μm. The diagram shows the effect of the tri-isoleucine fraction at constant total solids concentrations and spraying parameters on the MMAD and MMD. A 10% tri-isoleucine fraction related to the total solids content of the formulation significantly reduces the MMAD.

FIG. 20 shows the fine particle fraction (FPF) with a cut-off diameter smaller than 5 μm for various powders. The powders were produced by spray drying of aqueous solutions which have contained LS90P and IgG1 or LS90P, tri-isoleucine and IgG1. The solutions were produced and sprayed as described under EXAMPLES. Tri-isoleucine-containing powders have a FPF of ~40% to ~59%, whereas tri-isoleucine-free powder only has a FPF of ~24%.

FIG. 21 shows the mass median diameter (MMD) and mass median aerodynamic diameter (MMAD) of various powders. The powders were produced by spray drying of aqueous solutions which have contained LS90P and IgG1 or LS90P, tri-isoleucine and IgG1. The solutions were produced and sprayed as described under EXAMPLES. All powders have a MMAD smaller than 6.5 μm and a MMD smaller than 5 μm. The diagram shows the effect of the tri-isoleucine fraction at constant total solids concentrations and spraying parameters on the MMAD and MMD. A 10% tri-isoleucine fraction related to the total solids content of the formulation significantly reduces the MMAD. Both a lower solids content (e.g. TS: 2%) and a higher spraying pressure (AAF of 50 or 60), however, significantly reduce the MMD.

FIG. 22 shows the residual monomer content after spray drying, forced storage, and reconstitution. Aqueous solutions with a) 3.33% (w/w) lysozyme fraction, b) 0.33% (w/w) lysozyme fraction and 3.0% (w/w) LS90P fraction, c) 0.33% (w/w) lysozyme fraction, 0.33% (w/w) isoleucine fraction, and 2.66% (w/w) LS90P fraction, and d) 0.33% (w/w) lysozyme fraction, 0.33% (w/w) tri-isoleucine fraction, and 2.66% (w/w) LS90P fraction were sprayed. The LS90P-containing powder is distinguished by a high residual monomer content.

FIG. 23 shows the aggregate content after spray drying, vacuum drying, three months' dry storage at 2-8° C., 25° C., and 40° C. (3 months' stability), and reconstitution. Aqueous solutions with a) 3.33% (w/w) calcitonin fraction, b) 0.166% (w/w) calcitonin fraction and 3.166% (w/w) LS90P fraction, c) 0.166% (w/w) calcitonin fraction, 0.33% (w/w) isoleucine fraction, and 2.833% (w/w) fraction, and d) 0.166% (w/w)

calcitonin fraction, 0.33% (w/w) tri-isoleucine fraction, and 2.833% (w/w) fraction were sprayed. The LS90P-containing powder is distinguished by a low aggregate content.

FIG. 24 shows an inhaler for application of dry powder preparations.

DETAILED DESCRIPTION OF THE INVENTION

Definitions

Terms and names used within the context of this description of the invention have the following meanings, defined below. The weights and weight percentages refer, unless otherwise stated, in each case to the dry mass of the powder or the solid content of the solutions/suspensions to be sprayed. The general forms of description "containing" or "contains" are included in the more specialized form of description "comprising". Furthermore, "singular" and "plural" are not used restrictively.

The expression "1,4 O-linked saccharose derivative" means a 1,4 O-linked saccharose derivative selected from the compounds: 1,4 O-linked D-Gal-saccharose (lactosucrose), 1,4 O-linked D-Glu-saccharose (glucosyl sucrose), or 1,4 O-linked Glu-Glu-saccharose (maltosyl sucrose), in each case with the formula stated in this patent document.

The expression "sugar mixture" or "sugar mixture comprising at least one 1,4 O-linked saccharose derivative" means i) a 1,4 O-linked saccharose derivative with one of the formulas stated in this patent document, ii) a mixture of at least two different 1,4 O-linked saccharose derivatives, each with the formula stated in this patent document, preferably a mixture of maltosyl sucrose and glucosyl sucrose, iii) a mixture of at least one 1,4 O-linked saccharose derivative with one of the formulas stated above and other sugars, preferably a mixture of lactosucrose, lactose and saccharose, or of glucosyl sucrose and/or maltosyl sucrose, saccharose, fructose and glucose, iv) a mixture of at least 55% (w/w) lactosucrose, a maximum of 25% (w/w) lactose and a maximum of 10% (w/w) saccharose, v) a mixture of at least 88% (w/w) lactosucrose and a maximum of 10% (w/w) lactose and saccharose, vi) a mixture of 25% (w/w) glucosyl sucrose and/or maltosyl sucrose, between 48 and 56% (w/w) saccharose and not more than 10% (w/w) glucose and fructose, vii) a mixture of 18% (w/w) glucosyl sucrose and maltosyl sucrose, between 11 and 15% (w/w) saccharose and between 5 and 9% (w/w) glucose, viii) a sugar mixture named Nyuka-Oligo® LS40L (shortened to LS40L), Nyuka-Oligo® LS55L (shortened to LS55L), Nyuka-Oligo® LS55P (shortened to LS55P), Nyuka-Oligo® LS-90P (shortened to LS90P), Coupling Sugar® or Coupling Sugar S®, from the company Hayashibara Shoji, Inc., Japan.

The expression "oligosaccharide" or "polysaccharide" means polysaccharides which are built up out of at least three monomeric sugar molecules.

The expression "spray-dried powder formulation" or "dry powder formulation" means powder formulations which usually have less than about 10% (w/w) residual moisture, preferably less than 7% (w/w) residual moisture), less than 5% (w/w) residual moisture being particularly preferred and less than 3% (w/w) residual moisture being even more preferable. The residual moisture under constant spray-, vacuum- or freeze-drying conditions and with identical excipients depends essentially on the nature and content of the pharmaceutical active substance in the powder formulation.

The term "amorphous" means that the formulation in powder form contains less than 10% crystalline content, preferably less than 7%, more preferably less than 5%, less than 4, 3, 2 or 1% being particularly preferred.

The term "inhalable" means that the powders are suitable for pulmonary administration. Inhalable powders can be dispersed and inhaled with the aid of an inhalation device in such a way that the particles can reach the lungs and, if necessary, take systemic effect via the alveoli. Inhalable particles have, for example, a particle size of between 0.4 and 10 µm (MMD=mass median diameter) in most cases between 0.5 and 5 µm, preferably between 1 and 3 µm and/or a median aerodynamic particle diameter (MMAD=mass median aerodynamic diameter) of between 0.5 and 10 µm, preferably between 0.5 and 7.5 µm, more preferably between 0.5 and 5.5 µm, even more preferably 1-5 µm, between 1 and 4.5 µm being particularly preferred.

The expression "mass median diameter" or "MMD" is a measurement for the average particle size distribution, since the powders of the invention are generally polydispersed. The results are expressed as the diameter of the total volume distribution at 50% passage. The MMD values can be determined, for example, by means of laser diffractometry (see EXAMPLES section, Method), but of course, any other usual method can be used (e.g. electron microscopy, centrifugal sedimentation).

The term "mass median aerodynamic diameter" (MMAD) states the aerodynamic particle size at which normally 50% of the particles of the powder have a smaller aerodynamic diameter. In cases of doubt, the method stated in this patent document serves as the reference method for determining the MMAD (see EXAMPLES, Methods section).

The term "fine particle fraction" (FPF) describes the inhalable part of a powder comprising particles with a particle size of <5 µm MMAD. In readily inhalable powders the FPF is more than 20%, preferably more than 30%, more than 40% is particularly preferred, more than 50% is even more preferable and more than 55% is more preferable still. The term used in this connection, "cut-off diameter" states which particles are taken into account in the determination of the FPF. An FPF of 30% in the case of a cut-off diameter of 5 µm (FPF $_5$) means that at least 30% of all particles in the powder have a mass median aerodynamic diameter of less than 5 µm.

The term "spray solution" means aqueous solutions or suspensions in which to pharmaceutical active substance is dissolved/suspended together with at least one excipient.

The term "time of flight" is the name of a standard method of measurement as described in more detail in the EXAMPLES section. In a time of flight measurement the MMAD and FPF are determined simultaneously (see EXAMPLES, Methods section).

The term "pharmaceutically acceptable excipients", "carrier material" or "matrices" refers to excipients which may optionally be contained in the formulation within the limits of the invention. The excipients can, for example, be administered into the lungs without thereby having significantly unfavourable toxicological effects on the subject or the subject's lungs.

The expression "pharmaceutically acceptable salts" includes, for example, the following salts, but is not confined to them: salts from inorganic acids, such as chloride, sulphate, phosphate, diphosphate, bromide and nitrate salts. Also salts from organic acids, such as malate, maleate, fumarate, tartrate, succinate, ethylsuccinate, citrate, acetate, lactate, methanesulphonate, benzoate, ascorbate, para-toluenesulphonate, palmoate, salicylate and stearate, and estolate, gluceptate and lactobionate salts.

The term "pharmaceutically acceptable cations" includes, for example, without being confined to lithium, sodium, potassium, calcium, aluminium and ammonium (including substituted ammonium).

A "pharmaceutical active substance" is to be understood as a substance, a medicinal product, a composition or combination of such, which exerts a pharmacological, in most cases positive effect on an organism, organ and/or cell, when the active substance is brought into contact with the organism, organ or cell. When introduced into a patient, the effect can be local or systemic.

The term "biological macromolecule" means peptides, proteins, fats, fatty acids or nucleic acids.

The term "peptide" or "polypeptide" means polymers of amino acids comprising two to one hundred amino acid residues. The term peptide or polypeptide is used as a pseudonym and includes both homopeptides and heteropeptides, i.e., polymers of amino acids comprising identical or different amino acid residues. A "dipeptide" is thus built up of two peptide-linked amino acids; a "tripeptide" is built up of three peptide-linked amino acids. The term "protein" used here means polymers of amino acids with more than 100 amino acid residues.

The term "analogues" describes peptides/proteins in which single or several amino acids have been substituted, eliminated (e.g. fragments), added (e.g. derivatives with a C- or N-terminal extension) or otherwise modified from the native (wild type) sequence. Derivatization of the native protein, e.g. by sugar, polyethylene glycol or other, is also possible. Analogues have a bioactivity of at least 10, 20, 30 or 40%, preferably of at least 50, 60 or 70% and, particularly preferred, of at least 80, 90, 95, 100% or more than 100% of the bioactivity of the native, non-synthesized protein.

The expression "amino acid" means compounds which comprise at least one amino group and at least one carboxyl group. Although the amino group is usually in the α-position to the carboxyl group, any other arrangement in the molecule is also possible. The amino acid can also contain other functional groups, e.g. amino, carboxamide, carboxyl, imidazole, thio groups and other groups. Natural or synthetic amino acids, racemates or optical isomers (D or L), including different stereoisomeric proportions can be used. For example, the term isoleucine includes both D- isoleucine, L-isoleucine, racemic isoleucine and various ratios of the two enantiomers.

The expression "pure protein formulation" means spray-dried powders comprising one or several proteins and optionally a suitable buffer (typically from 0 to 15% (w/w) of the weight of the dry powder). The powder, by definition, does not contain any further excipients, i.e., the content of any further excipients is less than 1% (w/w) of the weight of the dry powder.

A "surfactant" substance is capable of lowering the surface tension of the solution in which it is dissolved. The surface-activity is measured, for example, by the tensiometer method as per Lecomte du Noüy (Bauer, Frömming, Führer, 6$^{th}$ Edition).

The expresion "oligosaccharide" or "polysaccharide" means polysaccharides which are built up out of at least three monomeric sugar molecules.

Powders According to the Invention

The present invention concerns powders, preferably spray-dried powders, containing a pharmaceutical active substance and a combination of excipients comprising at least one 1,4 O-linked saccharose derivative selected from the compounds: 1,4 O-linked D-Gal-saccharose (lactosucrose), 1,4 O-linked D-Glu-saccharose (glucosyl sucrose), or 1,4 O-linked Glu-saccharose (maltosyl sucrose) in combination with at least one further excipient. The other excipient is preferably an amino acid, a peptide and/or a mono-, di- and/or oligosaccharide, wherein the oligosaccharide may be a second 1,4 O-linked saccharose derivative, provided that this is different from the first.

According to a special embodiment of the invention, the corresponding powders contain as the excipient combination one or several mono-, di- and/or oligosaccharide(s) in addition to the 1,4 O-linked saccharose derivative, wherein the additional use of mono- and/or disaccharides is preferred. Examples of monosaccharides are fructose, maltose, galactose, glucose, D-mannose, sorbose and the like. Suitable disaccharides in terms of the invention are, for example, lactose, saccharose, trehalose, cellobiose, and the like. Particularly suitable oligo- or polysaccharides are raffinose, melezitose, dextrin, starch and the like. The invention therefore also includes corresponding powders with lactosucrose, lactose and saccharose, wherein the content of lactosucrose is $\geq 40\%$ (w/w), preferably $\geq 55\%$ (w/w), and also $\geq 88\%$ (w/w) of the total sugar content of the powder. According to a preferred embodiment, the powders according to the invention contain, in addition to the pharmaceutical active substance, a sugar mixture named Nyuka-Oligo® LS55P, or LS55P for short, from the company Hayashibara Shoji, Inc., Japan, which contains at least 55% lactosucrose, a maximum of 25% (w/w) lactose and a maximum of 10% (w/w) saccharose. According to another preferred embodiment, the powders according to the invention contain, in addition to the pharmaceutical active substance, a sugar mixture named Nyuka-Oligo® LS90P, or LS90P for short, from the company Hayashibara Shoji, Inc., Japan, which contains at least 88% lactosucrose and a maximum of 10% (w/w) lactose and saccharose.

Apart from these, powders comprising a combination of glucosyl sucrose and maltosyl sucrose have proved to be in accordance with the invention, again preferably in combination with further mono-, di- and/or polysaccharides. Therefore the present invention also includes corresponding powders which contain an excipient combination comprising glucosyl sucrose and maltosyl sucrose, saccharose, glucose and/or fructose, wherein the content of glucosyl sucrose and maltosyl sucrose is preferably 25% (w/w) or more, referred to the total sugar content of the powder. According to a more preferable embodiment, the respective content of glucosyl sucrose and maltosyl sucrose is at least 18% (w/w) of the total sugar content of the powder. According to a more preferable embodiment, the powders according to the invention contain, in addition to the pharmaceutical active substance, a sugar mixture named Coupling Sugar® from the company Hayashibara Shoji, Inc., Japan, which contains at least 18% (w/w) glucosyl sucrose and maltosyl sucrose, between 11 and 15% (w/w) saccharose and between 5 and 9% (w/w) glucose and between fructose. Furthermore, the present invention also concerns such powders which contain, in addition to the pharmaceutical active substance, a sugar mixture named Coupling Sugar S® from the company Hayashibara Shoji, Inc., Japan, which contains at least 25% (w/w) glucosyl sucrose and/or maltosyl sucrose, between 48 and 56% (w/w) saccharose and not more than 10% (w/w) glucose and fructose.

Furthermore, powders which contain as the excipient combination, in addition to at least one 1,4 O-linked saccharose derivative or a sugar mixture comprising at least one 1,4 O-linked saccharose derivative, amino acids, peptides, alcohols, polyols, non-biological and/or biological polymers as further excipients have proved to be in accordance with the invention. Further excipients known in the current state of the art which can be used according to the invention in combination with at least one 1,4 O-linked saccharose derivative or a sugar mixture comprising at least 1,4 O-linked saccharose derivative are, for example, lipids, fatty acids, fatty acid esters, steroids (e.g. cholesterol) or chelating agents (e.g., EDTA) and diverse cations. Excipients with a high glass transition temperature, for example, greater than 40° C., preferably greater than 45° C. or greater than 55° C. are particularly preferred. A list of suitable excipients can be found, for example, in Kippe (Eds.) "Handbook of Pharmaceutical Excipients", 3$^{rd}$ Ed., 2000.

Suitable protein-containing excipients are, for example, albumin (of human or recombinant origin), gelatines, casein, haemoglobin and the like. Sugar alcohols which can be considered for use as excipients are, in addition to mannitol, xylitol, maltitol, galactitol, arabinitol, adonitol, lactitol, sorbitol (glucitol), pyranosylsorbitol, inositol, myoinositol and the like. Suitable amino acids include, for example, alanine, glycine, arginine, histidine, glutamate, asparagine, cysteine, leucine, lysine, isoleucine, valine, tryptophan, methionine, phenylalanine, tyrosine, citrulline, L-aspartyl-L-phenylalanine methyl ester (=aspartame), trimethylammonioacetate (=betaine) and the like. Amino acids which act as buffers (e.g. glycine or histidine) and/or as dispersing agents are preferably used. The last groups include, in particular, predominantly hydrophobic amino acids, e.g., leucine, valine, isoleucine, tryptophan, alanine, methionine, phenylalanine, tyrosine, histidine, or proline. Within the context of the present invention, the use of isoleucine, in particular, in addition to the 1,4 O-linked saccharose derivative or a sugar mixture comprising at least one 1,4 O-linked saccharose derivative has proved advantageous, preferably in a concentration of 1 to 19.99% (w/w), 5 to 19.99% (w/w) being particularly preferred, 10 to 19.99% (w/w) being even more preferable.

The use of di-, tri-, oligo- or polypeptides which comprise one or several of these chiefly hydrophobic amino acids as a further excipient is also particularly advantageous. Particularly preferred are peptides with up to 20 amino acids, more preferably with up to 15 amino acids, even more preferably with up to 12 amino acids, even more preferably with up to 11 amino acids, even more preferably with up to 10 amino acids, even more preferably with up to 9 amino acids, even more preferably with up to 8 amino acids, even more preferably with up to 7 amino acids, even more preferably with up to 7, 6, 5, 4 or 3 amino acids. The peptides used for stabilization are not identical to the pharmaceutical active substance.

Suitable examples of tripeptides include, for example, one or several of the following tripeptides: Leu-Leu-Gly, Leu-Leu-Ala, Leu-Leu-Val, Leu-Leu-Leu, Leu-Leu-Met, Leu-Leu-Pro, Leu-Leu-Phe, Leu-Leu-Trp, Leu-Leu-Ser, Leu-Leul-Thr, Leu-Leu-Cys, Leu-Leu-Tyr, Leu-Leu-Asp, Leu-Leu-Glu, Leu-Leu-Lys, Leu-Leu-Arg, Leu-Leu-His, Leu-Gly-Leu, Leu-Ala-Leu, Leu-Val-Leu, Leu-Met-Leu, Leu-Pro-Leu, Leu-Phe-Leu, Leu-Trp-Leu, Leu-Ser-Leu, Leu-Thr-Leu, Leu-Cys-Leu, Leu-Try-Leu, Leu-Asp-Leu, Leu-Glu-Leu, Leu-Lsy-Leu, Leu-Arg-Leu and Leu-His-Leu. The use of tripeptides with the general formulas: Ile-X-X; X-Ile-X; X-X-Ile has proved particularly advantageous, wherein X can be one of the following amino acids: alanine, glycine, arginine, histidine, glutamic acid, glutamine, asparagine, aspartic acid, cysteine, leucine, lysine, isoleucine (Ile), valine, tryptophan, methionine, phenylalanine, proline, serine, threonine, tyrosine, L-aspartyl-L-phenylalanine-methyl ester (=aspartame), trimethylammonio-acetate. Particularly preferred are corresponding tripeptides with the formula (Ile)$_2$-X, for example, Ile-Ile-X, Ile-X-Ile, or X-Ile-Ile, wherein X can again be one of the above-listed amino acids. Among these are, for example, the tripeptides: Ile-Ile-Gly, Ile-Ile-Ala, Ile-Ile-Val, Ile-Ile-Ile, Ile-Ile-Met, Ile-Ile-Pro, Ile-Ile-Phe, Ile-Ile-Trp, Ile-Ile-Ser, Ile-Ile-Thr, Ile-Ile-Cys, Ile-Ile-Tyr, Ile-Ile-Asp, Ile-Ile-Glu, Ile-Ile-Lys, Ile-Ile-Arg, Ile-Ile-His, Ile-Gly-Ile, Ile-Ala-Ile, Ile-Val-Ile, Ile-Met-Ile, Ile-Pro-Ile, Ile-Phe-Ile, Ile-Trp-Ile, Ile-Ser-Ile, Ile-Thr-Ile, Ile-Cys-Ile, Ile-Try-Ile, Ile-Asp-Ile, Ile-Glu-Ile, Ile-Lys-Ile, Ile-Arg-Ile, Ile-His-Ile. The use of Ile-Ile-Ile is particularly advantageous.

Suitable polymers include, for example, the polyvinylpyrrolidones already mentioned above as excipients, derivatized celluloses, such as, e.g., hydroxymethyl, hydroxyethyl or hydroxypropyl-ethylcellulose, polymeric sugars such as e.g., Fiscoll, starches such as, e.g., hydroxyethyl or hydroxypropyl starch, dextrins such as, e.g., cyclodextrins (2-hydroxypropyl-β-cyclodextrin, sulphobutylether-β-cyclodextrin), polyethylenes, glycols and/or pectins.

The salts are, for example, inorganic salts such as chlorides, sulphates, phosphates, diphosphates, hydrobromides and/or nitrate salts. Furthermore, the powders according to the invention may also contain organic salts, such as, e.g., malates, maleates, fumarates, tartrates, succinates, ethylsuccinates, citrates, acetates, lactates, methanesulphonates, benzoates, ascorbates, para-toluenesulphonates, palmoates, salicylates, stearates, estolates, gluceptates or lactobionate salts. At the same time, corresponding salts may contain pharmaceutically acceptable cations, for example, sodium, potassium, calcium, aluminium, lithium or ammonium. Particularly preferred is the use of corresponding cations in connection with the stabilization of proteins. Accordingly the present invention concerns, according to a further embodiment, spray-dried powders which contain, in addition to the 1,4 O-linked saccharose derivative or sugar mixture comprising at least one 1,4 O-linked saccharose derivative and the pharmaceutical active substance, a pharmaceutically acceptable salt.

The powders according to the invention are, for example, spray-dried or freeze-dried powders, wherein spray-dried powders represent the preferred embodiment.

Powders, preferably freeze- or spray-dried powders which contain a pharmaceutical active substance and one of the above-stated excipient combination which contains at least one 1,4 O-linked saccharose derivative combined with at least one other excipient have proved particularly advantageous, wherein the content of excipient combination referred to the dry mass of the powder is between 25 and 99.99% (w/w), preferably between 40 and 99% (w/w), more preferably between 60 and 99% (w/w) and even more preferably between 60 and 90% (w/w), for example 25, 25.1, 25.2, 25.3 . . . 25.7, 25.8, 25,9 etc.; 26, 27, 28, 29, 30 etc.; 31, 32, 33, . . . 38, 39, 40 etc.; 41, 42, 43, . . . 48, 49, 50 etc. 51, 52, 53, . . . 58, 59, 60 etc.; 61, 62, 63, . . . 68, 69, 70 etc.; 71, 72, 73, . . . 78, 79, 80 etc.; 81, 82, 83, . . . 88, 89, 90 etc.; 91, 92, 93, . . . 98 etc. 99, 99.1, 99.2, 99.3, . . . 99.8, 99.9 etc. 99.91, 99.92, 99.93, . . . 99.98, 99.99% (w/w). In connection with the use of LS55P, a content of 80-90% (w/w) has proved particularly advantageous. Overall, the content of the excipient combination of at least one 1,4 O-linked saccharose derivative and one further excipient should be chosen in such a way that the powder is at least partially amorphous, preferably completely amorphous.

The content of pharmaceutical active substance referred to the dry mass of the powder according to the invention is usually between 0.01 and 75% (w/w), preferably between 0.01 and 50% (w/w), more preferably between 0.33 and 50% (w/w), even more preferably between 0.33 and 40% (w/w).

According to a more preferable embodiment, the content of pharmaceutical active substance referred to the solid content of the powder according to the invention is between 0.33 and 35% (w/w), preferably between 0.33 and 30% (w/w), more preferably between 0.33 and 25% (w/w) and even more preferably between 0.33 and 10% (w/w). The content is thus, for example, 0.01, 0.02, 0.03 . . . 0.08, 0.09 etc.; 0.1, 0.2, 0.3, . . . 0.8, 0.9 etc.; 1, 2, 3, . . . 8, 9, 10 etc.; 11, 12, 13, . . . 18, 19, 20 etc.; 21, 22, 23, . . . 28, 29, 30 etc.; 31, 32, 33, . . . 38, 39, 40 etc.; 41, 42, 43, . . . 48, 49, 50 etc.; 51, 52, 53, . . . 58, 59, 60 etc.; 61, 62, 63, . . . 68, 69, 70 etc.; 71, 72, 73, 74, 74.1, 74.2, 74.3 . . . , 74.8, 74.9 etc.; 74.91, 74.92, 74.93 . . . 74.98, 74.99, 75% (w/w).

Accordingly, powders with a ratio of excipient combination comprising at least one 1,4 O-linked saccharose derivative and a further excipient to pharmaceutical active substance of, for example 25/75, 26/74, 27/73, 28/72, 29/71, 30/70, 31/69, 32/68, 33/67, 34/66, 35/65, 36/64, 37/63, 38/62, 39/61, 40/60, 41/59, 42/58, 43/57, 44/56, 45/55, 46/54, 47/53, 48/52, 49/51, 50/50, 51/49, 52/48, 53/47, 54/46, 55/45, 56/44, 57/43, 58/42, 59/41, 60/40, 61/39, 62/38, 63/37, 64/36, 65/35, 66/34, 67/33, 68/32, 69/31, 70/30, 71/29, 72/28, 73/27, 74/26, 75/25, 76/24, 77/23, 78/22, 79/21, 80/20, 81/19, 82/18, 83/17, 84/16, 85/15, 86/14, 87/13, 88/12, 89/11, 90/10, 91/9, 92/8, 93/7, 94/6, 95/5, 96/4, 97/3, 98/2, 99/1, 99.1/0.9, 99.2/0.8, 99.3/0.7, 99.4/0.6, 99.5/0.5, 99.6/0.4, 99.66/0.33, 99.7/0.3, 99.8/0.2, 99.9/0.1, 99.99/0.01 (w/w) are in accordance with the invention. The content of excipient combination comprising at least one 1,4 O-linked saccharose derivative and a further excipient is preferably one of the values between 80 and 90% (w/w) referred to the dry mass of the powder.

Pharmaceutical active substances in the terms of the invention are, in addition to those which come under the general definition, inter alia antibiotics, antiviral agents, anepileptics, analgesics, anti-inflammatory agents or bronchodilators. Furthermore, they include active substances which, for example, act on the peripheral nervous system, on adrenergic receptors, cholinergic receptors, the skeletal muscle, the cardiovascular system, the smooth muscle, the circulation of the blood, on synaptic sites, neuro-effector connection sites, the endocrine system, the immune system, the reproductive system, the skeletal system, the autacoid system, the alimentary and excretory systems, the histamine system and the central nervous system. Suitable active substances further include, for example, hypnotics and sedatives, psychoactive energizers, tranquillizers, anticonvulsants, muscle relaxants, anti-parkinsonians, analgesics, anti-inflammatory agents, antimicrobial agents, hormonal active substances, such as contraceptives, sympathomimetics, diuretics, fat metabolism regulating agents, anti-androgenic agents, antiparasitics, neoplastic agents, antineoplastic agents and hypoglycaemic agents.

Furthermore, active substances which act on the respiratory system, for example against one of the following diseases: asthma, chronic obstructive pulmonary diseases (COPD), chronic bronchitis with emphysema, bronchopulmonary dysplasia (BPD), neonatal respiratory distress syndrome (RDS), bronchiolitis, croup, post-extubation stridor, pulmonary fibrosis, pneumonia or cystic fibrosis (CF) are exemplary under the term pharmaceutical active substance.

Representative examples of bronchodilators include, inter alia, beta-agonists, anticholinergics or methylxanthine. Examples of anti-inflammatory agents are steroids, cromolyn, nedocromil and leukotriene inhibitors. Examples of steroids include beclomethasone, betamethasone, biclomethasone, dexamethasone, triamcinolone, budesonide, butixocort, ciclesonide, fluticasone, flunisolide, icometasone, mometasone, tixocortol and loteprednol. Further examples are budesonide, fluticasone propionate, beclomethasone dipropionate, fometerol and triamcinolone acetonide.

Examples of antimicrobial agents are erythromycin, oleandomycin, troleandomycin, roxithromycin, clarithromycin, davercin, azithromycin, flurithromycin, dirithromycin, josamycin, spiromycin, midecamycin, leucomycin, miocamycin, rokitamycin, andazithromycin and swinolide A; fluoroquinolones, for example ciprofloxacin, ofloxacin, levofloxacin, trovafloxacin, alatrofloxacin, moxifloxicin, norfloxacin, eoxacin, grepafloxacin, gatifloxacin, lomefloxacin, sparfloxacin, temafloxacin, pefloxacin, amifloxacin, fleroxacin, tosufloxacin, prulifloxacin, irloxacin, pazufloxacin, clinafloxacin and sitafloxacin; aminoglycosides, such as, for example, gentamicin, vancomycin, teicoplanin, rampolanin, mideplanin, colistin, daptomycin, gramicidin, colistimethate; polymixins such as, for example, polymixin B, capreomycin, bacitracin; penems, pencillins including penicillinase-sensitive active substances such as penicillin G, penicillin V, penicillinase-resistant active substances such as methicillin, oxacillin, cloxacillin, dicloxacillin, floxacillin, nafcillin; substances which are active against gram-negative bacteria such as ampicillin, amoxicillin, hetacillin, cillin and galampicillin; antipseudomonal penicillins such as carbenicillin, ticarcillin, azlocillin, mezlocillin and piperacillin; cephalosporins such as cefpodoxime, cefprozil, ceftibuten, ceftizoxime, ceftriaxone, cephalothin, cephapirin, cephalexin, cephradrin, cefoxitin, cefamandole, cefazolin, cephaloridine, cefaclor, cefadroxil, cephaloglycine, cefuroxime, ceforanide, cefotaxime, cefatrizine, cephacetril, cefepime, cefixime, cefonizide, cefoperazone, cefotetan, cefinetazole, ceftazidime, loracarbef and moxalactam; monobactams such as aztreonam; and carbapenems such as, for example, imipenem, meropenem, pentamidine isethionate, aalbuterol sulphate, lidocaine, metaproterenol sulphate, beclomethasone dipropionate, triamcinolone acetamide, budesonide acetonide, fluticasone, ipratropium bromide, flunisolide, cromolyn sodium, ergotamine tartrate and where applicable, analogues, agonists, antagonists, inhibitors and pharmaceutically usable forms of salts and the like.

According to a further embodiment, the pharmaceutical active substance is a biological macromolecule. In keeping with the above-stated definitions, this term is to be understood to include, for example, peptides, proteins, fats, fatty acids or nucleic acids.

Biopharmaceutically significant proteins/polypeptides include, e.g., antibodies, enzymes, growth factors, e.g., steroids, cytokines, lymphokines, adhesion molecules, receptors and their derivatives or fragments, but are not confined to these. In general, all polypeptides which act as agonists or antagonists and/or can be used therapeutically or diagnostically are significant.

Suitable peptides or proteins in terms of the invention are, for example, insulin, insulin-like growth factor, human growth hormone (hGH) and other growth factors, tissue plasminogen activator (tPA), erythropoietin (EPO), cytokines, for example interleukins (IL) such as IL-1, IL-2, IL-3, IL-4, IL-5, IL-6, IL-7, Il-8, IL-9, Il-10, IL-11, IL-12, IL-13, IL-14, IL-15, IL-16, IL-17, IL-18, interferon (FN)-alpha, beta, gamma, omega or tau, tumour necrosis factors (TNF), such as, e.g., TNF-alpha, beta or gamma, TRAIL, G-CSF, CM-CSF, M-CSF, MCP-1 and VEGF. Further examples are monoclonal, polyclonal, multispecific and single chain antibodies and fragments thereof, such as, e.g., Fab, Fab', F(ab')$_2$, Fc and Fc' fragments, light (L) and heavy (H) immunoglobulin chains and their constant, variable or hypervariable regions and Fv and Fd fragments (Chamov et al., 1999, Antibody Fusion Proteins, Wiley-Liss Inc.). The antibodies can be of human or non-human origin. They include, for example, the classes known in humans: IgA, IgD, IgE, IgG and IgM, with their various subclasses, for example IgA1, IgA2 and IgG1, IgG2, IgG3 and IgG4. Humanized and chimaeral antibodies are also possible. Of particular therapeutic significance and hence the subject of the present invention are powder formulations which contain antibodies to, for example, various surface antigens such as CD4, CD20 or CD44 and various cytokines, for example IL2, IL4 or IL5. Further examples are antibodies to certain classes of immunoglobulin (e.g., anti-IgE antibodies) or to viral proteins (e.g., anti-RSV, anti-CMV antibodies, etc.).

Fab fragments (fragment antigen-binding=Fab) comprise the variable regions of both chains, which are kept together by the adjacent constant regions. Further antibody fragments are F(ab')$_2$ fragments, which can be produced by proteolytic digestion with pepsin. Shortened antibody fragments which comprise only the variable region of the heavy (VH) and the light (VL) chain can also be produced by gene cloning. These are known as Fv fragments (fragment variable=fragment of the variable part). Such antibody fragments are known as single chain Fv fragments (scFv). Examples of scFv antibodies are known and described: see, e.g., Huston et al., 1988, Proc. Natl. Acad. Sci. USA, 16, 5879ff.

In past years various strategies have been developed to produce multimeric scFv derivatives, such as, e.g. dia-, tri- and pentabodies. A "diabody" is what a specialist calls a bivalent homodimeric scFv derivative. The shortening of the peptide linker in the scFv molecule to 5-10 amino acids results in the formation of homodimers by overlapping of VH/VL chains. The diabodies can additionally be stabilized by inserted disulphide bridges. Examples of diabodies can be found in the literature, e.g. in Perisic et al., 1994 (Structure, 2, 1217ff). A "minibody" is what the specialist calls a bivalent, homodimeric scFv derivative. It comprises a fusion protein which contains the CH3 region of an immunoglobulin, preferably IgG, IgG1 being particularly preferred, as the dimerization region. This region connects the scFv fragments via a hinge region, also of IgG, and a linker region. Examples of such minibodies are described in Hu et al., 1996, Cancer Res., 56, 3055ff. A "triabody" is what the specialist calls a trivalent homotrimeric scFv derivative (Kortt et al., 1997, Protein Engineering, 10, 423ff). The direct fusion of VH-VL without the use of a linker sequence leads to the formation of trimers.

The fragments known to the specialist as mini-antibodies, which have a bi-, tri- or tetravalent structure, are also derivatives of scFv fragments. Multimerization for these is achieved via di-, tri- or tetrameric "coiled coil" structures (Pack, P. et al., 1993, Biotechnology, 11, 1271ff; Lovejoy, B. et al., 1993, Science, 259, 1288ff; Pack, P. et al., 1995, J. Mol. Biol., 246, 28ff).

A particularly preferred embodiment of the invention includes a protein of the antibody class, to be more exact, type 1 immunoglobulin G. This is a humanized monoclonal antibody with 95% human and 5% murine antibody sequences. The antibody has a molecular weight of about 148 kilodaltons (kDa), comprising two light and two heavy chains and a total of four disulphide bridges.

Particularly advantageous are powders, preferably freeze- or spray-dried powders which contain as the active substance a peptide or protein or a combination of peptide/peptide, peptide/protein or protein/protein. The corresponding biological macromolecules can make up 0.01 to 75% (w/w), preferably between 0.01 and 50% (w/w) of the dry mass of the powder. The content is thus, for example, 0.01, 0.02, 0.03 . . . 0.08, 0.09, 0.1, 0.2, 0.3 . . . 0.8, 0.9 etc.; 1, 2, 3, . . . 8, 9, 10 etc.; 11, 12, 13, . . . 18, 19, 20 etc.; 21, 22, 23, . . . 28, 29, 30 etc.; 31, 32, 33, . . . 38, 39, 40 etc.; 41, 42, 43, . . . 48, 49, 49.1, 49.2, 49.3, . . . 49.8, 49.9 etc.; 49.91, 49.92, 49.93, . . . 49.98, 49.99, 50% (w/w).

Particularly advantageous and in accordance with the invention are powders, preferably freeze- or spray-dried powders with a ratio of excipient combination comprising at least one 1,4 O-linked saccharose derivative and a further excipient to peptide/protein of 25/75, 26/74, 27/73, 28/72, 29/71, 30/70, 31/69, 32/68, 33/67, 34/66, 35/65, 36/64, 37/63, 38/62, 39/61, 40/60, 41/59, 42/58, 43/57, 44/56, 45/55, 46/54, 47/53, 48/52, 49/51, 50/50, 51/49, 52/48, 53/47, 54/46, 55/45, 56/44, 57/43, 58/42, 59/41, 60/40, 61/39, 62/38, 63/37, 64/36, 65/35, 66/34, 67/33, 68/32, 69/31, 70/30, 71/29, 72/28, 73/27, 74/26, 75/25, 76/24, 77/23, 78/22, 79/21, 80/20, 81/19, 82/18, 83/17, 84/16, 85/15, 86/14, 87/13, 88/12, 89/11, 90/10, 91/9, 92/8, 93/7, 94/6, 95/5, 96/4, 97/3, 98/2, 99/1, 99.1/0.9, 99.2/0.8, 99.3/0.7, 99.4/0.6, 99.5/0.5, 99.6/0.4, 99.66/0.33, 99.7/0.3, 99.8/0.2, 99.9/0.1, 99.99/0.01 (w/w).

If the powders according to the invention contain very small proteins/peptides with a molecular weight of <10 kDa, preferably <5 kDa, such as, for example, growth factors, for example cytokines, the content is preferably between 0.1 and 10% (w/w), more preferably between 0.2 and 5% (w/w) of the total weight of the powder. Accordingly powders are preferred whose cytokine content is 0.2, 0.3, 0.4 . . . 0.8, 0.9 etc.; 1, 2, 3, . . . etc.; 4.1, 4.2, 4.3, . . . 4.8, 4.9 etc.; 4.91, 4.92, 4.93, . . . 4.98, 4.99% (w/w).

If, however, the pharmaceutical active substance is one or several antibodies or a derivative thereof, the active substance content referred to the solid content of the powder is between 0.01 and 75% (w/w), between 0.01 and 50% (w/w) being preferred, preferably between 0.1 and 50% (w/w), more preferably between 0.33 and 50% (w/w), for example 0.1, 0.2, 0.3, 0.33, . . . 0.66, 0.7, 0.8, 0.9 etc.; 1, 2, 3, . . . 8, 9, 10 etc.; 11, 12, 13, . . . 18, 19, 20 etc.; 21, 22, 23, . . . 28, 29, 30 etc.; 31, 32, 33, . . . 38, 39, 40 etc.; 41, 42, 43, . . . 48, 49 etc.; 49.1, 49.2, 49.3, . . . 49.8, 49.9 etc.; 49.91, 49.92, 49.93, . . . 49.98, 49.99, 50 (w/w).

According to a special embodiment, the antibody content referred to the solid content of the powder is between 10 and 50% (w/w), more preferably between 10 and 30% (w/w), even more preferably between 10 and 20% (w/w). Particularly advantageous and in accordance with the invention are powders, preferably freeze- or spray-dried powders, with a ratio of excipient combination comprising at least one 1,4 O-linked saccharose derivative and a further excipient to antibody of 50/50, 51/49, 52/48, 53/47, 54/46, 55/45, 56/44, 57/43, 58/42, 59/41, 60/40, 61/39, 62/38, 63/37, 64/36, 65/35, 66/34, 67/33, 68/32, 69/31, 70/30, 71/29, 72/28, 73/27, 74/26, 75/25, 76/24, 77/23, 78/22, 79/21, 80/20, 81/19, 82/18, 83/17, 84/16, 85/15, 86/14, 87/13, 88/12, 89/11 or 90/10 (w/w).

According to a special embodiment, the present invention concerns powders, preferably freeze- or spray-dried powders, characterized in that the dry mass of the powder contains at least 25% (w/w), preferably between 55 and 99.99% (w/w), between 60 and 90% (w/w) being particularly preferred, content of a sugar mixture comprising at least one 1,4 O-linked saccharose derivative and up to 75% (w/w) content of a pharmaceutical active substance, wherein the content of lactosucrose, maltosyl sucrose and/or glucosyl sucrose is at least 20% (w/w) of the dry mass of the powder and the maximum sum of the weight percentages is 100% (w/w). A specialist is capable of preparing corresponding powders.

A specialist, for example, knows that, referred to the total solid content of the solution to be dried, he/she can mix in a maximum of 10% (w/w) pharmaceutical active substance if the content of the sugar mixture comprising at least 1,4 O-linked saccharose derivative is to be 90% (w/w).

The present invention also concerns corresponding powders, preferably freeze- or spray-dried powders, which contain, in addition to the pharmaceutical active substance, at least one 1,4 O-linked saccharose derivative or a sugar mixture comprising at least one 1,4 O-linked saccharose derivative and one or several pharmaceutically acceptable excipient(s) and/or one or several salt(s) as the excipient combination. Exemplary excipients are the above-mentioned amino acids, peptides and their salts, sugars, polyols, salts or organic acids and/or polymers.

According to a further embodiment, the present invention also concerns powders, preferably freeze- or spray-dried powders, which contain, in addition to the pharmaceutical active substance, at least one 1,4 O-linked saccharose derivative or a sugar mixture comprising at least one 1,4 O-linked saccharose derivative and one or several amino acid(s), preferably one amino acid, as the excipient combination. In this connection, the present invention concerns powders which contain, referred to their dry mass a) at least 25% (w/w), preferably between 50 and 90% (w/w), between 60 and 90% (w/w) being particularly preferred, content of a 1,4 O-linked saccharose derivative or a sugar mixture comprising at least one 1,4 O-linked saccharose derivative, b) between 1 and 19.99% (w/w) amino acids and c) between 0.01 and 74% (w/w) content of a pharmaceutical active substance, preferably a biological macromolecule, wherein the sum of the weight percentages can be a maximum of 100% (w/w). According to a preferred embodiment, the content of the 1,4 O-linked saccharose derivative or a sugar mixture comprising at least one 1,4 O-linked saccharose derivative is at least 60% (w/w), preferably between 70 and 90% (w/w) referred to the dry mass of the powder. In a corresponding formulation the content of amino acids is preferably between 1 and 19.99% (w/w) and the content of the pharmaceutical active substance is between 0.01 and 10% (w/w). The content of amino acids can also be increased to up to 40% (w/w). In these cases, the content of pharmaceutical active substance and/or the 1,4 O-linked saccharose derivative or a sugar mixture comprising at least one 1,4 O-linked saccharose derivative is to be reduced accordingly, so that the sum of the solid contents is a maximum of 100% (w/w). This applies particularly to the use of isoleucine as the amino acid.

Therefore the present invention, according to a further embodiment, also concerns powders, preferably freeze- or spray-dried powders, which contain or are composed of, for example, 80% (w/w) content of a 1,4 O-linked saccharose derivative or a sugar mixture comprising at least one 1,4 O-linked saccharose derivative/19% (w/w) amino acid/1% (w/w) pharmaceutical active substance (80/19/1); or, for example, (80/18/2); (80/17/3); (80/16/4); (80/15/5); (80/14/6); (80/13/7); (80/12/8); (80/11/9); (80/10/10); (70/20/10); (70/19/11); (70/18/12); (70/17/13); (70/16/14); (70/15/15); (70/14/16); (70/13/17); (70/12/18); (70/11/19); (70/10/20); (60/20/20); (60/19/21); (60/18/22); (60/17/22); (60/16/24); (60/15/25); (60/14/26); (60/13/27); (60/12/28); (60/11/29) or (60/10/30). If the active substance content, in the presence of a constant amino acid content of 20% (w/w), is reduced down as far as 0.01% (w/w), for example to 9.99, . . . 9.9, 9.8, 9.7 . . . 9.3, 9.2, 9.1 . . . 9, 8, 7, 6, 5, 4, 3, 2, 1, . . . 0.9, 0.8, 0.7, . . . 0.66, . . . 0.6, 0.5, 0.4, 0.3, 0.2, 0.1, 0.09, 0.08, 0.07, 0.06, 0.05, 0.04, 0.03, 0.02, 0.01% (w/w), the content of 1,4 O-linked saccharose derivative or the sugar mixture comprising at least one 1,4 O-linked saccharose derivative can be increased to, for example, 80.01, . . . 80.1, 80.2, 80.3 . . . 80.8, 80.9, 81, 82, 83, 84, 85, 86, 87, 88, 89, . . . 89.1, 98.2, 89.3 . . . 89.33, . . . 89.4, 89.5, 89.6, 89.7, 89.8, 89.9 . . . 89.91, 89.92, 89.93 . . . 89.97, 89.98, 89.99% (w/w), so that the sum of the weight contents of the individual constituents of the powder is 100% (w/w) referred to the dry mass of the powder. If further excipients or salts are added, the content of the 1,4 O-linked saccharose derivative or the sugar mixture comprising at least one 1,4 O-linked saccharose derivative, amino acids/peptides and/or pharmaceutical active substance can be adjusted/reduced accordingly, so that the weight contents of the individual constituents yield a sum of 100% (w/w).

Also in accordance with the invention are powders with the following composition: 79% (w/w) content of 1,4 O-linked saccharose derivative or a sugar mixture comprising at least one 1,4 O-linked saccharose derivative/11% (w/w) amino-acid/10% (w/w) pharmaceutical active substance (79/11/10); (78/12/10); (77/13/10); (76/14/10); (75/15/10); (74/16/10); (73/17/10); (72/18/10); (71/19/10); (70/20/10), wherein the content of pharmaceutical active substance can also be reduced from 10 to 0.01% (w/w), for example to 9.99 . . . 9.9, 9.8, 9.7 . . . 9.3, 9.2, 9.1 . . . 9, 8, 7, 6, 5, 4, 3, 2, 1, . . . 0.9, 0.8, 0.7, . . . 0.66, . . . 0.6, 0.5, 0.4, 0.3, 0.2, 0.1, 0.09, 0.08, 0.07, 0.06, 0.05, 0.04, 0.03, 0.02, 0.01% (w/w) and, accordingly, the content of the 1,4 O-linked saccharose derivative or a sugar mixture comprising at least 1,4 O-linked saccharose derivative can be increased to, for example, 80.01, . . . 80.1, 80.2, 80.3 . . . 80.8, 80.9, 81, 82, 83, 84, 85, 86, 87, 88, 89, . . . , 89.1, 89.2, 89.3 . . . 89.33 . . . 89.4, 89.5, 89.6, 89.7, 89.8, 89.9 . . . 89.91, 89.92, 89.93 . . . 89.97, 89.98, 89.99% (w/w), so that the sum of the weight contents is 100% (w/w) referred to the dry mass of the powder.

If the added amino acid is isoleucine, then according to a further embodiment, powders, preferably freeze- or spray-dried powders with a content of a) 1,4 O-linked saccharose derivative or a sugar mixture comprising at least one 1,4 O-linked saccharose derivative of at least 25% (w/w), preferably of 50 to 90% (w/w), 60 to 90% (w/w) being particularly preferred, b) a content of 1 to 19.99% (w/w) isoleucine and c) of a pharmaceutical active substance, preferably a peptide/protein, of at least 0.01% (w/w), preferably 0.01 to a maximum of 74% (w/w), are in accordance with the invention. Preferably the content of isoleucine is 5 to 19.99% (w/w), more preferably 10 to 19.99% (w/w) of the total solid content of the powder. Here too, the sum of the weight percentages of the individual constituents is not to exceed 100% (w/w). According to this, powders with the following composition are also in accordance with the invention: 80% (w/w) 1,4 O-linked saccharose derivative or sugar mixture comprising at least one 1,4 O-linked saccharose derivative/19% (w/w) isoleucine/1% (w/w) pharmaceutical active substance (80/19/1); 80/18/2); (80/17/3); (80/16/4); (80/15/5); (80/14/6); (80/13/7); (80/12/8); (80/11/9); (80/10/10); (70/19/11); (70/18/12); (70/17/13); (70/16/14); (70/15/15); (70/14/16); (70/13/17); (70/12/18); (70/11/19); (70/10/20); (60/19/21); (60/19/21); (60/19/21); (60/18/22); (60/17/23); (60/16/24); (60/15/25); (60/14/26); (60/13/27); (60/12/28); (60/11/29); (60/10/30). If further excipients or salts are added, the content of 1,4 O-linked saccharose derivative or a sugar mixture comprising at least one 1,4 O-linked saccharose derivative, isoleucine and/or pharmaceutical active substance is to be adjusted accordingly, so that the weight proportions of the individual constituents make up a total of 100% (w/w).

A further embodiment of the present invention concerns powders, preferably freeze- or spray-dried powders which, in addition to the pharmaceutical active substance, contain an excipient combination comprising at least one 1,4 O-linked saccharose derivative, or a sugar mixture comprising at least one 1,4 O-linked saccharose derivative, and one or several peptide(s), preferably one or several di- and/or tripeptide(s). The present patent document mentions some examples of tripeptides which can be used together with the 1,4 O-linked saccharose derivative or a sugar mixture comprising at least one 1,4 O-linked saccharose derivative for the preparation of powders in accordance with the invention. According to a special embodiment, the peptides, preferably the di- or tripeptides, are those which comprise at least one isoleucine residue, preferably two isoleucine residues, or according to an especially advantageous embodiment, three isoleucines.

In this connection powders are considered to be in accordance with the invention if they have a) a content of at least 25% (w/w), preferably between 60 and 99% (w/w), between 60 and 90% (w/w) being particularly preferred, of at least one 1,4 O-linked saccharose derivative or a sugar mixture comprising at least one 1,4 O-linked saccharose derivative, b) a content of peptide, preferably a di- or tripeptide, an isoleucine-containing peptide, for example tri-isoleucine, being particularly preferred, of 1 to 19.99% (w/w), c) 0.01 to a maximum of 74% (w/w) content of a pharmaceutically active substance, preferably a peptide/protein. Here too, the sum of the individual solids may not exceed 100% (w/w). The content of the peptide which is used as the excipient and is not identical to the pharmaceutical active substance may be increased to up to 40% (w/w). In these cases, the content of pharmaceutical active substance and/or the 1,4 O-linked saccharose derivative or a sugar mixture comprising at least one 1,4 O-linked saccharose derivative is to be reduced accordingly, so that the maximum sum of the proportions of solid constituents is 100% (w/w). This applies particularly to the use of di- or tripeptides, preferably tri-isoleucine.

Powders with the following composition are also in accordance with the invention: 89% (w/w) content of at least one 1,4 O-linked saccharose derivative or a sugar mixture comprising at least one 1,4 O-linked saccharose derivative/1% (w/w) peptide, preferably di- or tripeptide, more preferably an isoleucine-containing di- or tripeptide, tri-isoleucine being particularly preferred/10% (w/w) pharmaceutical active substance (89/1/10); (88/2/10); (87/3/10); (86/4/10); (85/5/10); (86/4/10); (83/7/10); (82/8/10); (81/9/10); (80/10/10); (79/11/10); (78/12/10); (77/13/10); (76/14/10); (75/15/10); (74/16/10); (73/17/10); (72/18/10) or (71/19/10), in which the content of the pharmaceutical active substance can also be reduced from 10 to 0.01% (w/w), for example to 9.99, . . . 9.9, 9.8, 9.7 . . . 9.3, 9.2, 9.1 . . . 9, 8, 7, 6, 5, 4, 3, 2, 1, . . . 0.9, 0.8, 0.7, . . . 0.66, . . . 0.6, 0.5, 0.4, 0.3, 0.2, 0.1, 0.09, 0.08, 0.07, 0.06, 0.05, 0.04, 0.03, 0.02, 0.01% (w/w) and the content of the 1,4 O-linked saccharose derivative or the sugar mixture comprising at least one 1,4 O-linked saccharose derivative can be increased accordingly to, for example, 80.01, . . . 80.1, 80.2, 80.3 . . . 80.8, 80.9, 81, 82, 83, 84, 85, 86, 87, 88, 89, . . . 89.1, 89.2, 89.3, . . . 89.33, . . . 89.4, 89.5, 89.6, 89.7, 89.8, 89.9, . . . 89.91, 89.92, 89.93, . . . 89.97, 89.99% (w/w), so that the sum of the weight proportions in relation to the dry mass of the powder is 100% (w/w). According to this, powders with the following composition are also in accordance with the invention: 80% (w/w) content of at least one 1,4 O-linked saccharose derivative or a sugar mixture comprising at least one 1,4 O-linked saccharose derivative/19% (w/w) peptide, preferably a di- or tripeptide, more preferably an isoleucine-containing di- or tripeptide, even more preferably tri-isoleucine/1% (w/w) pharmaceutical active substance (80/19/1); (80/18/2); (80/17/3); (80/16/4); (80/15/5); (80/14/6); (80/13/7); (80/12/8); (80/11/9); (80/10/10); (70/19/11); (70/18/12); (70/17/13); (70/16/14); (70/15/15); (70/14/16); (70/13/17); (70/12/18); (70/11/19); (70/10/20); (60/20/20); (60/19/21); (60/18/22); (60/17/23); (60/16/24); (60/15/25); (60/14/26); (60/13/27); (60/12/28); (60/11/29); (60/10/30), wherein the content of peptide, preferably a di- or tripeptide, more preferably an isoleucine-containing di- or tripeptide, even more preferably a tri-isoleucine can also be reduced from 10 to 1% (w/w), for example to 9.99, . . . 9.9, 9.8, 9.7 . . . 9.3, 9.2, 9.1 . . . 9, 8, 7, 6, 5, 4, 3, 2, 1.9, 1.8, 1.7, . . . 1.66, . . . 1.6, 1.5, 1.4, 1.3, 1.2, 1.1, 1% (w/w) and the content of pharmaceutical active substance, preferably peptide/protein, can be increased accordingly to, for example, 30.1, 30.2, 30.3 . . . 30.8, 30.9, 31, 32, 33, 34, 35, 36, 37, 38, 38.1, 38.2, 38.3, . . . 38.33, . . . , 38.4, 38.5, 38.6, 38.7, 38.8, 38.9, . . . 39% (w/w), so that the sum of the weight proportions in relation to the dry mass of the powder is 100% (w/w). If the peptide content, preferably di- or tripeptide, more preferably isoleucine-containing di- or tripeptide, even more preferably tri-isoleucine content is reduced from 10 to 1% (w/w), as presented here, the content of the 1,4 O-linked saccharose derivative or a sugar mixture comprising at least one 1,4 O-linked saccharose derivative in the powder can be increased. If there is, for example, a constant active substance content of 10% (w/w), powders can then be prepared with a content of 1,4 O-linked saccharose derivative or a sugar mixture comprising at least one 1,4 O-linked saccharose derivative of 80.1, 80.2, 80.3 . . . 80.8, 80.9, 81, 82, 83, 84, 85, 86, 87, 88, 88.1, 88.2, 88.3, . . . 88.33, . . . , 88.4, 88.5, 88.6, 88.7, 88.8, 88.9 or 89% (w/w).

According to a further embodiment according to the invention, the powders can additionally contain surfactants such as Tween 20, 40, 60 and 80, Brij 35, Pluronic F 88 and Pluronic F 127. These are used preferably in a concentration of 0.01-0.1% (w/w). Particularly preferred is a powder which contains as the excipient combination a 1,4 O-linked saccharose derivative or a sugar mixture comprising at least one 1,4 O-linked saccharose derivative and additionally Tween 20, preferably in a concentration of 0.01-0.1% (w/w), as a surfactant.

According to a further embodiment, the particles in the powders according to the invention have an MMD between 1 and 10 µm, preferably between 1 and 5 µm.

According to a further embodiment, the present invention concerns powders, preferably freeze- or spray-dried powders, with one of the compositions described here, which are characterized by a glass transition temperature greater than 40° C. Usually the corresponding powders according to the invention have a maximum glass transition temperature of about 96 to 110° C. However, in individual cases the value may be even higher.

Furthermore, the present invention also concerns pharmaceutical compositions which contain at least one of the powders according to the invention described here, preferably freeze- or spray-dried powders.

Preparation of the Powders According to the Invention:

The present invention also provides methods of preparing one of the powders described in more detail above, preferably a spray-dried or freeze-dried powder. The method is characterized in that a pharmaceutical active substance and an excipient combination containing at least one 1,4 O-linked saccharose derivative selected from the compounds: 1,4 O-linked D-Gal-saccharose (lactosucrose), 1,4 O-linked D-Glu-saccharose (glucosyl sucrose) or 1,4 O-linked Glu-Glu-saccharose (maltosyl sucrose) combined with at least one further excipient is mixed and dried under suitable conditions. The further excipient is preferably an amino acid, preferably isoleucine, a peptide, preferably a di- or tripeptide, and/or a mono-, di- and/or oligosaccharide, wherein the oligosaccharide can be a second 1,4 O-linked saccharose derivative, provided that this is different from the first.

In principle the powders according to the invention are prepared by dissolving the pharmaceutical active substance, preferably a biological macromolecule in the form of a peptide or protein, in an aqueous solution in dependence on the solubility conditions of the active substance in question. In most cases buffered solutions with a pH of 3-11, preferably from 3.5-9, are used. In the preparation of inhalable powders an aqueous solution with a pH of 4-7.8 is particularly advantageous. To ensure sufficient solubility, the pH of the solution should be below the pH of the peptide/protein and excipient. The aqueous solution can optionally contain additional water-soluble organic solvents, such as, e.g., acetone, alcohols or the like. Low alcohols such as, e.g., methanol, ethanol, propanol (n- or iso-propanol) or the like are particularly suitable. Such mixed solvent systems normally contain between 10 and 20% (v/v) content of a water-soluble organic solvent. The solid content of the solution to be dried is usually between 0.01 and 20% (w/w), preferably between 0.05 and 10% (w/w), between 0.1 and 5% (w/w) being particularly preferred. Within the limits of the present invention spray-dried and freeze-dried powders starting from an aqueous solution with a solid content of 10% (w/w) and spray-dried powders with a solid content of 3.33% (w/w) or 2% (w/w) were prepared.

Usually the excipient combinations, as described in examples above, are dissolved in a second container in ultra pure water or a suitable buffer solution with a pH of 3 to 11, preferably of 3.5 to 9, 4.0 to 7.8 being particularly preferred, and mixed in a second step with the active substance solution. Then the solution/suspension is adjusted to the desired solid content with ultra pure water or a suitable buffer solution with a pH of 3 to 11, preferably of 3.5 to 9, 4.0 to 7.8 being particularly preferred.

Therefore the present invention concerns a method of preparing a powder, characterized in that
a) a pharmaceutical active substance is dissolved/suspended in an aqueous solution/suspension;
b) an excipient combination of at least one 1,4 O-linked saccharose derivative selected from the compounds lactosucrose, glucosyl sucrose or maltosyl sucrose in combination with at least one further excipient is dissolved/suspended in an aqueous solution/suspension;
c) if the active substance and excipient combination of at least one 1,4 O-linked saccharose derivative in combination with at least one further excipient are dissolved/suspended in different solutions/suspensions, these are mixed;
d) the solution/suspension which contains the excipient combination of at least one 1,4 O-linked saccharose derivative combined with at least one further excipient and the pharmaceutical active substance is dried.

If the drying method is spray-drying, the drying under d) is performed by spraying the appropriate solution/suspension at a temperature below 200/120° C. (inlet/outlet temperature), preferably between 186/96° C. and 60/40°, for example at 180-150/95-80° C. The process is described in more detail on the basis of some examples in the "EXAMPLES" section.

The excipient combination containing at least one 1,4 O-linked saccharose derivative can also contain or comprise a sugar mixture which comprises at least one 1,4 O-linked saccharose derivative and a further sugar. Examples of correspondingly suitable sugar mixtures are described in more detail as examples in the "Definitions" section. The sugar mixtures may also comprise several different 1,4 O-linked saccharose derivatives, optionally in combination with further mono-, di- and/or oligosaccharides. Thus, within the limits of the invention, sugar mixtures, for example, with lactosucrose, lactose and saccharose can be used, wherein the content of lactosucrose in relation to the total sugar content is ≧40% (w/w), preferably ≧55% (w/w), or even ≧88% (w/w) or more. The sugar mixture is preferably a sugar mixture from the company Hayashibara Shoji, Inc., Japan, named Nyuka-Oligo® LS55P, or LS55P for short, which comprises at least 55% lactosucrose, a maximum of 25% (w/w) lactose and a maximum of 10% (w/w) saccharose. According to a further embodiment, the sugar mixture is a sugar mixture from the company Hayashibara Shoji, Inc., Japan, named Nyuka-Oligo® LS90P, or LS90P for short, which contains at least 88% lactosucrose and a maximum of 10% (w/w) lactose and saccharose. Furthermore, sugar mixtures made up of a combination of glucosyl sucrose and maltosyl sucrose can be used, again preferably in combination with further mono-, di- and/or polysaccharides. Therefore, in terms of the present invention, corresponding sugar mixtures made up of glucosyl sucrose and maltosyl sucrose, saccharose, glucose and/or fructose are suitable, wherein the content of glucosyl sucrose and maltosyl sucrose in relation to the total sugar content is preferably 25% (w/w) or more. According to a further embodiment, the respective content of glucosyl sucrose and maltosyl sucrose is at least 18% (w/w) of the total sugar content. According to a further preferred embodiment the sugar mixture used is a sugar mixture from the company Hayashibara Shoji, Inc., Japan, named Coupling Sugar®, which contains at least 18% (w/w) glucosyl sucrose and maltosyl sucrose, between 11 and 15% (w/w) saccharose and between 5 and 9% (w/w) glucose and fructose, respectively. Furthermore, in terms of the present invention, a sugar mixture from the company Hayashibara Shoji, Inc., Japan, which contains at least 25% (w/w) glucosyl sucrose and/or maltosyl sucrose, between 48 and 56% (w/w) saccharose and no more than 10% (w/w) glucose and fructose is suitable.

In keeping with the powders according to the invention described above, the solution/suspension to be dried additionally contains, according to a further embodiment, one or several pharmaceutically acceptable excipient(s) and/or one or several salt(s). The excipients are preferably amino acids, peptides, alcohols, polyols, and/or non-biological and/or biological polymers. Further excipients currently known in the prior art which can be used according to the invention in combination with at least one 1,4 O-linked saccharose derivative or a sugar mixture comprising at least one 1,4 O-linked saccharose derivative are, for example, lipids, fatty acids, fatty acid esters, steroids (e.g. cholesterol) or chelating agents (e.g., EDTA) and diverse cations. Particularly preferred are excipients with a high glass transition temperature, for example higher than 40° C., preferably higher than 45° C. or higher than 55° C. Examples of suitable excipients and excipient combinations can be found in this patent document in the section "Powders according to the invention". A further list of suitable excipients can be found, for example, in Kippe (Eds.) "*Handbook of Pharmaceutical Excipients*", $3^{rd}$ Ed., 2000.

The content of excipient combination comprising at least one 1,4 O-linked saccharose derivative in combination with at least one further excipient in the solution/suspension to be dried is between 25% and 99.99% (w/w), preferably between 60% and 99% (w/w), between 60 and 90% (w/w) being particularly preferred, referred to the solid content of the solution/suspension to be dried. The concentration of active substance is normally between 0.01 and 75% (w/w), preferably between 0.01 and 50% (w/w), more preferably between 0.33 and 50% (w/w), even more preferably between 0.33 and 40% (w/w). According to a more preferred embodiment, the content of pharmaceutical active substance referred to the solid content of the solution/suspension to be dried is between 0.33 and 35% (w/w), preferably between 0.33 and 30% (w/w), more preferably between 0.33 and 25% (w/w) and even more preferably between 0.33 and 10% (w/w).

Therefore the present invention also concerns methods of preparing a dried powder, preferably a freeze- or spray-dried powder, as described above, characterized in that the solid content of the solution/suspension to be dried contains between 25 and 99.99% (w/w), preferably between 60 and 90% (w/w) content of an excipient combination which comprises at least 1,4 O-linked saccharose derivative in combination with a further excipient. According to a more preferable embodiment, the present invention concerns a corresponding method, characterized in that the solid content of the solution/suspension to be dried contains a pharmaceutical active substance in a content of between 0.01 and 75% (w/w), preferably between 0.33 and 50% (w/w), between 0.33 and 30% (w/w) being particularly preferred.

According to a further embodiment of the present method, a solution/suspension with a solid content of a) at least 25% (w/w), for example between 25 and 99.99% (w/w) excipient combination comprising at least one 1,4 O-linked saccharose derivative in combination with at least one further excipient and b) at least 0.01% (w/w), preferably 0.01 to 75% (w/w) content of a pharmaceutical active substance, preferably a biological macromolecule, is prepared and dried, wherein the maximum sum of the weight percentages, referred to the solid content of the solution to be sprayed, is 100% (w/w). According to a preferred embodiment, a solution/suspension with a solid content a) of an excipient combination comprising at least one 1,4 O-linked saccharose derivative in combination with at least one further excipient of at least 60% (w/w), preferably between 60 and 90% (w/w), and b) 0.01 to 40% (w/w) content of a pharmaceutical active substance, preferably a biological macromolecule, is prepared and dried, wherein the maximum sum of the weight percentages of the solution or suspension, referred to the solid content of the solution to be sprayed, is 100% (w/w).

The solution/suspension to be dried preferably contains, in addition to the pharmaceutical active substance and at least one 1,4 O-linked saccharose derivative, a sugar mixture comprising further mono-, di- and/or oligosaccharides, and/or one or several amino acid(s) and/or peptide(s) or protein(s) as the further excipient, wherein the peptides or proteins used as the excipient are not identical to the pharmaceutical active substance. Therefore the present invention also concerns a method of preparing powders, characterized in that the solution/suspension to be dried contains, in relation to its solid content, a) at least 25% (w/w), preferably at least 60% (w/w) content of at least one 1,4 O-linked saccharose derivative or a sugar mixture comprising at least one 1,4 O-linked saccharose derivative, b) between 1 and 39.99% (w/w) content of at least one amino acid and/or at least one peptide and c) at least 0.01% (w/w) pharmaceutical active substance.

According to a more preferable embodiment, the solution/suspension to be dried contains, in addition to at least one 1,4 O-linked saccharose derivative or a sugar mixture comprising at least one 1,4 O-linked saccharose derivative, additionally one or several amino acid(s) as the further excipient. Solutions/suspensions are considered advantageous if their solid content has a) at least 25% (w/w), preferably 60 to 90% (w/w) content of at least one 1,4 O-linked saccharose derivative or a sugar mixture comprising at least one 1,4 O-linked saccharose derivative, b) 1 to 19.99% (w/w) amino acids, and c) at least 0.01% (w/w) content of a pharmaceutical active substance, preferably a peptide/protein, such as, for example, an antibody. The content of pharmaceutical active substance here is preferably 0.01 to a maximum of 74% (w/w), the maximum sum of the solids being 100% (w/w). A specialist is here in a position to prepare corresponding powders and to adjust the weight proportions in such a way that the sum of the solids does not exceed 100% (w/w). If the content of pharmaceutical active substance (referred to the total solid content) is to be, for example, 10% (w/w) and the content of at least one 1,4 O-linked saccharose derivative or a sugar mixture comprising at least one 1,4 O-linked saccharose derivative is to be 80% (w/w), the specialist then knows that he/she can add a maximum of 10% (w/w) amino acids to the solution/suspension to be sprayed.

According to a more preferable embodiment, the solution/suspension to be dried contains, in addition to at least one 1,4 O-linked saccharose derivative or a sugar mixture comprising at least one 1,4 O-linked saccharose derivative, isoleucine additionally as a further excipient. Solutions/suspensions are considered advantageous if their solid content has a) at least 25% (w/w), preferably 60 to 90% (w/w) content of at least one 1,4 O-linked saccharose derivative or a sugar mixture comprising at least one 1,4 O-linked saccharose derivative, b) 10 to 19.99% (w/w) isoleucine and c) at least 0.01% (w/w) content of a pharmaceutical active substance, preferably a peptide/protein, such as, for example, an antibody. The content of pharmaceutical active substance is here preferably 0.01 to a maximum of 65% (w/w), wherein the maximum sum of the solids is 100% (w/w). A specialist is here able to prepare corresponding powders and to adjust the weight proportions in such a way that the sum of the solids does not exceed 100% (w/w). If the content of pharmaceutical active substance (referred to the total solid content) is to be, for example, 10% (w/w) and the content of at least one 1,4 O-linked saccharose derivative or a sugar mixture comprising at least one 1,4 O-linked saccharose derivative is to be 80% (w/w), the specialist then knows that he/she can add a maximum of 10% (w/w) isoleucine to the solution/suspension to be sprayed.

According to a further embodiment, the solution/suspension to be dried contains, in addition to at least one 1,4 O-linked saccharose derivative or a sugar mixture comprising at least one 1,4 O-linked saccharose derivative, one or several peptide(s), preferably di- or tripeptide(s), isoleucine-containing tripeptides being particularly preferred, tri-isoleucine particularly preferred. Solutions or suspensions are considered advantageous if their solid content has a) at least 25% (w/w), preferably 60 to 99% (w/w), particularly preferred being 60 to 90% (w/w) content of at least one 1,4 O-linked saccharose derivative or a sugar mixture comprising at least one 1,4 O-linked saccharose derivative, b) 1 to 19.99% (w/w) content of a peptide, preferably a di- or tripeptide, tri-isoleucine being particularly preferred, and c) at least 0.01% (w/w) content of a pharmaceutical active substance, preferably a peptide/protein, such as, for example, an antibody, wherein the maximum sum of the solids is 100% (w/w). The content of the pharmaceutical active substance here is preferably 0.01 to a maximum of 74% (w/w). A specialist is here able to prepare corresponding powders and adjust the weight proportions in such a way that the sum of the solids does not exceed 100% (w/w). If the content of pharmaceutical active substance (referred to the total solid content) is to be, for example, 10% (w/w) and the content of at least one 1,4 O-linked saccharose derivative or a sugar mixture comprising at least one 1,4 O-linked saccharose derivative is to be 80% (w/w), the specialist then knows that he/she can add a maximum of 10%

(w/w) peptide, preferably a di- or tripeptide, tri-isoleucine being particularly preferred, to the solution/suspension to be sprayed.

As already mentioned, it is advantageous to prepare and spray solutions to be sprayed with a pH between 3 and 11, preferably between 3.5 and 9, between 4.0 and 7.8 being particularly preferred. Suitable buffer systems are known to the specialist. Usually the use of inorganic or organic salts as the buffer system proves particularly advantageous.

Typically, the optimal content of excipient and protein is determined experimentally for each protein or peptide. Preferred formulations of the invention can additionally contain one further excipient to improve powder properties such as dispersibility and flow, with maintenance of a superior inhibition of aggregation.

Spray-drying:

The spraying is performed in conventional spray-dryers, for example in instruments manufactured by Niro A/S (Soeborg, Denmark), Büchi Labortechnik GmbH (Flawil, Switzerland) or the like. The optimal conditions for spray-drying depend on the formulation concerned and are to be determined experimentally. Air is typically used as the gas, but inert gases such as nitrogen or argon are also suitable. Furthermore, the spray-drying temperature, meaning inlet and outlet temperature, are determined by the temperature sensitivity of the active substance used, in dependence on the stabilizers used. An inlet temperature of 50-200° C. is usual, whereas the outlet temperature is in most cases 30-150° C. Within the context of the present invention, work was done with an inlet temperature of about 170-185° C. and an outlet temperature of 80-100° C. However, an inlet temperature of up to 200° C., preferably 60-185° C. and an outlet temperature of up to 120° C., preferably 40-105° C., depending on the stabilizer content, is also possible. As a rule, the spraying is performed at a pressure of about 20-150 psi, preferably at about 30 or 40 to 100 psi, for example at about 30, 40, 50, 60, 70, 80, 90 or 100 psi.

With regard to the Büchi B290 spray dryer, the liquid feed rate is normally between 0.1 and 100 ml/min, preferably between 0.1 and 30 ml/min, for example, about 3 ml/min. In this connection an aspirator flow rate of 20-40 m$^3$/h, preferably of 30-40 m$^3$/h, such as, for example, 35 m$^3$/h and an atomizing air flow of 0.3-2.5 m$^3$/h preferably 30-40 m$^3$/h, such as, for example, about 0.67 m$^3$/h, 1.05 m$^3$/h and 1.74 m$^3$/h, has proved particularly suitable.

The spray-dried powders can optionally undergo a second gentle drying (final drying). The aim is to obtain a uniform residual water content in the powder, preferably less than 2% (w/w) and thus to improve the stability of the active substance and also powder properties such as glass transition temperature, flow and dispersibility. The conditions of the final drying process must be chosen to avoid significantly reducing the bioactivity of the pharmaceutical active substance. The spray-dried active substance powder formulations are preferably prepared, processed further and stored under dry conditions (at low relative humidity). The process of final drying makes it possible to reduce the moisture content of the powders even further, despite relatively high baseline residual water contents after spray-drying. Surprisingly, in the preferred formulations, the excipients which are the subject matter of the invention are superior in stabilizing the proteins even when the processing and storage conditions are not optimal.

Freeze-drying:

The freeze-drying of aqueous solutions is performed in accordance with the description in Essig, Oschmann: "Lyophilisation", Wissenschaftliche Verlagsgesellschaft, Stuttgart (1993). The therapeutic active substance is usually freeze-dried as an aqueous solution or suspension. Suitable concentrations and pHs are to be observed. In a preferred formulation, the pharmaceutical active substance is first dissolved in an aqueous solution with a suitable buffer system. The pH of the protein-containing solutions is generally from 3 to 11, preferably from 3.5 to 9, between 4.0 and 8 being particularly preferred. The pH of the solution must be adjusted to be either below or above the isoelectric point of the active substance. In a second container, the excipient or a mixture of suitable excipients is dissolved in ultra pure water or a suitable buffer solution with a pH of 3 to 11, preferably 3.5 to 9, 4.0 to 8.5 being particularly preferred, and in a second step, mixed with the protein solution. Finally the solution is adjusted to the desired solid content with ultra pure water or a suitable buffer solution with a pH of 3 to 11, preferably 3.5 to 9, 4.0 to 8.5 being particularly preferred. Suitable total solid contents are between 0.1 and 30% (w/w), preferably 0.5 to 20% (w/w), between 0.75 and 15.0% (w/w) being particularly preferred.

The solutions are then freeze-dried in a conventional standard commercial freeze-dryer, such as the Christ LPC-16/NT Epsilon 2-12 D from the company Martin Christ Gefriertrocknungsanlagen GmbH, or another freeze dryer. The product is a protein-containing powder or cake which is then comminuted with a suitable method before further processing, so that a polydisperse powder is obtained.

The temperatures in the freeze-dryer are optimized experimentally and are generally between −70° C. and +100° C., preferably between −50° C. and +40° C. Preferred parameters for pressure in the freeze-dryer are from 10*e-5 to 1013 mbar. The freeze-dried protein formulations can preferably be subject to a second gentle drying (final drying) after their comminution. The aim is to maintain a uniform residual water content of the formulations of less than 2% and thus to improve both the stability of the active substance and the powder properties, such as glass transition temperature, flow and dispersibility. The conditions of the final drying process must be chosen to avoid significantly reducing the activity of the active substance.

Properties of the Spray-dried Dry Powder Formulations

The dry protein powder formulations prepared within the context of this invention have a residual water content of below 15% (w/w), usually of below 10% (w/w) and preferably of below 6% (w/w). More preferably, the spray-dried protein powder formulations have a residual water content of below 5% (w/w), below 3% (w/w) being particularly preferred and between 0.2 and 2.0% (w/w) being most preferred. Formulations with low residual moisture generally show improved stability during packaging and storage. Furthermore, the dry protein powder formulations of the invention are mainly hygroscopic, i.e., they tend to absorb moisture from their environment. To avoid this, such powders are usually stored in containers such as blister packs from which air humidity is excluded. Surprisingly, it emerged with selected formulations of the powders according to the invention, that the powders remained stable with regard to both protein stability and inhalability even during open storage for one month at 43% relative humidity.

The stabilizing effects of the excipients described here are capable of protecting the protein against the extreme stresses during spray-drying and storage. Pure protein formulations spray-dried in the absence of excipients form aggregates to a great extent. Process-related factors such as heat, shearing stress and denaturation at the air-water interfaces cause aggregation (up to about 6.6% aggregates) during spray-drying and subsequent final drying (up to about 5.8% aggregates). During storage, massive aggregate formation (of about 11.8 to about 18.9% aggregates) results from the absence of the stabilizing hydrate shell of the proteins.

The preferred spray-dried formulations of the invention, in contrast with the pure protein formulations, are able both to reduce the formation of aggregates after spray-drying and to keep aggregate formation at a very low level during storage under various conditions. In the preferred formulations only about 0.5 to about 1.8% aggregates form as a result of spray-drying and subsequent vacuum drying, in contrast to up to about 4.0% aggregates in pure protein formulations.

Under particularly challenging storage conditions (40° C., 75% relative humidity), forced storage stability, the preferred formulations (aggregates of about 1.0 to about 13.1%) show distinct superiority to pure protein formulations (about 18.2 to 18.9% aggregates) and to an analogous reference formulation with trehalose as the excipient.

This advantage is particularly apparent in the comparison of the formulation described in Example 4. The addition of tri-isoleucine in the solution to be sprayed leads to a significant improvement of the aerodynamic properties of the powders. Surprisingly, only the combinations which contain at least one 1,4 O-linked saccharose derivative and tri-isoleucine, especially LS55P and tri-isoleucine and LS90P and tri-isoleucine are capable of protecting the pharmaceutical active substance, a protein, for example, being present, from aggregate formation (only 0.7 to 4.4% aggregates). Neither the excipients used in combination with tri-leucine, described in WO01/32144, raffinose (12.6% aggregates) and hydroxyethyl starch (about 18.6% aggregates) nor trehalose, which is described in the latest technological literature as an outstanding stabilizer, is/are able, in combination with tri-isoleucine, to protect the protein under the particularly challenging conditions. Both the LS55P-tri-isoleucine formulations and the LS90P-tri-isoleucine formulations show a distinct advantage over a saccharose-tri-isoleucine formulation (5.6% aggregates) and a saccharose-lactose-tri-isoleucine formulation (8.8% aggregates). This is all the more surprising in that, besides saccharose, up to 25% lactose is also present in LS55P. It is evident that the negative effect of the reducing sugar lactose on protein stability is overcompensated in LS55P by the lactosucrose contained in it. A higher proportion of lactosucrose in the sugar content of the powder formulations is even more advantageous to protein stability (see LS90P formulations).

Formulations which already have a significantly stabilizing effect on the incorporated proteins during relatively short storage under particularly destabilizing conditions (1 week at 40° C., 75% relative humidity) also stabilize proteins in the long term under far milder standard storage conditions (e.g. 1 year dry, about 25° C.).

After equilibration with subsequent storage for four weeks under dry conditions at 40° C. (equilibrated storage stability), the powder formulations containing LS55P and Coupling Sugar are distinguished by low aggregate contents (about 1.4 to 3.2% aggregates), especially in comparison to pure protein powders (about 11.8% aggregates).

After vacuum drying with subsequent storage for four weeks under dry conditions at 40° C. (vacuum dried storage stability), the powder formulations containing LS55P and Coupling Sugar are distinguished by low aggregate contents (about 1.1 to 2.1% aggregates), especially in comparison to pure protein powders (about 13.2% aggregates).

LS55P (80%), isoleucine (10%) and IgG1 (10%) formulations with a fine particle fraction of about 35%, after vacuum drying with subsequent decanting under nitrogen, aggregate contents below 1.9% after storage for three months under dry conditions at 2 to 8° C., 25° C. and 40° C.

LS55P (80%), tri-isoleucine (10%) and IgG1 (10%) formulations with an MMAD of about 3.9 μm and a fine particle fraction of 58.3% after spray-drying show, after vacuum drying with subsequent decanting under nitrogen, aggregate contents below 1.9% after storage for three months under dry conditions at 2 to 8° C. and after storage under dry conditions at 40° (3 month stability) they show aggregate contents below 2.6%.

Furthermore, the above-mentioned LS55P (80%), tri-isoleucine (10%) and IgG1 (10%) formulations also show a low aggregate content (about 1.3%) with an approximately equal low MMAD (about 3.8 μm) and equally high fine particle fraction (about 59.6%) after open storage for one month at about 43% relative humidity and 25° (open 1 month stability).

LS90P (90%) and IgG1 (10%) formulations with an MMAD of about 3.8 μm, an MMD of about 2.8 μm and a fine particle fraction of about 24% after spray-drying show, after vacuum drying with subsequent decanting under nitrogen, aggregate contents below 1.2 and 2.2%, respectively, after storage for one month and three months under dry conditions at 2 to 8° C., 25° C. and 40° C. (1 and 3 month stability).

LS90P (80%), isoleucine (10%) and IgG1 (10%) formulations with a fine particle fraction of about 28% show, after vacuum drying with subsequent decanting under nitrogen, aggregate contents below 0.9 and 1.1%, respectively, after storage for one month and three months under dry conditions at 2 to 8° C., 25° C. and 40° C. (1 and 3 month stability).

LS90P (80%), tri-isoleucine (10%) and IgG1 (10%) formulations with an MMAD of about 4.8 μm and a fine particle fraction of 53.2% after spray-drying show, after vacuum drying with subsequent decanting under nitrogen, aggregate contents below 1.2 and 2.3%, respectively, after storage for one month and three months under dry conditions at 2 to 8° C., 25° C. and 40° C. (1 and 3 month stability).

Furthermore, variations of the above-named LS90P (80%), tri-isoleucine (10%) and IgG1 (10%) formulations also show low aggregates between about 0.5% and 0.8% after open storage for one month and three months at about 43% relative humidity and 25° C. (open 1 and 3 month stability). After spray-drying the MMADs are between about 3.9 μm and 3.3 μm and the FPFs are between about 55.6% and 58.9%. After open storage for one month at about 43% relative humidity and 25° C., the above-named formulations also show small MMADs (about 4.1 to 3.5 μm) and a high fine particle fraction (about 62.3 to 67.3%).

Variation of the spray-drying conditions makes it possible to produce powders which preferably have a mass median diameter (MMD) of less than 20 μm, preferably less than 10 μm. According to a particularly preferred embodiment, these particles according to the invention have a mass diameter of less than 7.5 μm, preferably less than 5 μm. Particles with a mass diameter of less than 4 μm are particularly preferred, less than 3.5 μm being more preferable. In general, particles with a mass diameter of 0.1-5 μm, preferably 0.2-4 μm can also be produced. In a further embodiment, non-inhalable particles, e.g., lactose, with a particle size of at least 40 μm, preferably between 40 and 200 μm, are added to the relevant powders. The content is preferably at least 15%, more preferably at least 20%, even more preferably at least 30%, even more preferably at least 40%, at least 50 or 60% being particularly preferred.

Besides the mass median diameter (MMD), inhalability depends to a considerable extent on the mass median aerodynamic diameter (MMAD). The particles according to the invention preferably have an MMAD of less than 10 μm and, more preferably, less than 7.5 µm. Powders comprising particles with an MMAD of less than 5.5 µm, preferably less than 5 µm, even more preferably less than 4.5 µm, are particularly advantageous. The powders described in the examples can be produced with the appropriate particle sizes by the combination of optimal spray-drying conditions and choice and concentration of excipients in accordance with the invention. The addition of amino acids and/or tripeptides, in particular, leads to improved particle performance with an increased content of inhalable particles with an MMAD of less than 7.5 µm, preferably less than 5.5 µm. Addition of isoleucine or tri-isoleucine makes it possible to prepare inhalable powders with an FPF greater than 28%, preferably greater than 40%, more preferably greater than 50% and even more preferably, greater than 55% (see "EXAMPLES").

The powders according to the invention are, moreover, distinguished by a glass transition temperature of at least 40° C., preferably at least 50° C., more preferably at least 55° C., even more preferably at least 60° C. Particularly preferred powders have a glass transition temperature of at least 65° C. In general, the glass transition temperature of the powders according to the invention is 40 to 110° C. Therefore the present invention also concerns powders, preferably spray-dried powders, containing a pharmaceutical active substance and LS90P, LS55P, Coupling Sugar or Coupling Sugar S, wherein the glass transition temperature is 40° C. or more, preferably between 45 and 60° C. or higher. According to a more preferred embodiment, the glass transition temperature is 55° C. or more, preferably between 55 and 60° or higher.

Freeze-dried Powders:

Powders can alternatively be prepared by freeze-drying with subsequent pulverization (see examples). In the examples illustrated here, the pulverization was performed as simply as possible with a spatula in the lyophilization vials. The lyophilate can also, of course, be pulverized with suitable mills such as a cutting mill, a ball mill, a pinned disk mill, a grinding mill, an air stream mill or other suitable methods (see Bauer, Frömming, Führer, 6$^{th}$ Edition).

Properties of the Freeze-dried Powders:

The dry protein powder formulations prepared within the context of this invention have a residual water content below 15% (w/w), usually below 10% (w/w) and preferably below 5% (w/w). More preferably, the spray-dried protein powder formulations have a residual water content of below 5% (w/w), below 3% (w/w) being particularly preferred and between 0.2 and 1.5% (w/w) being most preferred. Formulations with low residual moisture generally show improved stability during packaging and storage. Furthermore, the dry protein powder formulations of the invention are mainly hygroscopic, i.e., they tend to absorb moisture from their environment. To avoid this, such powders are usually stored in containers such as blister packs from which air humidity is excluded.

The stabilizing effects of the excipients described here are capable of protecting the protein against the extreme stresses during freeze-drying and storage. Pure protein formulations freeze-dried in the absence of excipients form aggregates to a great extent. Process-related factors such as freezing stress, concentration, pH shift and denaturation at the air-water interfaces cause aggregation (up to about 2.1% aggregates) during freeze-drying. During storage, massive aggregate formation (20.5% aggregates) results from the absence of the stabilizing hydrate shell of the proteins.

The preferred freeze-dried formulations of the invention, in contrast with the pure protein formulations, are able both to reduce the formation of aggregates after freeze-drying and to keep aggregate formation at a very low level during storage under various conditions. Under particularly challenging storage conditions (40° C., 75% relative humidity), forced storage stability, the freeze-dried and pulverized lyophilates in the preferred formulations (aggregates of about 1.2 to about 1.5%) prove distinctly superior to pure protein formulations (about 14.5% aggregates) and to an analogous reference formulation with mannitol as the excipient (about 34.0% aggregates).

Formulations which already have a significantly stabilizing effect on the incorporated proteins during relatively short storage under particularly destabilizing conditions (1 week at 40° C., 75% relative humidity) also stabilize proteins in the long term under far milder standard storage conditions (e.g. 1 year dry, about 25° C.).

After freeze-drying, pulverization and equilibration with subsequent storage for four weeks under dry conditions at 40° C. (equilibrated storage stability), the powder formulations containing LS55P and Coupling Sugar are distinguished by low aggregate contents (about 2.6 and 4.6% aggregates), especially in relation to pure protein powders (about 15.3% aggregates) and to an analogous reference formulation with mannitol as the excipient (about 11.6% aggregates).

After freeze-drying, pulverization and vacuum drying with subsequent storage for four weeks under dry conditions at 40° C. (vacuum dried storage stability), the powder formulations containing LS55P and Coupling Sugar are distinguished by low aggregate contents (about 1.2 and 1.5% aggregates), especially in relation to pure protein powders (about 14.5% aggregates) and to an analogous reference formulation with mannitol as the excipient (about 6.2% aggregates).

The powders according to the invention are, moreover, distinguished by a glass transition temperature of at least 40° C., preferably at least 50° C., more preferably at least 55° C. In general, the glass transition temperature of the powders according to the invention is 40 to 110° C., but in individual cases it can even exceed this value. Therefore the present invention also concerns powders, preferably freeze-dried and pulverized powders, containing a pharmaceutical active substance and LS90P, LS55P, Coupling Sugar or Coupling Sugar S, wherein the glass transition temperature is 40° C. or more, preferably between 45 and 60° C. or higher. According to a more preferred embodiment, the glass transition temperature is 55° C. or more, preferably between 55 and 60° or up to 110° C.

Use of the Dried Powder

The powders according to the invention are suitable for the preparation of a medicinal product, preferably for the preparation of a medicinal product for inhalation.

Administration of the Powders According to the Invention

In principle, the powder formulations according to the invention can be administered directly as a dry powder be means of so-called dry powder inhalers or after suspension or reconstitution in the form of aerosols via so-called nebulizers. The powders for inhalation according to the invention can by administered by means of inhalers currently known in the prior art.

Powders for inhalation according to the invention can, for example, be administered via inhalers which administer a single dose from a store by means of a measuring chamber as described in U.S. Pat. No. 4,570,630A or by means of other apparatus, such as described in DE 36 25 685 A. The powders for inhalation according to the invention are preferably decanted into capsules (to make so-called inhalettes/aerocaps), which are put into inhalers, such as, for example, those described in WO 94/28958, for use.

Further examples of suitable inhalers can be found in, inter alia, U.S. Pat. No. 5,458,135; U.S. Pat. No. 5,785,049 or WO 01/00263. Further suitable inhalers are known from WO 97/41031; U.S. Pat. No. 3,906,950 and U.S. Pat. No. 4,013,075. Further dispersion inhalers for dry powder formulations are described in EP 129 985; EP 472 598; EP 467 172 and U.S. Pat. No. 5,522,385.

The powders for inhalation according to the invention can be administered, for example, by means of the inhaler known under the name Turbohaler® (AstraZeneca LP) or inhalers such as are presented, for example, in EP 237 507. Other suitable inhalers are the Rotahaler® or the Discus® (both by GlaxoSmithKline Corp.), the Spiros™ Inhaler (Dura Pharmaceuticals) and the Spinhaler® (Fiscon).

An inhaler particularly preferred for the administration of the drug combination according to the invention in inhalettes/aerocaps is shown in FIG. 24. This inhaler (Handihaler) for the inhalation of drugs in powder form from capsules is characterized by a housing 1, containing two windows 2, a deck 3 in which there are air inlets and which is provided with a filter 5 fixed by a filter housing 4, an inhalation chamber 6 connected to deck 3, provided with a trigger 9 with two ground pins 7, which moves against a spring 8, and a mouthpiece 12 connected in a hinged manner by a spindle 10 to the housing 1, the deck 3 and a cap 11, and air inlet shutters 13 to adjust the flow resistance.

If the powders for inhalation according to the invention are to be decanted into capsules (inhalettes/aerocaps) in the sense of the aforementioned preferred application, charges of 1 to 30 mg per capsule are available.

The powders according to the invention can also be administered as propellant-containing or propellant-free aerosols for inhalation. For this, the powders according to the invention are suspended in pressure-liquefiable solvents or solvent mixtures or reconstituted in an aqueous solution. Suitable suspensions or solutions are currently known in the prior art. For example, reconstitution in physiological solutions with a pH of 3-11, preferably of 4-9, is advantageous. Reconstitution in an aqueous solution with a pH of 5.5-7.8 is particularly advantageous. The propellant-containing suspensions or solutions for reconstitution of the powders according to the invention can also contain further excipients in the form of stabilizers, emulsifiers, surfactants and/or water-soluble organic solvents. Appropriate substances are known to the specialist and examples are described in Bauer: Lehrbuch der Pharmazeutischen Technologie (Wissenschaftl. Verlagsgesellschaft mbH, Stuttgart), pp. 178-184; Adler, 1988, Journal of Pharmaceutical Sciences, 88(2), pp. 199-208. Corresponding aerosols for inhalation which are produced by suspending or reconstituting the powders according to the invention are also the subject matter of the present invention.

The propellants which can be used to produce the aerosols for inhalation according to the invention are also currently known in the prior art. Suitable propellants are selected from the group comprising hydrocarbons such as n-propane, n-butane or isobutene and halogenated hydrocarbons such as, preferably, chlorinated and fluorinated derivatives of methane, ethane, propane, butane, cyclopropane or cyclobutane. The aforementioned propellant gases can be used singly or in mixtures of the same. Particularly preferred propellant gases are halogenated alkane derivatives selected from TG11, TG12, TG134a (1,1,1,2-tetrafluoroethane), TG227 (1,1,1,2,3,3,3-heptafluoropropane) and mixtures of the same, wherein the propellant gases TG134a, TG227 and mixtures of the same are preferred.

The propellant-containing aerosols for inhalation according to the invention can contain up to 5% (w/w) active substance. Aerosols according to the invention contain, for example, 0.002-5% (w/w), 0.01-3% (w/w), 0.015-2% (w/w), 0.1-2% (w/w), 0.5-2% (w/w) or 0.5-1% (w/w) pharmaceutical active substance. Aerosols for inhalation with a corresponding active substance concentration can be adjusted to solvents by targeted reconstitution of the powders according to the invention in an appropriate quantity.

The aforementioned propellant-containing aerosols for inhalation according to the invention can be administered by means of inhalers currently known in the prior art (MDIs=metered dose inhalers). Reference is made here to the examples Ventolin® (Ventolin Pharmacy) and the inhalers described in U.S. Pat. No. 5,32,094 and U.S. Pat. No. 5,672,581. Accordingly, a further aspect of the present invention concerns medicinal products in the form of propellant-containing aerosols as described in the foregoing in combination with one or several inhaler(s) suitable for the administration of these aerosols. The present invention also concerns inhalers, characterized in that they contain propellant-containing aerosols according to the invention as described in the foregoing.

The present invention also concerns cartridges which, equipped with a suitable valve, can be used in a suitable inhaler and which contain one of the aforementioned propellant-containing aerosols for inhalation according to the invention. Suitable cartridges and methods for filling these cartridges with the propellant-containing aerosols for inhalation according to the invention are currently known in the prior art.

The powders according to the invention can also be reconstituted in propellant-free solutions for inhalation or suspensions. Appropriate propellant-free solutions for inhalation contain, for example, aqueous or alcoholic, preferably ethanolic, in some cases a mixture of ethanolic and aqueous solvents. In the case of aqueous/ethanolic solvent mixtures, the ethanol content relative to the water content is not limited, but the upper limit is preferably 70% (v/v) ethanol, up to 60% (v/v) ethanol being particularly preferred. The remaining volume percentage is made up by water. Co-solvents and/or other excipients, as described above, can be added to the propellant-free solutions for inhalation according to the invention. For example, co-solvents which contain hydroxyl groups or other polar groups, such as, e.g., alcohols, can be used—especially isopropyl alcohol, glycols—especially propylene glycol, polyethylene glycol, polypropylene glycol, glycol ether, glycerol, polyoxyethylene alcohols and polyoxyethylene fatty acid esters. In this connection, the terms excipient and additive mean any pharmacologically acceptable substance which is not an active substance, but can be formulated with the active substance(s) in the pharmacologically suitable solvent to improve the qualitative properties of the active substance formulation. These substances preferably display no pharmacological action or none worth mentioning within the context of the intended therapy or, at least, no undesirable pharmacological action. The excipients and additives include, together with those listed above, e.g. surfactants, such as, e.g., soya lecithin, oleic acid, sorbitan esters, such as polysorbates, polyvinylpyrrolidone, other stabilizers, sequestrants, antioxidants and/or preservatives which ensure or prolong the period for which the finished drug formulation can be used, flavourings, vitamins and/or other additives currently known in the prior art. The additives also include pharmacologically acceptable salts such as, for example, sodium chloride, as isotonic agents. The preferred excipients include antioxidants, such as, for example, ascorbic acid, unless already used to adjust the pH, vitamin A, vitamin E, tocopherols and similar vitamins occurring in the human body or provitamins. Preservatives can be used to protect the formulation from contamination with micro-organisms. Suitable preservatives are those currently known in the prior art, especially cetylpyridinium chloride, benzalkonium chloride or benzoic acid or benzoates such as sodium benzoate in the concentration currently known in the prior art. The aforementioned preservatives are preferably contained in concentrations of up to 50 mg/100 ml, between 5 and 20 mg/100 ml being particularly preferred. Accordingly, the present invention also includes propellant-free aerosols for inhalation which are produced by reconstitution of the powders according to the invention.

For the administration of the propellant-free solutions for inhalation according to the invention, particularly suitable inhalers are those which can nebulize a small quantity of a liquid formulation in the therapeutically necessary dosage into an aerosol suitable for therapeutic inhalation within a few seconds. Within the context of the present invention, nebulizers are preferred in which a quantity of active substance solution less than 100 µl, preferably less than 50 µl, between 10 and 30 µl being particularly preferred, can be nebulized with preferably one squeeze into an aerosol with a particle size of less than 20 µm, preferably less than 10 µm, in such a way that the inhalable part of the aerosol is already equal to the therapeutically effective quantity.

Such a device for the propellant-free administration of a metered dose of a liquid drug for use by inhalation is, for example, described in detail in the international patent application WO 91/14468 and also in WO 97/12687 (especially in FIGS. 6a and 6b there). Reference is expressly made within the context of the present invention to the relevant FIGS. 6a and 6b of WO 97/12687, including their descriptions. The nebulizers (devices) described there are known under the name Respimat® (Boehringer Ingelheim Pharma). Owing to its cylindrical shape and a handy size of less than 9 to 15 cm in length and 2 to 4 cm in breadth, this device can be carried by the patient at all times. The nebulizer sprays a defined volume of the drug formulation with use of high pressures through small nozzle holes, so that inhalable aerosols result.

The preferred nebulizer essentially comprises an upper housing, a pump housing, a nozzle, a tension locking mechanism, a spring housing, a spring and a substance container/refill, characterized by
- a pump housing which is fixed in the upper housing and which bears at one end a nozzle head with the nozzle or nozzle system,
- a hollow plunger with valve body,
- a driving flange in which the hollow plunger is fixed and which is contained in the upper housing,
- a tension locking mechanism which is contained in the upper housing,
- a spring housing with the spring inside it, which is mounted on a pivot bearing in the upper housing so as to be pivotable,
- a lower housing which is fitted onto the spring housing in the axial direction.

The hollow plunger with valve body corresponds to a device presented in WO 97/12687. It extends in part into the cylinder of the pump housing and is positioned in the cylinder in such a way that it can be moved in the axial direction. Particular reference is made within the context of the present invention to the FIGS. 1-4—especially FIG. 3—and the parts of the description which apply to them. The hollow plunger with the valve body exerts, on its high-pressure side, at the time of release of the spring, a pressure of 5 to 60 Mpa (about 50 to 600 bar), preferably 10 to 60 Mpa (about 100 to 600 bar) on the fluid, the metered active substance solution. In this, volumes of 10 to 50 microlitres are preferred, volumes of 10 to 20 microlitres are particularly preferred and a volume of 15 microlitres per squeeze is quite particularly preferred.

The valve body is preferably mounted on the end of the hollow plunger which faces towards the nozzle head.

The nozzle in the nozzle head is preferably microstructured, i.e. is manufactured by microtechnology. Microstructured nozzle heads are presented, for example, in WO 94/07607; reference is hereby made to the content of that document, especially to FIG. 1 and its description presented there. The nozzle head comprises, e.g., two plates made of glass and/or silicon, closely connected with each other, at least one of which has one or several microstructured channel(s) which connect(s) the nozzle inlet side with the nozzle outlet side. On the nozzle outlet side is at least one round or non-round aperture 2-10 µm in depth and 5-15 µm in breadth, the depth being preferably 4.5 to 6.5 micrometres and the length preferably 7-9 micrometres. In the case of several nozzle holes, two being preferred, the directions of the streams of the nozzle jets may be parallel with each other or may be inclined towards each other in the direction of the nozzle hole. In the case of a nozzle head with at least two nozzle holes on the outlet side, the directions of the stream may be inclined towards each other at an angle of 20-160°, an angle of 60-150° being preferred, 80-100° being particularly preferred. The nozzle holes are preferably separated by a distance of 10-200 µm, a distance of 10-100 µm being more strongly preferred, 30-70 µm being particularly preferred. 50 µm is most strongly preferred.

The directions of the stream accordingly meet in the vicinity of the nozzle holes.

The liquid drug formulation hits the nozzle head at an entry pressure of up to 600 bar, preferably 200 to 300 bar, and is nebulized through the nozzle holes into an inhalable aerosol. The preferred particle or droplet sizes of the aerosol are up to 20 µm, preferably 3-10 µm.

The tension locking mechanism contains a spring, preferably a cylindrical screw-shaped compression spring, as a store of mechanical energy. The spring acts on the driving flange as a return mechanism whose movement is determined by the position of a blocking element. The path of the driving flange is kept within precise limits by an upper and a lower catch. The spring is preferably bent via an energy-converting gear, e.g. a screw-push gear, by an external rotary momentum which is created by rotating the upper housing against the spring housing in the lower housing. In this case, the upper housing and the driving flange contain a single- or multi-thread wedge gear.

The blocking element with meshing blocking surfaces is arranged in a ring shape around the driving flange. It comprises, e.g., a radially elastically deformable ring made of plastic or metal. The ring is in one plane perpendicular to the nebulizer axis. After the spring has been bent, the blocking surfaces of the blocking element push themselves into the path of the driving flange and prevent the release of the spring. The blocking element is set in action by a trigger. The trigger is connected with or coupled to the blocking element. To set the tension locking mechanism in action, the trigger is pushed so as to be parallel to the plane of the ring, preferably into the nebulizer; in this process the deformable ring is warped in the ring plane. Design details of the tension locking mechanism are described in WO 97/20590.

The lower housing is pushed over the spring housing in the axial direction and covers the bearing, the spindle drive and the substance container/refill for the fluid.

When the nebulizer is activated, the upper housing is rotated against the lower housing, the lower housing taking the spring housing with it. The spring is pressed together by means of the screw-push gear and bent and the tension locking mechanism locks in automatically. The angle of rotation is preferably an integer which is a fraction of 360°, e.g., 180°. At the same time as the bending of the spring, the drive component in the upper housing is displaced by a set distance, the hollow plunger is pulled back within the cylinder in the pump house, whereby a part of the fluid from the substance container/refill is sucked into the high-pressure space in front of the nozzle.

If required, several consecutive exchangeable substance containers/refills containing the fluid to be nebulized can be inserted into the nebulizer and used. The substance container/refill contains the aqueous aerosol formulation according to the invention.

The nebulizing process is initiated by light pressure on the trigger. The locking mechanism then clears the way for the driving component. The bent spring pushes the plunger into the cylinder of the pump housing. The fluid comes out of the nozzle of the nebulizer in nebulized form.

Further design details are presented in the PCT applications WO 97/12683 and WO 97/20590, to the content of which reference is hereby made.

The components of the nebulizer (atomizer) are made of a material suitable for their function. The housing of the nebulizer and—as far as the function permits—other components are preferably made of plastic, e.g., by injection moulding. For medical purposes physiologically acceptable materials are used.

In FIGS. 6 a/b of WO 97/12687 including their description, to the content of which reference is again made at this point, a corresponding nebulizer (Respimat®) is described. This is particularly suitable for the administration of the propellant-free aerosols for inhalation according to the invention.

FIG. 6a of WO 97/12687 shows a longitudinal section through the nebulizer when the spring is bent, FIG. 6b of WO 97/12687 shows a longitudinal section through the nebulizer when the spring is released: The upper housing (51) contains the pump housing (52), on the end of which the holder (53) of the nebulizer nozzle is mounted. In the holder are the nozzle head (54) and a filter (55). The hollow plunger (57) fixed in the driving flange (56) of the tension locking mechanism extends in part into the cylinder of the pump housing. At its end, the hollow plunger carries the valve body (58). The hollow plunger is sealed off with the seal (59). Within the upper housing is the catch (60) which the driving flange adjoins when the spring is released. At the driving flange is the catch (61) which the driving flange adjoins when the spring is bent. After the spring is bent, the blocking element (62) pushes itself between the catch (61) and a support (63) in the upper housing. The trigger (64) is connected to the blocking element. The upper housing ends in the mouthpiece (65) and is closed with the removable protective cap (66). The spring housing (67) with compressed spring (68) is fitted onto the upper housing in such a way as to be pivotable, by means of the snap catches (69) and pivot bearing. The lower housing (70) is pushed over the spring housing. Within the spring housing is the exchangeable substance container/refill (71) for the fluid to be nebulized (72). The substance container/refill is closed with the stopper (73) through which the hollow plunger plunges into the substance container/refill and dips its end into the fluid (store of active substance solution). In the shell of the spring housing is the spindle (74) for the mechanical meter. At the end of the spindle which faces the upper housing is the drive pinion (75). On the spindle is the rider (76).

If the formulation according to the invention is nebulized by means of the technology described in the foregoing (Respimat®), the mass of the output of at least 97%, preferably at least 98% of all activations of the inhaler (squeezes) should correspond to a defined quantity with a maximum tolerance range of 25%, preferably 20% of this quantity. Between 5 and 30 mg formulation per squeeze is preferred as the defined mass of the output and between 5 and 20 mg is particularly preferred.

However, the formulation according to the invention may also be nebulized by means of inhalers other than those described in the foregoing, for example jet stream inhalers or other hospital ward nebulizers.

Accordingly, a further aspect of the present invention concerns medicinal products in the form of propellant-free solutions or suspensions for inhalation as described in the foregoing in association with a device suitable for the administration of these formulations, preferably in association with the Respimat®. Preferably the present invention is aimed at propellant-free solutions or suspensions for inhalation containing one of the powders according to the invention in association with the device known under the name of Respimat®. The present invention further concerns devices for inhalation mentioned in the foregoing, preferably the Respimat®, characterized in that they contain propellant-free solutions or suspensions for inhalation described in the foregoing.

According to the invention, solutions for inhalation containing one of the powders described according to the invention described here, contained in a single dosage form, are preferred.

Besides the solutions and suspensions envisaged in the foregoing for administration in the Respimat®, the propellant-free solutions for inhalation or suspensions according to the invention can be present as concentrates or sterile ready-to-use solutions or suspensions for inhalation. Ready-to-use formulations can be generated from the concentrates, for example, by the addition of isotonic saline solutions. Sterile ready-to-use formulations can be administered by means of energy-driven standing or portable nebulizers which create inhalable aerosols by means of ultrasound or compressed air by the Venturi principle or other principles.

Accordingly, a further aspect of the present invention concerns medicinal products in the form of propellant-free solutions or suspensions for inhalation as described in the foregoing, which are present as concentrates or sterile ready-to-use formulations, in association with a device suitable for the administration of these solutions, characterized in that this device is an energy-driven standing or portable nebulizer which creates inhalable aerosols by means of ultrasound or compressed air by the Venturi principle or other principles.

Other suitable nebulizers for the administration by inhalation of reconstituted aerosols are the AERx™ (Aradigm), the Ultravent® (Mallinkrodt) and the Aconll® (Maquest Medical Products).

EXAMPLE Of EMBODIMENTS

Material and Methods

Materials

A humanized monoclonal antibody with a molecular weight of about 148 kDa from Boehringer Ingelheim, Germany, was used as the IgG1. The antibody is derived from a murine antibody in which the complementarity determining regions of the murine antibody have been transferred onto a human immunoglobulin framework. The result is a chimaeral antibody with 95% human and 5% murine content. The antibody is expressed from murine myeloma cell lines. The cells are removed with the aid of tangential flow microfiltration and the cell-free solution is cleaned up by various chromatography methods. Further steps include nuclease treatment, treatment at low pH and nanofiltration. The bulk solution containing the antibodies contains histidine 25 mM and glycine 1.6 mM as a buffer and was concentrated by diafiltration to about 100 mg/ml for the preparation of the solution for spray-drying. The bulk for the preparation of the solution to be sprayed had 0.4 to 0.8% aggregates. The finished medicinal product can be kept for at least 2 years at 2-8° C. Nyuka-Oligo® LS55P, Nyuka-Oligo® LS90P, Coupling Sugar® and Coupling Sugar S® were obtained from Hayashibara Shoji, Inc., Japan. Saccharose, lactose, mannitol, raffinose, hydroxyethyl starch and L-isoleucine were obtained from Sigma-Aldrich Chemie GmbH, Germany. Trehalose came from Georg Breuer GmbH, Germany. Tri-isoleucine was obtained from Iris Biotech GmbH, Germany.

Hen's egg albumin lysozyme (lysozyme), 135500 U/mg, was obtained from SERVA Electrophoresis GmbH, Germany. Synthetic salmon calcitonin (calcitonin) was obtained from Biotrend Chemikalien GmbH, Germany.

Spray-drying with Büchi B-290

The spray-drying was performed with the aid of a B-290 Büchi Mini Spray Dryer supplied by Büchi Labortechnik GmbH. The formulations were spray-dried essentially in accordance with the description in "Spray Drying Handbook", 5$^{th}$ Edition, K. Masters, John Wiley and Sons, Inc., NY, N.Y. (1991):

The spray-dryer is made up of a heating system, a filter, an aspirator, a drying cylinder, a cyclone, temperature sensors to measure the inlet and outlet temperature and a separator. With the aid of a peristaltic pump, the solution to be sprayed is pumped into a two-fluid nozzle. There the solution is atomized into small drops by means of compressed air. It is dried in the spray cylinder with warmed air which is sucked through the spray cylinder by an aspirator in a co-current stream. The product is caught in the separator after passing through the cyclone.

Two different cyclones were used:
Cyclone I: Büchi Cyclone (Product Number 4189)
Cyclone II: Büchi High-performance Cyclone (Product Number 46369)

The solid content in the sprayed solutions was 10% (w/v), 3.33% and 2.00% in 50 to 600 ml. The inlet temperature was about 170 to 185° C., the liquid feed rate about 3 to 3.33 ml/min, the aspirator flow rate about 36.8 to 38.3 m$^3$/h and the atomizing air flow (AAF) was about 0.67 m$^3$/h, 1.05 m$^3$/h and 1.74 m$^3$/h. This results in an outlet temperature of about 80-95° C.

Freeze-drying

The freeze-drying was performed with the aid of a Christ LPC-16/NT Epsilon 2-12 D freeze-drying system from the company Martin Christ Gefriertrocknungsanlagen GmbH. The freeze-drying system comprises the drying chamber, a condenser to separate the sublimated solvent, a pump to create the vacuum and the electrical equipment. The drying is controlled by the tray temperature and the vacuum of the dry chamber.

The solid content of the freeze-drying solution was 5% (w/v). The solution was divided into 2R vials each containing 0.5 ml and placed in the freeze-drying system with standard freeze-drying stoppers. First the solutions were frozen at −40° C. in 30 minutes. The second step was the main drying at 0.11 mbar in three stages. First 30 hours at −40° C., then 8 hours at −30° C. and finally 8 hours at −16° C. The next step was the final drying process and this was performed for 20 hours at 20° C. and 0.001 mbar. Finally the vials were automatically sealed with the freeze-drying stoppers, which initially were only placed in the vials. The lyophilates obtained in this way were pulverized within the vials by means of a spatula.

X-ray Diffractometry (Wide-angle X-ray Scattering= WAXS):

To determine the crystallinity of the dried samples, the samples were tested with a Seifert XRD 3000 TT X-ray diffractometer (Seifert, Ahrensburg, Germany) in a room with a controlled temperature of 22° C. The Cu anode, Cu-Kα ray X-ray tube with λ=0.15418 mm (Ni primary filter) was operated at an anode voltage of 40 kV and a current of 30 mA. After placing of the sample plate in the instrument, the sample was scanned in the range of 5 to 40° at a scan rate of 2 θ=0.05° with a measurement time of 2 seconds at each angle.

The powder diffractograms were recorded on the SC 1000 V detector with the ScanX-Rayflex application, version 3.07, device XRD 3000 (scan) or the Rayflex Version 2.1, 1996 (analysis).

Size Exclusion Chromatography (SEC-HPLC)

a) IgG1 Protein Aggregates

To quantify IgG1 protein aggregates in the reconstituted powders, SEC-HPLC was performed. The SEC-HPLC was performed with an HP1090 from the company Agilent. For separation, a TSK3000SWXL column (300×7.8 mm) from the company Tosoh Biosep (Tosoh Bioscience, Stuttgart, Germany) was used. For the mobile phase a buffer of 0.1 M disodium hydrogen phosphate dihydrate and 0.1 M sodium sulphate was dehydrated and adjusted to pH 6.8 with 85% ortho-phosphoric acid. The applied quantity of sample was 25 μl with a protein concentration of 2-10 mg/ml. The protein was detected at 280 nm with the aid of a diode array detector from the company Agilent. The software HP-Chemstation from the company Agilent was used to evaluate the chromatograms.

b) Calcitonin Protein Aggregates

To quantify calcitonin protein aggregates in the reconstituted powders, SEC-HPLC was performed. The SEC-HPLC was performed with an HP 1100 from the company Agilent. A TSK2000SWXL column (300×7.8 mm) from the company Tosoh Biosep (Tosoh Bioscience, Stuttgart, Germany) was used for the separation. A buffer of 0.25 sodium sulphate with a pH of about 6 was used as the mobile phase (Windisch et al. 1997). Alternatively a buffer of 0.1M disodium hydrogen phosphate dihydrate and 0.1M sodium sulphate, dehydrated and adjusted to pH 6.8 with 85% ortho-phosphoric acid, can be used. The applied quantity of sample was 20 μl with a protein concentration of 0.5-2 mg/ml. The protein was detected at 210 nm with the aid of an Agilent UV detector. The software HP-Chemstation from the company Agilent was used to evaluate the chromatograms.

c) Residual Lysozyme Monomer Content

To quantify the residual lysozyme monomer content in the reconstituted lysozyme formulations, a modified SEC-HPLC method (van de Weert, 2000) was performed. The SEC-HPLC was performed with an Agilent HP1100. A TSK2000SWXL column (300×7.8 mm) from the company Tosoh Biosep (Tosoh Bioscience, Stuttgart, Germany) was used for the separation. For the mobile phase a buffer of 0.05 M disodium hydrogen phosphate dihydrate and 0.2 M sodium chloride was adjusted to pH 7.0 with 85% ortho-phosphoric acid. The applied quantity of sample was 25 μl with a protein concentration of 2-10 mg/ml. The protein was detected at 280 nm with the aid of an Agilent UV detector. The software Agilent Chemstation from the company Agilent was used to evaluate the chromatograms.

To evaluate the formulations, the remaining soluble monomer was quantified by the following method: First a calibration line was drawn by means of standard lysozyme solutions with concentrations of 2.5 mg/ml, 5.0 mg/ml and 10 mg/ml. For this, the AUC of the monomer peaks was considered in relation to the corresponding lysozyme concentrations in the tested standard solutions. The residual monomer content of the different lysozyme formulations tested is calculated on the basis of the calibration line. The higher the residual monomer content of a formulation, the better the protein stability.

Particle Size Determination (MMD)

The mass median diameter or the median particle size of the particles was determined with the aid of the Sympatech Helos from the company Sympatech GmbH (Clausthal-Zellerfeld, Germany). The measurement principle is based on laser deflection and a helium-neon laser is used. 1-3 mg powder is dispersed at an air pressure of 2 bar and brought in front of the Fourier lens (50 mm) by a parallel laser beam. The particle size distribution is evaluated with a Fraunhofer model. Two measurements were performed per powder.

Mass Median Aerodynamic Diameter (MMAD) and Fine Particle Fraction (FPF)

12-18 mg powder was decanted into hard gelatine capsules (size 3) and introduced into the HandiHaler (powder inhaler from the company Boehringer Ingelheim) for each measurement. The HandiHaler was attached to the USP EP/throat of the impactor inlet of the measurement instrument by means of an adaptor and the powder was released at 39.0 l/min with a suction time of 6.15 seconds. The air flow was controlled by an external control board. At least three capsules were measured for each powder.

With the APS 3321 from the company TSI Inc., MN, USA in combination with the 3306 impactor inlet, the aerodynamic particle size (MMAD) and the fine particle fraction (FPF) were determined simultaneously, the MMAD by a "time of flight" determination and the FPF by means of a single-stage impactor (effective cut-off diameter at 39 l/min: 5.0 µm). After release, the powder is transported via the EP/USP throat or sample induction port to reach a thin capillary, where 0.2% of the powder is removed under isokinetic conditions for the time of flight measurement. The time of flight measurement is performed after transit through the capillary by means of 2 laser beams which record the times of flight for a defined distance in analogy with a light barrier. The result obtained is a count distribution which is then converted to a mass distribution and thence to the mass median aerodynamic diameter (MMAD).

The remaining 99.8% of the powder which has been passed through in the capillary is separated with the single-stage impactor. The fraction greater than 5.0 µm is separated off by inertia on a baffle plate in the impactor. The fine particle fraction (FPF) follows the air current and is finally separated off on a depth filter. The fine particle fraction is determined gravimetrically. The fine particle fraction is calculated from the content of powder separated off on the filter in relation to the total quantity of powder used, i.e., the weighed powder sample per capsule.

Residual Water Content:

The residual water content in the dried products was determined by coulometric titration (Metrohm 737 KF coulometer with titration stand 703, Germany). For the determination powders were dissolved or dispersed in methanol (Hydranal-Methanol dry, VWR/Merck Eurolab). The Metrohm coulometer's measurement solution (Hydranal—Coulomat solution, VWR/Merck Eurolab) was conditioned at the beginning of the measurements, i.e., the measurement solution was tared out to a zero water content. The sample was injected into the titration cell and measured.

Stability Determination:

The powders or proteins contained in the powder were tested after spray-drying for various stabilities. In the case of IgG1 and calcitonin, the percentage protein aggregate content was used as the criterion for the stability of the formulations. In the case of lysozyme the percentage residual monomer content was used as the criterion for the stability of the formulations. The innovative excipients described in the invention were compared with pure protein formulations, analogous trehalose formulations, analogous raffinose formulations, analogous saccharose formulations, analogous saccharose-lactose formulations or analogous hydroxyl-ethyl starch formulations partially as reference formulations. The test for aggregates was analysed with a validated size exclusion chromatography method (SEC-HPLC) with UV detection (DAD). For this, the pre-treated powders were first reconstituted in ultra pure water (pH of 6 to 8).

Forced storage stability: selected formulations were tested for their stability after storage for one week at about 40° C. and about 75% relative humidity (40° C., 75% rh) in open glass vials.

Equilibrated storage stability: selected formulations were stored at about 22° C. and 50 to 55% relative humidity in open glass vials for one day after spray-drying (equilibration). The glass vials were then sealed and put on a flange under the above-mentioned conditions and tested for their stability after dry storage for four weeks at about 40° C.

Vacuum dried storage stability: selected formulations were stored at about 30° C. and about 0.15 millibar in open glass vials in a vacuum drying cabinet from the company Memmert (Germany) for one day after spray drying (vacuum drying). The glass vials were then removed from the vacuum drying cabinet, sealed and put on a flange and tested for their stability after storage for four weeks at about 40° C.

3 month stability: selected formulations were vacuum-dried in open glass vials after spray-drying (see above). The glass vials were sealed under nitrogen and put on a flange and stored at three different temperatures. The temperatures were 2-8° C., 25° C. and 40° C. The powders were tested for their stability after one month.

Open 3 month stability: selected formulations were stored after spray-drying in open glass vials at about 29% and/or 43% relative humidity and 25° C. The powders were tested for their stability after one month and three months. In selected formulations the aerodynamic performance of the powder was also determined by means of time of flight measurements (see above).

EXAMPLE 1

Spray Drying of a 10% (w/v) IgG1 Formulation

Pure IgG1 with a concentration of around 109 mg/ml formulated in a pH 6 glycine-histidine buffer (see Materials) was diluted with demineralized water (with a pH of around 7.5) to a content of 100 mg/ml and, in the absence of any other adjuvants, spray-dried as described above with application of cylone I at an atomizing air flow of around 0.67 m$^3$/h. The solution volume was 50 ml. The aggregate content was investigated as described above.

After one week's open storage at 75% relative air humidity and 40° C. (forced storage stability), the solution prepared from the reconstituted powder had around 18.9% and 18.2% aggregates respectively.

After one day's equilibration and four weeks' dry storage at 40° C., the solution prepared from the reconstituted powder had around 11.8% aggregates.

After one day's vacuum drying and four weeks' dry storage at 40° C., the solution prepared from the reconstituted powder had around 13.2% aggregates.

Spray Drying of a 3.33% (w/v) IgG1 Formulation

Pure IgG1 with a concentration of around 102.8 mg/ml formulated in a pH 6 glycine-histidine buffer (see Materials) was diluted with demineralized water (with a pH of around 7.5) to a content of 33 mg/ml and, in the absence of any other adjuvants, spray-dried as described above with application of cylone I at an atomizing air flow of around 0.67 m$^3$/h. The solution volume was 150 ml. The aggregate content was investigated as described above.

After one week's open storage at 75% relative air humidity and 40° C. (forced storage stability), the solution prepared from the reconstituted powder had around 16.3% aggregates.

After 1 and 3 months' storage at 2-8° C. (3 months' stability), the solution prepared from the reconstituted powder had around 4.5% and 4.4% aggregates respectively.

After 1 and 3 months' storage at 25° C. (3 months' stability), the solution prepared from the reconstituted powder had around 7.4% and 7.1% aggregates respectively.

After 1 and 3 months' storage at 40° C. (3 months' stability), the solution prepared from the reconstituted powder had around 13.3% and 18.1% aggregates respectively.

After 1 and 3 months' storage at around 29% relative air humidity and 25° C., the solution prepared from the reconstituted powder had around 5.5% and 6.6% aggregates respectively.

After 1 and 3 months' storage at around 43% relative air humidity and 25° C., the solution prepared from the reconstituted powder had around 5.6% and 7.0% aggregates respectively.

Spray Drying of a 9% (w/v) trehalose 1% (w/v) IgG1 Formulation 4.5 g trehalose were dissolved in around 40 ml demineralized water (with a pH of around 7.5). As the next step, around 4.6 ml pure IgG1 with a concentration of around 109 mg/ml formulated in a pH 6 glycine-histidine buffer (see Materials) were added and diluted with demineralized water (with a pH of around 7.5) to a volume of 50 ml. The thus obtained solution contained around 9% (w/v) adjuvant or matrix and 1% (w/v) protein and was spray-dried as described above with application of cylone I at an atomizing air flow of around 0.67 m$^3$/h. The aggregate content was investigated as described above.

The following aggregate contents were obtained for its storage stability:
After one week's open storage at 75% relative air humidity and 40° C. (forced storage stability), the solution prepared from the reconstituted powder had around 12.6% aggregates.

Spray Drying of a 3.00% (w/v) LS90P 0.33% (w/v) IgG1 Formulation 4.5 g LS90P were dissolved in around 140 ml demineralized water (with a pH of around 7.5). As the next step, around 4.864 ml pure IgG1 with a concentration of around 102.8 mg/ml formulated in a pH 6 glycine-histidine buffer (see Materials) were added and diluted with demineralized water (with a pH of around 7.5) to a volume of 150 ml. The thus obtained solution contained around 3.00% (w/v) adjuvant or matrix and 0.33% (w/v) protein and was spray-dried as described above with application of cylone I at an atomizing air flow of around 0.67 m$^3$/h. The aggregate content was investigated as described above.

The following aggregate contents were obtained for its storage stability:
After one week's open storage at 75% relative air humidity and 40° C. (forced storage stability), the solution prepared from the reconstituted powder had around 1.0% aggregates.

After 1 and 3 months' storage at 2-8° C. (3 months' stability), the solution prepared from the reconstituted powder had around 0.6% and 0.9% aggregates respectively.

After 1 and 3 months' storage at 25° C. (3 months' stability), the solution prepared from the reconstituted powder had around 0.8% and 1.3% aggregates respectively.

After 1 and 3 months' storage at 40° C. (3 months' stability), the solution prepared from the reconstituted powder had around 1.1% and 2.2% aggregates respectively.

The MMD of the powder was determined as described above.

The MMD of the powder after spray drying was 2.8 µm.

The MMAD and FPF of the powder were determined as described above.

The MMAD of the powder after spray drying was 3.8 µm, and the FPF was 23.6% in relation to the powder capsule weight.

Spray Drying of a 9.9% (w/v) LS55P 0.1% (w/v) IgG1 Formulation 4.950 g LS55P were dissolved in around 40 ml demineralized water (with a pH of around 7.5). As the next step, around 0.518 ml pure IgG1 with a concentration of around 96.55 mg/ml formulated in a pH 6 glycine-histidine buffer (see Materials) were added and diluted with demineralized water (with a pH of around 7.5) to a volume of 50 ml. The thus obtained solution contained around 9.9% (w/v) adjuvant or matrix and 0.1% (w/v) protein and was spray-dried as described above with application of cylone I at an atomizing air flow of around 0.67 m$^3$/h. The aggregate content was investigated as described above.

The following aggregate contents were obtained for its storage stability:
After one week's open storage at 75% relative air humidity and 40° C. (forced storage stability), the solution prepared from the reconstituted powder had around 5.7% aggregates.

After one day's vacuum drying and four weeks' dry storage at 40° C., the solution prepared from the reconstituted powder had around 4.7% aggregates.

Spray Drying of a 9% (w/v) LS55P 1% (w/v) IgG1 Formulation 4.5 g LS55P were dissolved in around 40 ml demineralized water (with a pH of around 7.5). As the next step, around 4.6 ml pure IgG1 with a concentration of around 109 mg/ml formulated in a pH 6 glycine-histidine buffer (see Materials) were added and diluted with demineralized water (with a pH of around 7.5) to a volume of 50 ml. The thus obtained solution contained around 9% (w/v) adjuvant or matrix and 1% (w/v) protein and was spray-dried as described above with application of cylone I at an atomizing air flow of around 0.67 m$^3$/h. The aggregate content was investigated as described above.

The following aggregate contents were obtained for its storage stability:

After one week's open storage at 75% relative air humidity and 40° C. (forced storage stability), the solution prepared from the reconstituted powder had around 2.3% aggregates.

After one day's equilibration and four weeks' dry storage at 40° C., the solution prepared from the reconstituted powder had around 1.8% aggregates.

After one day's vacuum drying and four weeks' dry storage at 40° C., the solution prepared from the reconstituted powder had around 1.4% aggregates.

Spray Drying of a 6% (w/v) LS55P 4% (w/v) IgG1 Formulation 3.0 g LS55P were dissolved in around 15 ml demineralized water (with a pH of around 7.5). As the next step, around 19.45 ml pure IgG1 with a concentration of around 102.8 mg/ml formulated in a pH 6 glycine-histidine buffer (see Materials) were added and diluted with demineralized water (with a pH of around 7.5) to a volume of 50 ml. The thus obtained solution contained around 6% (w/v) adjuvant or matrix and 4% (w/v) protein and was spray-dried as described above with application of cylone I at an atomizing air flow of around 0.67 m$^3$/h. The aggregate content was investigated as described above.

The following aggregate contents were obtained for its storage stability:

After one week's open storage at 75% relative air humidity and 40° C. (forced storage stability), the solution prepared from the reconstituted powder had around 4.0% aggregates.

Spray Drying of a 4% (w/v) LS55P 6% (w/v) IgG1 Formulation 2.0 g LS55P were dissolved in around 15 ml demineralized water (with a pH of around 7.5). As the next step, around 29.18 ml pure IgG1 with a concentration of around 102.8 mg/ml formulated in a pH 6 glycine-histidine buffer (see Materials) were added and diluted with demineralized water (with a pH of around 7.5) to a volume of 50 ml. The thus obtained solution contained around 4% (w/v) adjuvant or matrix and 6% (w/v) protein and was spray-dried as described above with application of cylone I at an atomizing air flow of around 0.67 m$^3$/h. The aggregate content was investigated as described above.

The following aggregate contents were obtained for its storage stability:

After one week's open storage at 75% relative air humidity and 40° C. (forced storage stability), the solution prepared from the reconstituted powder had around 6.9% aggregates.

Spray Drying of a 2.5% (w/v) LS55P 7.5% (w/v) IgG1 Formulation 1.25 g LS55P were dissolved in around 10 ml demineralized water (with a pH of around 7.5). As the next step, around 38.84 ml pure IgG1 with a concentration of around 96.55 mg/ml formulated in a pH 6 glycine-histidine buffer (see Materials) were added and diluted with demineralized water (with a pH of around 7.5) to a volume of 50 ml. The thus obtained solution contained around 2.5% (w/v) adjuvant or matrix and 7.5% (w/v) protein and was spray-dried as described above with application of cylone I at an atomizing air flow of around 0.67 m$^3$/h. The aggregate content was investigated as described above.

The following aggregate contents were obtained for its storage stability:

After one week's open storage at 75% relative air humidity and 40° C. (forced storage stability), the solution prepared from the reconstituted powder had around 5.9% aggregates.

After one day's vacuum drying and four weeks' dry storage at 40° C., the solution prepared from the reconstituted powder had around 6.1% aggregates.

Spray Drying of a 1.0% (w/v) LS55P 9.0% (w/v) IgG1 Formulation 0.50 g LS55P was dissolved in around 5 ml demineralized water (with a pH of around 7.5). As the next step, around 41.43 ml pure IgG1 with a concentration of around 96.55 mg/ml formulated in a pH 6 glycine-histidine buffer (see Materials) were added and diluted with demineralized water (with a pH of around 7.5) to a volume of 50 ml. The thus obtained solution contained around 1.0% (w/v) adjuvant or matrix and 9.0% (w/v) protein and was spray-dried as described above with application of cylone I at an atomizing air flow of around 0.67 m$^3$/h. The aggregate content was investigated as described above.

The following aggregate contents were obtained for its storage stability:

After one week's open storage at 75% relative air humidity and 40° C. (forced storage stability), the solution prepared from the reconstituted powder had around 10.8% aggregates.

After one day's vacuum drying and four weeks' dry storage at 40° C., the solution prepared from the reconstituted powder had around 8.0% aggregates.

Spray Drying of a 0.5% (w/v) LS55P 9.5% (w/v) IgG1 Formulation 0.25 g LS55P was dissolved in around 2.5 ml demineralized water (with a pH of around 7.5). As the next step, around 46.21 ml pure IgG1 with a concentration of around 102.8 mg/ml formulated in a pH 6 glycine-histidine buffer (see Materials) were added and diluted with demineralized water (with a pH of around 7.5) to a volume of 50 ml. The thus obtained solution contained around 0.5% (w/v) adjuvant or matrix and 9.5% (w/v) protein and was spray-dried as described above with application of cylone I at an atomizing air flow of around 0.67 m$^3$/h. The aggregate content was investigated as described above.

The following aggregate contents were obtained for its storage stability:

After one week's open storage at 75% relative air humidity and 40° C. (forced storage stability), the solution prepared from the reconstituted powder had around 13.7% aggregates.

Spray Drying of a 3.00% (w/v) LS55P 0.33% (w/v) IgG1 Formulation 9.0 g LS55P were dissolved in around 280 ml demineralized water (with a pH of around 7.5). As the next step, around 9.73 ml pure IgG1 with a concentration of around 102.8 mg/ml formulated in a pH 6 glycine-histidine buffer (see Materials) were added and diluted with demineralized water (with a pH of around 7.5) to a volume of 300 ml. The thus obtained solution contained around 3.0% (w/v) adjuvant or matrix and 0.33% (w/v) protein and was spray-dried as described above with application of cylone II at an atomizing air flow of around 0.67 m$^3$/h. The aggregate content was investigated as described above.

The following aggregate contents were obtained for its storage stability:
After one week's open storage at 75% relative air humidity and 40° C. (forced storage stability), the solution prepared from the reconstituted powder had around 5.0% aggregates.

The MMD of the powder was determined as described above.

The MMD of the powder after spray drying was 2.9 µm.

The MMAD and FPF of the powder were determined as described above.

The MMAD of the powder after spray drying was 4.3 µm, and the FPF was 15.9% in relation to the powder capsule weight.

Spray Drying of a 9.9% (w/v) Coupling Sugar 0.1% (w/v) IgG1 Formulation 6.290 g Coupling Sugar-containing syrup (equivalent to 4.950 g Coupling Sugar) were dissolved in around 40 ml demineralized water (with a pH of around 7.5). As the next step, around 0.518 ml pure IgG1 with a concentration of around 96.55 mg/ml formulated in a pH 6 glycine-histidine buffer (see Materials) were added and diluted with demineralized water (with a pH of around 7.5) to a volume of 50 ml. The thus obtained solution contained around 9.9% (w/v) adjuvant or matrix and 0.1% (w/v) protein and was spray-dried as described above with application of cylone I at an atomizing air flow of around 0.67 m$^3$/h. The aggregate content was investigated as described above.

The following aggregate contents were obtained for its storage stability:
After one week's open storage at 75% relative air humidity and 40° C. (forced storage stability), the solution prepared from the reconstituted powder had around 14.9% aggregates.

Spray Drying of a 9% (w/v) Coupling Sugar 1% (w/v) IgG1 Formulation 5.71 g Coupling Sugar-containing syrup (equivalent to 4.5 g Coupling Sugar) were dissolved in around 40 ml demineralized water (with a pH of around 7.5). As the next step, around 4.6 ml pure IgG1 with a concentration of around 109 mg/ml formulated in a pH 6 glycine-histidine buffer (see Materials) were added and diluted with demineralized water (with a pH of around 7.5) to a volume of 50 ml. The thus obtained solution contained around 9% (w/v) adjuvant or matrix and 1% (w/v) protein and was spray-dried as described above with application of cylone I at an atomizing air flow of around 0.67 m$^3$/h. The aggregate content was investigated as described above.

The following aggregate contents were obtained for its storage stability:
After one week's open storage at 75% relative air humidity and 40° C. (forced storage stability), the solution prepared from the reconstituted powder had around 4.9% aggregates.
After one day's equilibration and four weeks' dry storage at 40° C., the solution prepared from the reconstituted powder had around 3.2% aggregates.
After one day's vacuum drying and four weeks' dry storage at 40° C., the solution prepared from the reconstituted powder had around 2.1% aggregates.

Spray Drying of a 6% (w/v) Coupling Sugar 4% (w/v) IgG1 Formulation 3.81 g Coupling Sugar-containing syrup (equivalent to 3.0 g Coupling Sugar) were dissolved in around 25 ml demineralized water (with a pH of around 7.5). As the next step, around 19.45 ml pure IgG1 with a concentration of around 102.8 mg/ml formulated in a pH 6 glycine-histidine buffer (see Materials) were added and diluted with demineralized water (with a pH of around 7.5) to a volume of 50 ml. The thus obtained solution contained around 6% (w/v) adjuvant or matrix and 4% (w/v) protein and was spray-dried as described above with application of cylone I at an atomizing air flow of around 0.67 m$^3$/h. The aggregate content was investigated as described above.

The following aggregate contents were obtained for its storage stability:
After one week's open storage at 75% relative air humidity and 40° C. (forced storage stability), the solution prepared from the reconstituted powder had around 5.0% aggregates.

Spray Drying of a 4% (w/v) Coupling Sugar 6% (w/v) IgG1 Formulation 2.54 g Coupling Sugar-containing syrup (equivalent to 2.0 g Coupling Sugar) were dissolved in around 15 ml demineralized water (with a pH of around 7.5). As the next step, around 29.18 ml pure IgG1 with a concentration of around x mg/ml formulated in a pH 6 glycine-histidine buffer (see Materials) were added and diluted with demineralized water (with a pH of around 7.5) to a volume of 50 ml. The thus obtained solution contained around 4% (w/v) adjuvant or matrix and 6% (w/v) protein and was spray-dried as described above with application of cylone I at an atomizing air flow of around 0.67 m$^3$/h. The aggregate content was investigated as described above.

The following aggregate contents were obtained for its storage stability:
After one week's open storage at 75% relative air humidity and 40° C. (forced storage stability), the solution prepared from the reconstituted powder had around 9.9% aggregates.

Spray Drying of a 2.5% (w/v) Coupling Sugar 7.5% (w/v) IgG1 Formulation 1.59 g Coupling Sugar-containing syrup (equivalent to 1.250 g Coupling Sugar) was dissolved in around 8 ml demineralized water (with a pH of around 7.5). As the next step, around 38.84 ml pure IgG1 with a concentration of around 96.56 mg/ml formulated in a pH 6 glycine-histidine buffer (see Materials) were added and diluted with demineralized water (with a pH of around 7.5) to a volume of 50 ml. The thus obtained solution contained around 2.5% (w/v) adjuvant or matrix and 7.5% (w/v) protein and was spray-dried as described above with application of cylone I at an atomizing air flow of around 0.67 m³/h. The aggregate content was investigated as described above.

The following aggregate contents were obtained for its storage stability:

After one week's open storage at 75% relative air humidity and 40° C. (forced storage stability), the solution prepared from the reconstituted powder had around 10.8% aggregates.

Spray Drying of a 1.0% (w/v) Coupling Sugar 9.0% (w/v) IgG1 Formulation 0.653 g Coupling Sugar-containing syrup (equivalent to 0.50 g Coupling Sugar) was dissolved in around 5 ml demineralized water (with a pH of around 7.5). As the next step, around 41.43 ml pure IgG1 with a concentration of around 96.56 mg/ml formulated in a pH 6 glycine-histidine buffer (see Materials) were added and diluted with demineralized water (with a pH of around 7.5) to a volume of 50 ml. The thus obtained solution contained around 1.0% (w/v) adjuvant or matrix and 9.0% (w/v) protein and was spray-dried as described above with application of cylone I at an atomizing air flow of around 0.67 m³/h. The aggregate content was investigated as described above.

The following aggregate contents were obtained for its storage stability:

After one week's open storage at 75% relative air humidity and 40° C. (forced storage stability), the solution prepared from the reconstituted powder had around 13.1% aggregates.

Spray Drying of a 9% (w/v) Coupling Sugar S 1% (w/v) IgG1 Formulation 5.86 g Coupling Sugar S-containing syrup (equivalent to 4.5 g Coupling Sugar S) were dissolved in around 40 ml demineralized water (with a pH of around 7.5). As the next step, around 4.6 ml pure IgG1 with a concentration of around 109 mg/ml formulated in a pH 6 glycine-histidine buffer (see Materials) were added and diluted with demineralized water (with a pH of around 7.5) to a volume of 50 ml. The thus obtained solution contained around 9% (w/v) adjuvant or matrix and 1% (w/v) protein and was spray-dried as described above with application of cylone I at an atomizing air flow of around 0.67 m³/h. The aggregate content was investigated as described above.

The following aggregate contents were obtained for its storage stability:

After one week's open storage at 75% relative air humidity and 40° C. (forced storage stability), the solution prepared from the reconstituted powder had around 5.4% aggregates.

EXAMPLE 2

Spray Drying of an 8% (w/v) trehalose 1% (w/v) L-isoleucine 1% (w/v) IgG1 Formulation 4.0 g trehalose and 0.5 g L-isoleucine were dissolved in around 40 ml demineralized water (with a pH of around 7.5) in an ultrasonic bath. As the next step, around 4.6 ml pure IgG1 with a concentration of around 109 mg/ml formulated in a pH 6 glycine-histidine buffer (see Materials) were added and diluted with demineralized water (with a pH of around 7.5) to a volume of 50 ml. The thus obtained solution contained around 9% (w/v) adjuvant or matrix and 1% (w/v) protein and was spray-dried as described above with application of cylone I at an atomizing air flow of around 0.67 m³/h. The aggregate content was investigated as described above.

After one week's open storage at 75% relative air humidity and 40° C. (forced storage stability), the solution prepared from the reconstituted powder had around 22.2% aggregates.

Spray Drying of a 2.66% (w/v) LS90P 0.33% (w/v) L-isoleucine 0.33% (w/v) IgG1 Formulation 4.0 g LS90P and 0.50 g L-isoleucine were dissolved in around 140 ml demineralized water (with a pH of around 7.5) in an ultrasonic bath. As the next step, around 4.864 ml pure IgG1 with a concentration of around 102.8 mg/ml formulated in a pH 6 glycine-histidine buffer (see Materials) were added and diluted with demineralized water (with a pH of around 7.5) to a volume of 150 ml. The thus obtained solution contained around 3.00% (w/v) adjuvant or matrix and 0.33% (w/v) protein and was spray-dried as described above with application of cylone II at an atomizing air flow of around 0.67 m³/h. The aggregate content was investigated as described above.

The following aggregate contents were obtained for its storage stability:

After one week's open storage at 75% relative air humidity and 40° C. (forced storage stability), the solution prepared from the reconstituted powder had around 0.7% aggregates.

After 1 and 3 months' storage at 2-8° C. (3 months' stability), the solution prepared from the reconstituted powder had around 0.7% and 1.0% aggregates respectively.

After 1 and 3 months' storage at 25° C. (3 months' stability), the solution prepared from the reconstituted powder had around 0.8% and 1.1% aggregates respectively.

After 1 and 3 months' storage at 40° C. (3 months' stability), the solution prepared from the reconstituted powder had around 0.6% and 1.1% aggregates respectively.

The MMAD and FPF of the powder were determined as described above.

The MMAD of the powder after spray drying was 7.3 µm, and the FPF was 28.1% in relation to the powder capsule weight.

Spray Drying of an 8% (w/v) LS55P 1% (w/v) L-isoleucine 1% (w/v) IgG1 Formulation 4.00 g LS90P and 0.50 g L-isoleucine were dissolved in around 40 ml demineralized water (with a pH of around 7.5) in an ultrasonic bath. As the next step, around 4.60 ml pure IgG1 with a concentration of around 109 mg/ml formulated in a pH 6 glycine-histidine buffer (see Materials) were added and diluted with demineralized water (with a pH of around 7.5) to a volume of 50 ml. The thus obtained solution contained around 9% (w/v) adjuvant or matrix and 1% (w/v) protein and was spray-dried as described above with application of cylone I at an atomizing air flow of around 0.67 m³/h. The aggregate content was investigated as described above.

After one week's open storage at 75% relative air humidity and 40° C. (forced storage stability), the solution prepared from the reconstituted powder had around 5.5% aggregates.

After one day's equilibration and four weeks' dry storage at 40° C., the solution prepared from the reconstituted powder had around 1.8% aggregates.

After one day's vacuum drying and four weeks' dry storage at 40° C., the solution prepared from the reconstituted powder had around 1.8% aggregates.

Spray Drying of a 2.66% (w/v) LS55P 0.33% (w/v) L-isoleucine 0.33% (w/v) IgG1 Formulation 8.0 g LS55P and 1 g L-isoleucine were dissolved in around 280 ml demineralized water (with a pH of around 7.5) in an ultrasonic bath. As the next step, around 9.7 ml pure IgG1 with a concentration of around 102.8 mg/ml formulated in a pH 6 glycine-histidine buffer (see Materials) were added and diluted with demineralized water (with a pH of around 7.5) to a volume of 300 ml. The thus obtained solution contained around 3% (w/v) adjuvant or matrix and 0.33% (w/v) protein and was spray-dried as described above with application of cylone II at an atomizing air flow of around 0.67 m$^3$/h. The aggregate content was investigated as described above.

After one week's open storage at 75% relative air humidity and 40° C. (forced storage stability), the solution prepared from the reconstituted powder had around 5.9% aggregates.

After 1 and 3 months' storage at 2-8° C. (3 months' stability), the solution prepared from the reconstituted powder had around 1.6% aggregates respectively.

After 1 and 3 months' storage at 25° C. (3 months' stability), the solution prepared from the reconstituted powder had around 1.6% and 1.8% aggregates respectively.

After 1 and 3 months' storage at 40° C. (3 months' stability), the solution prepared from the reconstituted powder had around 1.6% and 1.8% aggregates respectively.

The MMAD and FPF of the powder were determined as described above.

The MMAD of the powder after spray drying was 4.9 μm, and the FPF was 34.7% in relation to the powder capsule weight.

Spray Drying of an 8% (w/v) Coupling Sugar 1% (w/v) L-isoleucine 1% (w/v) IgG1 Formulation 5.08 g Coupling Sugar-containing syrup (equivalent to 4.0 g Coupling Sugar) and 0.50 g L-isoleucine were dissolved in around 40 ml demineralized water (with a pH of around 7.5) in an ultrasonic bath. As the next step, around 4.60 ml pure IgG1 with a concentration of around 109 mg/ml formulated in a pH 6 glycine-histidine buffer (see Materials) were added and diluted with demineralized water (with a pH of around 7.5) to a volume of 50 ml. The thus obtained solution contained around 9% (w/v) adjuvant or matrix and 1% (w/v) protein and was spray-dried as described above with application of cylone I at an atomizing air flow of around 0.67 $m^3$/h. The aggregate content was investigated as described above.

After one week's open storage at 75% relative air humidity and 40° C. (forced storage stability), the solution prepared from the reconstituted powder had around 7.1% aggregates.

After one day's equilibration and four weeks' dry storage at 40° C., the solution prepared from the reconstituted powder had around 2.5% aggregates.

After one day's vacuum drying and four weeks' dry storage at 40° C., the solution prepared from the reconstituted powder had around 1.1% aggregates.

Spray Drying of an 8% (w/v) Coupling Sugar S 1% (w/v) L-isoleucine 1% (w/v) IgG1 Formulation 5.21 g Coupling Sugar S-containing syrup (equivalent to 4.0 g Coupling Sugar S) and 0.50 g L-isoleucine were dissolved in around 40 ml demineralized water (with a pH of around 7.5) in an ultrasonic bath. As the next step, around 4.60 ml pure IgG1 with a concentration of around 109 mg/ml formulated in a pH 6 glycine-histidine buffer (see Materials) were added and diluted with demineralized water (with a pH of around 7.5) to a volume of 50 ml. The thus obtained solution contained around 9% (w/v) adjuvant or matrix and 1% (w/v) protein and was spray-dried as described above with application of cylone I at an atomizing air flow of around 0.67 $m^3$/h. The aggregate content was investigated as described above.

After one week's open storage at 75% relative air humidity and 40° C. (forced storage stability), the solution prepared from the reconstituted powder had around 6.8% aggregates.

EXAMPLE 3

Spray Drying of a 3% (w/v) trehalose 6% (w/v) L-citrulline 1% (w/v) IgG1 Formulation 1.50 g trehalose and 3.00 g L-citrulline were dissolved in around 40 ml demineralized water (with a pH of around 7.5) in an ultrasonic bath. As the next step, around 4.6 ml pure IgG1 with a concentration of around 109 mg/ml formulated in a pH 6 glycine-histidine buffer (see Materials) were added and diluted with demineralized water (with a pH of around 7.5) to a volume of 50 ml. The thus obtained solution contained around 9% (w/v) adjuvant or matrix and 1% (w/v) protein and was spray-dried as described above with application of cylone I at an atomizing air flow of around 0.67 $m^3$/h. The aggregate content was investigated as described above.

After one week's open storage at 75% relative air humidity and 40° C. (forced storage stability), the solution prepared from the reconstituted powder had around 5.9% aggregates.

Spray Drying of a 3% (w/v) LS55P 6% (w/v) L-citrulline 1% (w/v) IgG1 Formulation 1.50 g LS55P and 3.00 g L-citrulline were dissolved in around 40 ml demineralized water (with a pH of around 7.5) in an ultrasonic bath. As the next step, around 4.60 ml pure IgG1 with a concentration of around 109 mg/ml formulated in a pH 6 glycine-histidine buffer (see Materials) were added and diluted with demineralized water (with a pH of around 7.5) to a volume of 50 ml. The thus obtained solution contained around 9% (w/v) adjuvant or matrix and 1% (w/v) protein and was spray-dried as described above with application of cylone I at an atomizing air flow of around 0.67 $m^3$/h. The aggregate content was investigated as described above.

After one week's open storage at 75% relative air humidity and 40° C. (forced storage stability), the solution prepared from the reconstituted powder had around 2.9% aggregates.

After one day's equilibration and four weeks' dry storage at 40° C., the solution prepared from the reconstituted powder had around 1.8% aggregates.

After one day's vacuum drying and four weeks' dry storage at 40° C., the solution prepared from the reconstituted powder had around 1.3% aggregates.

Spray Drying of a 3% (w/v) Coupling Sugar 6% L-citrulline 1% (w/v) IgG1 Formulation 1.91 g Coupling Sugar-containing syrup (equivalent to 1.5 g Coupling Sugar) and 3.00 g L-citrulline were dissolved in around 40 ml demineralized water (with a pH of around 7.5) in an ultrasonic bath. As the next step, around 4.60 ml pure IgG1 with a concentration of around 109 mg/ml formulated in a pH 6 glycine-histidine buffer (see Materials) were added and diluted with demineralized water (with a pH of around 7.5) to a volume of 50 ml. The thus obtained solution contained around 9% (w/v) adjuvant or matrix and 1% (w/v) protein and was spray-dried as described above with application of cylone I at an atomizing air flow of around 0.67 $m^3$/h. The aggregate content was investigated as described above.

After one week's open storage at 75% relative air humidity and 40° C. (forced storage stability), the solution prepared from the reconstituted powder had around 3.9% aggregates.

After one day's equilibration and four weeks' dry storage at 40° C., the solution prepared from the reconstituted powder had around 1.4% aggregates.

After one day's vacuum drying and four weeks' dry storage at 40° C., the solution prepared from the reconstituted powder had around 1.3% aggregates.

Spray Drying of a 3% (w/v) Coupling Sugar S 6% L-citrulline 1% (w/v) IgG1 Formulation 1.95 g Coupling Sugar S-containing syrup (equivalent to 1.5 g Coupling Sugar S) and 3.00 g L-citrulline were dissolved in around 40 ml demineralized water (with a pH of around 7.5) in an ultrasonic bath. As the next step, around 4.60 ml pure IgG1 with a concentration of around 109 mg/ml formulated in a pH 6 glycine-histidine buffer (see Materials) were added and diluted with demineralized water (with a pH of around 7.5) to a volume of 50 ml. The thus obtained solution contained around 9% (w/v) adjuvant or matrix and 1% (w/v) protein and was spray-dried as described above with application of cylone I at an atomizing air flow of around 0.67 $m^3$/h. The aggregate content was investigated as described above.

After one week's open storage at 75% relative air humidity and 40° C. (forced storage stability), the solution prepared from the reconstituted powder had around 3.1% aggregates.

EXAMPLE 4

Spray Drying of a 2.66% (w/v) trehalose 0.33% (w/v) tri-isoleucine 0.33% (w/v) IgG1 Formulation 8.0 g trehalose and 1 g tri-isoleucine were dissolved in around 280 ml demineralized water (with a pH of around 7.5) in an ultrasonic bath. As the next step, around 12.30 ml pure IgG1 with a concentration of around 96.55 mg/ml formulated in a pH 6 glycine-histidine buffer (see Materials) were added and diluted with demineralized water (with a pH of around 7.5) to a volume of 300 ml. The thus obtained solution contained around 3% (w/v) adjuvant or matrix and 0.33% (w/v) protein and was spray-dried as described above with application of cylone II at an atomizing air flow of around 0.67 $m^3$/h. The aggregate content was investigated as described above.

After one week's open storage at 75% relative air humidity and 40° C. (forced storage stability), the solution prepared from the reconstituted powder had around 26.7% aggregates.

Spray Drying of a 2.66% (w/v) raffinose 0.33% (w/v) tri-isoleucine 0.33% (w/v) IgG1 Formulation 8.0 g raffinose and 1 g tri-isoleucine were dissolved in around 140 ml demineralized water (with a pH of around 7.5) in an ultrasonic bath. As the next step, around 4.87 ml pure IgG1 with a concentration of around 102.8 mg/ml formulated in a pH 6 glycine-histidine buffer (see Materials) were added and diluted with demineralized water (with a pH of around 7.5) to a volume of 300 ml. The thus obtained solution contained around 3% (w/v) adjuvant or matrix and 0.33% (w/v) protein and was spray-dried as described above with application of cylone II at an atomizing air flow of around 0.67 $m^3$/h. The aggregate content was investigated as described above.

After one week's open storage at 75% relative air humidity and 40° C. (forced storage stability), the solution prepared from the reconstituted powder had around 12.6% aggregates.

Spray Drying of a 2.66% (w/v) hydroxyethyl Starch (HES) 0.33% (w/v) tri-isoleucine 0.33% (w/v) IgG1 Formulation 8.0 g HES and 1 g tri-isoleucine were dissolved in around 140 ml demineralized water (with a pH of around 7.5) in an ultrasonic bath at around 80° C. with stirring. As the next step, around 4.87 ml pure IgG1 with a concentration of around 102.8 mg/ml formulated in a pH 6 glycine-histidine buffer (see Materials) were added to the previously refrigerated turbid solution and diluted with demineralized water (with a pH of around 7.5) to a volume of 150 ml. The thus obtained solution contained around 3% (w/v) adjuvant or matrix and 0.33% (w/v) protein and was spray-dried as described above with application of cylone II at an atomizing air flow of around 0.67 $m^3$/h. The aggregate content was investigated as described above.

After one week's open storage at 75% relative air humidity and 40° C. (forced storage stability), the solution prepared from the reconstituted powder had around 18.6% aggregates.

After 1 and 3 months' open storage at around 43% relative air humidity and 25° C. (open 3 months' stability), the solution prepared from the reconstituted powder had around 11.9% and 15.4% aggregates respectively.

Spray Drying of a 2.00% (w/v) saccharose 0.66% (w/v) Lactose 0.33% (w/v) tri-isoleucine 0.33% (w/v) IgG1 Formulation 6.0 g saccharose, 2.0 g lactose, and 1 g tri-isoleucine were dissolved in around 280 ml demineralized water (with a pH of around 7.5) in an ultrasonic bath. As the next step, around 9.73 ml pure IgG1 with a concentration of around 102.8 mg/ml formulated in a pH 6 glycine-histidine buffer (see Materials) were added and diluted with demineralized water (with a pH of around 7.5) to a volume of 300 ml. The thus obtained solution contained around 3% (w/v) adjuvant or matrix and 0.33% (w/v) protein and was spray-dried as described above with application of cylone II at an atomizing air flow of around 0.67 $m^3$/h. The aggregate content was investigated as described above.

After one week's open storage at 75% relative air humidity and 40° C. (forced storage stability), the solution prepared from the reconstituted powder had around 8.8% aggregates.

Spray Drying of a 2.66% (w/v) saccharose 0.33% (w/v) tri-isoleucine 0.33% (w/v) IgG1 Formulation 8.0 g saccharose and 1 g tri-isoleucine were dissolved in around 280 ml demineralized water (with a pH of around 7.5) in an ultrasonic bath. As the next step, around 9.73 ml pure IgG1 with a concentration of around 102.8 mg/ml formulated in a pH 6 glycine-histidine buffer (see Materials) were added and diluted with demineralized water (with a pH of around 7.5) to a volume of 300 ml. The thus obtained solution contained around 3% (w/v) adjuvant or matrix and 0.33% (w/v) protein and was spray-dried as described above with application of cylone II at an atomizing air flow of around 0.67 m³/h. The aggregate content was investigated as described above.

After one week's open storage at 75% relative air humidity and 40° C. (forced storage stability), the solution prepared from the reconstituted powder had around 5.6% aggregates.

Spray Drying of a 2.66% (w/v) LS90P 0.33% (w/v) tri-isoleucine 0.33% (w/v) IgG1 formulation 4.0 g LS90P and 0.50 g tri-isoleucine were dissolved in around 140 ml demineralized water (with a pH of around 7.5). As the next step, around 4.864 ml pure IgG1 with a concentration of around 102.8 mg/ml formulated in a pH 6 glycine-histidine buffer (see Materials) were added and diluted with demineralized water (with a pH of around 7.5) to a volume of 150 ml. The thus obtained solution contained around 3.00% (w/v) adjuvant or matrix and 0.33% (w/v) protein and was spray-dried as described above with application of cylone II at an atomizing air flow of around 0.67 m³/h. The aggregate content was investigated as described above.

The following aggregate contents were obtained for its storage stability:

After one week's open storage at 75% relative air humidity and 40° C. (forced storage stability), the solution prepared from the reconstituted powder had around 2.3% aggregates.

After 1 and 3 months' storage at 2-8° C. (3 months' stability), the solution prepared from the reconstituted powder had around 0.7% and 1.0% aggregates respectively.

After 1 and 3 months' storage at 25° C. (3 months' stability), the solution prepared from the reconstituted powder had around 0.8% and 1.4% aggregates respectively.

After 1 and 3 months' storage at 40° C. (3 months' stability), the solution prepared from the reconstituted powder had around 0.9% and 2.2% aggregates respectively.

After 1 and 3 months' open storage at around 29% relative air humidity and 25° C., the solution prepared from the reconstituted powder had around 0.4% and 0.7% aggregates respectively.

After 1 and 3 months' open storage at around 43% relative air humidity and 25° C., the solution prepared from the reconstituted powder had around 0.5% and 0.6% aggregates respectively.

The MMD of the powder was determined as described above.

The MMD of the powder after spray drying was 4.7 μm.

The MMAD and FPF of the powder were determined as described above.

The MMAD of the powder after spray drying was 4.8 μm, and the FPF was 53.2% in relation to the powder capsule weight.

Spray Drying of a 2.66% (w/v) LS90P 0.33% (w/v) tri-isoleucine 0.33% (w/v) IgG1 Formulation 4.0 g LS90P and 0.50 g tri-isoleucine were dissolved in around 140 ml demineralized water (with a pH of around 7.5). As the next step, around 4.864 ml pure IgG1 with a concentration of around 102.8 mg/ml formulated in a pH 6 glycine-histidine buffer (see Materials) were added and diluted with demineralized water (with a pH of around 7.5) to a volume of 150 ml. The thus obtained solution contained around 3.00% (w/v) adjuvant or matrix and 0.33% (w/v) protein and was spray-dried as described above with application of cylone II at an atomizing air flow of around 1.05 m³/h. The aggregate content was investigated as described above.

The following aggregate contents were obtained for its storage stability:

After one week's open storage at 75% relative air humidity and 40° C. (forced storage stability), the solution prepared from the reconstituted powder had around 2.2% aggregates.

After 1 and 3 months' storage at around 29% relative air humidity and 25° C. (open 3 months' stability), the solution prepared from the reconstituted powder had around 0.5% and 0.6% aggregates respectively.

After 1 and 3 months' storage at around 43% relative air humidity and 25° C. (open 3 months' stability), the solution prepared from the reconstituted powder had around 0.5% and 0.7% aggregates respectively.

The MMD of the powder was determined as described above.

The MMD of the powder after spray drying was 2.7 μm.

The MMAD and FPF of the powder were determined as described above.

The MMAD of the powder after spray drying was 3.6 μm, and the FPF was 58.0% in relation to the powder capsule weight.

Spray Drying of a 2.66% (w/v) LS90P 0.33% (w/v) tri-isoleucine 0.33% (w/v) IgG1 formulation 4.0 g LS90P and 0.50 g tri-isoleucine were dissolved in around 140 ml demineralized water (with a pH of around 7.5). As the next step, around 4.864 ml pure IgG1 with a concentration of around 102.8 mg/ml formulated in a pH 6 glycine-histidine buffer (see Materials) were added and diluted with demineralized water (with a pH of around 7.5) to a volume of 150 ml. The thus obtained solution contained around 3.00% (w/v) adjuvant or matrix and 0.33% (w/v) protein and was spray-dried as described above with application of cylone II at an atomizing air flow of around 1.74 m³/h. The aggregate content was investigated as described above.

The following aggregate contents were obtained for its storage stability:

After one week's open storage at 75% relative air humidity and 40° C. (forced storage stability), the solution prepared from the reconstituted powder had around % aggregates.

After 1 and 3 months' storage at around 29% relative air humidity and 25° C. (open 3 months' stability), the solution prepared from the reconstituted powder had around 0.5% and 0.6% aggregates respectively.

After 1 and 3 months' storage at around 43% relative air humidity and 25° C. (open 3 months' stability), the solution prepared from the reconstituted powder had around 0.5% and 0.8% aggregates respectively.

The MMD of the powder was determined as described above.

The MMD of the powder after spray drying was 2.6 μm.

The MMAD and FPF of the powder were determined as described above.

The MMAD of the powder after spray drying was 3.3 μm, and the FPF was 58.9% in relation to the powder capsule weight.

Spray Drying of a 1.60% (w/v) LS90P 0.20% (w/v) tri-isoleucine 0.20% (w/v) IgG1 formulation 4.0 g LS90P and 0.50 g tri-isoleucine were dissolved in around 220 ml demineralized water (with a pH of around 7.5). As the next step, around 4.864 ml pure IgG1 with a concentration of around 102.8 mg/ml formulated in a pH 6 glycine-histidine buffer (see Materials) were added and diluted with demineralized water (with a pH of around 7.5) to a volume of 250 ml. The thus obtained solution contained around 1.80% (w/v) adjuvant or matrix and 0.20% (w/v) protein and was spray-dried as described above with application of cylone II at an atomizing air flow of around 0.67 m³/h. The aggregate content was investigated as described above.

The following aggregate contents were obtained for its storage stability:
- After one week's open storage at 75% relative air humidity and 40° C. (forced storage stability), the solution prepared from the reconstituted powder had around 2.2% aggregates.
- After 1 and 3 months' storage at around 29% relative air humidity and 25° C. (open 3 months' stability), the solution prepared from the reconstituted powder had around 0.5% and 0.5% aggregates respectively.
- After 1 and 3 months' storage at around 43% relative air humidity and 25° C. (open 3 months' stability), the solution prepared from the reconstituted powder had around 0.7% and 0.7% aggregates respectively.

The MMD of the powder was determined as described above.

The MMD of the powder after spray drying was 3.2 μm.

The MMAD and FPF of the powder were determined as described above.

The MMAD of the powder after spray drying was 3.9 μm, and the FPF was 55.6% in relation to the powder capsule weight.

Spray Drying of a 2.833% (w/v) LS90P 0.166% (w/v) tri-isoleucine 0.33% (w/v) IgG1 Formulation 4.25 g LS90P and 0.25 g tri-isoleucine were dissolved in around 140 ml demineralized water (with a pH of around 7.5). As the next step, around 4.864 ml pure IgG1 with a concentration of around 102.8 mg/ml formulated in a pH 6 glycine-histidine buffer (see Materials) were added and diluted with demineralized water (with a pH of around 7.5) to a volume of 150 ml. The thus obtained solution contained around 3.00% (w/v) adjuvant or matrix and 0.33% (w/v) protein and was spray-dried as described above with application of cylone II at an atomizing air flow of around 0.67 m³/h. The aggregate content was investigated as described above.

The following aggregate contents were obtained for its storage stability:
- After one week's open storage at 75% relative air humidity and 40° C. (forced storage stability), the solution prepared from the reconstituted powder had around 1.5% aggregates.
- After 1 and 3 months' storage at around 29% relative air humidity and 25° C. (open 3 months' stability), the solution prepared from the reconstituted powder had around 0.5% and 0.5% aggregates respectively.
- After 1 and 3 months' storage at around 43% relative air humidity and 25° C. (open 3 months' stability), the solution prepared from the reconstituted powder had around 0.5% and 0.6% aggregates respectively.

The MMD of the powder was determined as described above.

The MMD of the powder after spray drying was 4.8 μm.

The MMAD and FPF of the powder were determined as described above.

The MMAD of the powder after spray drying was 5.2 μm, and the FPF was 45.7% in relation to the powder capsule weight.

Spray Drying of a 2.9166% (w/v) LS90P 0.0833% (w/v) tri-isoleucine 0.33% (w/v) IgG1 formulation 4.375 g LS90P and 0.125 g tri-isoleucine were dissolved in around 140 ml demineralized water (with a pH of around 7.5). As the next step, around 4.864 ml pure IgG1 with a concentration of around 102.8 mg/ml formulated in a pH 6 glycine-histidine buffer (see Materials) were added and diluted with demineralized water (with a pH of around 7.5) to a volume of 150 ml. The thus obtained solution contained around 3.00% (w/v) adjuvant or matrix and 0.33% (w/v) protein and was spray-dried as described above with application of cylone II at an atomizing air flow of around 0.67 m³/h. The aggregate content was investigated as described above.

The following aggregate contents were obtained for its storage stability:
- After one week's open storage at 75% relative air humidity and 40° C. (forced storage stability), the solution prepared from the reconstituted powder had around 1.2% aggregates.
- After 1 and 3 months' storage at around 29% relative air humidity and 25° C. (open 3 months' stability), the solution prepared from the reconstituted powder had around 0.4% and 0.5% aggregates respectively.
- After 1 and 3 months' storage at around 43% relative air humidity and 25° C. (open 3 months' stability), the solution prepared from the reconstituted powder had around 0.5% and 0.6% aggregates respectively.

The MMD of the powder was determined as described above.

The MMD of the powder after spray drying was 4.2 μm.

The MMAD and FPF of the powder were determined as described above.

The MMAD of the powder after spray drying was 6.1 μm, and the FPF was 39.6% in relation to the powder capsule weight.

Spray Drying of a 2.66% (w/v) LS55P 0.33% (w/v) tri-isoleucine 0.33% (w/v) IgG1 formulation 8.0 g LS55P and 1 g tri-isoleucine were dissolved in around 280 ml demineralized water (with a pH of around 7.5) in an ultrasonic bath. As the next step, around 9.73 ml pure IgG1 with a concentration of around 102.8 mg/ml formulated in a pH 6 glycine-histidine buffer (see Materials) were added and diluted with demineralized water (with a pH of around 7.5) to a volume of 300 ml. The thus obtained solution contained around 3% (w/v) adjuvant or matrix and 0.33% (w/v) protein and was spray-dried as described above with application of cylone II at an atomizing air flow of around 0.67 m³/h. The aggregate content was investigated as described above.
- After one week's open storage at 75% relative air humidity and 40° C. (forced storage stability), the solution prepared from the reconstituted powder had around 2.1% aggregates.
- After 1 and 3 months' storage at 2-8° C. (3 months' stability), the solution prepared from the reconstituted powder had around 0.8% and 1.5% aggregates respectively.

After 1 and 3 months' storage at 25° C. (3 months' stability), the solution prepared from the reconstituted powder had around 0.9% and 1.5% aggregates respectively.

After 1 and 3 months' storage at 40° C. (3 months' stability), the solution prepared from the reconstituted powder had around 1.3% and 2.6% aggregates respectively.

After 1 and 3 months' storage at around 43% relative air humidity and 25° C. (open 3 months' stability), the solution prepared from the reconstituted powder had around 1.0% and 1.0% aggregates respectively.

The MMD of the powder was determined as described above.

The MMD of the powder after spray drying was 3.4 µm.

The MMAD and FPF of the powder were determined as described above.

The MMAD of the powder after spray drying was 3.9 µm, and the FPF was 58.3% in relation to the powder capsule weight.

After one month's storage at around 43% relative air humidity and 25° C. (open 3 months' stability), the MMAD was 3.8 µm, and the FPF was 59.6% in relation to the powder capsule weight.

Spray Drying of a 2.833% (w/v) LS55P 0.166% (w/v) Tri-isoleucine 0.33% (w/v) IgG1 Formulation 8.5 g LS90P and 0.5 g tri-isoleucine were dissolved in around 280 ml demineralized water (with a pH of around 7.5) in an ultrasonic bath. As the next step, around 9.73 ml pure IgG1 with a concentration of around 102.8 mg/ml formulated in a pH 6 glycine-histidine buffer (see Materials) were added and diluted with demineralized water (with a pH of around 7.5) to a volume of 300 ml. The thus obtained solution contained around 3% (w/v) adjuvant or matrix and 0.33% (w/v) protein and was spray-dried as described above with application of cylone II at an atomizing air flow of around 0.67 m³/h. The aggregate content was investigated as described above.

After one week's open storage at 75% relative air humidity and 40° C. (forced storage stability), the solution prepared from the reconstituted powder had around 3.4% aggregates.

After 1 and 3 months' storage at around 43% relative air humidity and 25° C. (open 3 months' stability), the solution prepared from the reconstituted powder had around 1.3% and 1.5% aggregates respectively.

The MMD of the powder was determined as described above.

The MMD of the powder after spray drying was 2.9 µm.

The MMAD and FPF of the powder were determined as described above.

The MMAD of the powder after spray drying was 4.4 µm, and the FPF was 58.6% in relation to the powder capsule weight.

Spray Drying of a 2.9166% (w/v) LS55P 0.0833% (w/v) Tri-isoleucine 0.33% (w/v) IgG1 Formulation 8.75 g LS90P and 0.25 g tri-isoleucine were dissolved in around 280 ml demineralized water (with a pH of around 7.5). As the next step, around 9.73 ml pure IgG1 with a concentration of around 102.8 mg/ml formulated in a pH 6 glycine-histidine buffer (see Materials) were added and diluted with demineralized water (with a pH of around 7.5) to a volume of 300 ml. The thus obtained solution contained around 3% (w/v) adjuvant or matrix and 0.33% (w/v) protein and was spray-dried as described above with application of cylone II at an atomizing air flow of around 0.67 m³/h. The aggregate content was investigated as described above.

After one week's open storage at 75% relative air humidity and 40° C. (forced storage stability), the solution prepared from the reconstituted powder had around 4.4% aggregates.

After 1 and 3 months' storage at around 43% relative air humidity and 25° C. (open 3 months' stability), the solution prepared from the reconstituted powder had around 0.7% and 0.8% aggregates respectively.

The MMD of the powder was determined as described above.

The MMD of the powder after spray drying was 2.9 µm.

The MMAD and FPF of the powder were determined as described above.

The MMAD of the powder after spray drying was 4.4 µm, and the FPF was 58.6% in relation to the powder capsule weight.

EXAMPLE 5

Production of Further Powders According to the Invention

Spray Drying of a 3.33% (w/v) Lysozyme Formulation 5 g lysozyme were dissolved in around 140 ml demineralized water (with a pH of around 7.5) and diluted with demineralized water (with a pH of around 7.5) to a volume of 150 ml. The thus obtained solution was spray-dried as described above with application of cylone II.

The residual monomer content was determined as described above. After forced storage, the solution prepared from the reconstituted powder had a residual monomer content of 35.3%. The MMD of the powder was determined as described above. The MMD of the powder was 3.2 µm. The MMAD and FPF of the powder were determined as described above. The MMAD was 4.0 µm, and the FPF was 70.4% in relation to the powder capsule weight.

Spray Drying of a 3.00% (w/v) LS90P 0.33% (w/v) Lysozyme Formulation 9.0 g LS90P were dissolved in around 280 ml demineralized water (with a pH of around 7.5) in an ultrasonic bath. As the next step, 1 g lysozyme was added and diluted with demineralized water (with a pH of around 7.5) to a volume of 300 ml. The thus obtained solution was spray-dried as described above with application of cylone II.

The residual monomer content was determined as described above. After forced storage, the solution prepared from the reconstituted powder had a residual monomer content of 62.1%. The MMD of the powder was determined as described above. The MMD of the powder was 4.0 µm. The MMAD and FPF of the powder were determined as described above. The MMAD was 3.7 µm, and the FPF was 24.7% in relation to the powder capsule weight.

Spray Drying of a 2.66% (w/v) LS90P 0.33% (w/v) Isoleucine 0.33% (w/v) Lysozyme Formulation 8.0 g LS90P and 1 g isoleucine were dissolved in around 280 ml demineralized water (with a pH of around 7.5) in an ultrasonic bath. As the next step, 1 g lysozyme was added and diluted with demineralized water (with a pH of around 7.5) to a volume of 300 ml. The thus obtained solution was spray-dried as described above with application of cylone II.

The residual monomer content was determined as described above. After forced storage, the solution prepared from the reconstituted powder had a residual monomer content of 47.9%. The MMD of the powder was determined as described above. The MMD of the powder was 3.9 μm. The MMAD and FPF of the powder were determined as described above. The MMAD was 4.1 μm, and the FPF was 29.0% in relation to the powder capsule weight.

Spray Drying of a 2.66% (w/v) LS90P 0.33% (w/v) Tri-isoleucine 0.33% (w/v) Lysozyme Formulation 8.0 g LS90P and 1 g tri-isoleucine were dissolved in around 280 ml demineralized water (with a pH of around 7.5) in an ultrasonic bath. As the next step, 1 g lysozyme was added and diluted with demineralized water (with a pH of around 7.5) to a volume of 300 ml. The thus obtained solution was spray-dried as described above with application of cylone II.

The residual monomer content was determined as described above. After forced storage, the solution prepared from the reconstituted powder had a residual monomer content of 47.9%. The MMD of the powder was determined as described above. The MMD of the powder was 2.7 μm. The MMAD and FPF of the powder were determined as described above. The MMAD was 3.6 μm, and the FPF was 58.6% in relation to the powder capsule weight.

Spray Drying of a 3.33% (w/v) Calcitonin Formulation 1 g calcitonin was dissolved in around 25 ml demineralized water (with a pH of around 7.5) and diluted with demineralized water (with a pH of around 7.5) to a volume of 30 ml. The thus obtained solution was spray-dried as described above with application of cylone II.

The aggregate content was investigated as described above.
  After 3 months' storage at 2-8° C. (3 months' stability), the solution prepared from the reconstituted powder had around 4.1% aggregates respectively.
  After 3 months' storage at 25° C. (3 months' stability), the solution prepared from the reconstituted powder had around 4.9% aggregates respectively.
  After 3 months' storage at 40° C. (3 months' stability), the solution prepared from the reconstituted powder had around 7.4% aggregates respectively.
The MMAD and FPF of the powder were determined as described above. The MMAD was 3.9 μm, and the FPF was 59.0% in relation to the powder capsule weight.

Spray Drying of a 3.166% (w/v) LS90P 0.166% (w/v) Calcitonin Formulation 4.750 g LS90P were dissolved in around 140 ml demineralized water (with a pH of around 7.5). As the next step, 0.250 g calcitonin was added and diluted with demineralized water (with a pH of around 7.5) to a volume of 150 ml. The thus obtained solution was spray-dried as described above with application of cylone II.

The aggregate content was investigated as described above.
  After 3 months' storage at 2-8° C. (3 months' stability), the solution prepared from the reconstituted powder had around 3.6% aggregates respectively.
  After 3 months' storage at 25° C. (3 months' stability), the solution prepared from the reconstituted powder had around 3.9% aggregates respectively.
  After 3 months' storage at 40° C. (3 months' stability), the solution prepared from the reconstituted powder had around 4.6% aggregates respectively.
The MMD of the powder was determined as described above. The MMD of the powder was 2.6 μm. The MMAD and FPF of the powder were determined as described above. The MMAD was 4.3 μm, and the FPF was 47.3% in relation to the powder capsule weight.

Spray Drying of a 2.833% (w/v) LS90P 0.33% (w/v) Isoleucine 0.166% (w/v) Calcitonin Formulation 4.250 g LS90P and 0.50 g isoleucine were dissolved in around 140 ml demineralized water (with a pH of around 7.5) in an ultrasonic bath. As the next step, 0.250 g calcitonin was added and diluted with demineralized water (with a pH of around 7.5) to a volume of 150 ml. The thus obtained solution was spray-dried as described above with application of cylone II.

The aggregate content was investigated as described above.
  After 3 months' storage at 2-8° C. (3 months' stability), the solution prepared from the reconstituted powder had around 3.3% aggregates respectively.
  After 3 months' storage at 25° C. (3 months' stability), the solution prepared from the reconstituted powder had around 3.6% aggregates respectively.
  After 3 months' storage at 40° C. (3 months' stability), the solution prepared from the reconstituted powder had around 3.6% aggregates respectively.
The MMD of the powder was determined as described above. The MMD of the powder was 2.8 μm. The MMAD and FPF of the powder were determined as described above. The MMAD was 4.4 μm, and the FPF was 49.2% in relation to the powder capsule weight.

Spray Drying of a 2.866% (w/v) LS90P 0.33% (w/v) Tri-isoleucine 0.166% (w/v) Calcitonin Formulation 4.250 g LS90P and 0.50 g tri-isoleucine were dissolved in around 140 ml demineralized water (with a pH of around 7.5) in an ultrasonic bath. As the next step, 0.250 g calcitonin was added and diluted with demineralized water (with a pH of around 7.5) to a volume of 150 ml. The thus obtained solution was spray-dried as described above with application of cylone II.

The aggregate content was investigated as described above.
  After 3 months' storage at 2-8° C. (3 months' stability), the solution prepared from the reconstituted powder had around 3.3% aggregates respectively.
  After 3 months' storage at 25° C. (3 months' stability), the solution prepared from the reconstituted powder had around 3.6% aggregates respectively.
  After 3 months' storage at 40° C. (3 months' stability), the solution prepared from the reconstituted powder had around 3.9% aggregates respectively.
The MMD of the powder was determined as described above. The MMD of the powder was 2.5 μm. The MMAD and FPF of the powder were determined as described above. The MMAD was 3.5 μm, and the FPF was 60.4% in relation to the powder capsule weight.

EXAMPLE 6

Freeze Drying of a 5% (w/v) IgG1 Formulation

Pure IgG1 with a concentration of around 109 mg/ml formulated in a pH 6 glycine-histidine buffer (see Materials) was diluted with demineralized water (with a pH of around 7.5) to a content of 50 mg/ml and freeze-dried in the absence of any other adjuvants. The solution had a volume of 50 ml and was distributed in commercial 2R vials before freeze drying. The lyophilisate was lyophilised in the 2R vials by means of a spatula and further treated as described above.

The aggregate content was investigated as described above.

After one week's open storage at 75% relative air humidity and 40° C. (forced storage stability), the solution prepared from the reconstituted powder had around 20.5% aggregates.

After one day's equilibration and four weeks' dry storage at 40° C., the solution prepared from the reconstituted powder had around 15.3% aggregates.

After one day's vacuum drying and four weeks' dry storage at 40° C., the solution prepared from the reconstituted powder had around 12.6% aggregates.

Freeze Drying of a 4.5% (w/v) Mannitol 0.5% (w/v) IgG1 Formulation 2.25 g mannitol were dissolved in around 40 ml demineralized water (with a pH of around 7.5). As the next step, 2.3 ml pure IgG1 with a concentration of around 109 mg/ml formulated in a pH 6 glycine-histidine buffer (see Materials) was diluted with demineralized water (with a pH of around 7.5) to a content of 50 mg/ml. The thus obtained solution contained around 4.5% (w/v) adjuvant or matrix and 0.5% (w/v) protein, was distributed in commercial 2R vials, and was freeze-dried as described above. The lyophilisate was lyophilised in the 2R vials by means of a spatula and further treated as described above. The aggregate content was investigated as described above.

The following aggregate contents were obtained for its storage stability:

After one week's open storage at 75% relative air humidity and 40° C. (forced storage stability), the solution prepared from the reconstituted powder had around 34.0% aggregates.

After one day's equilibration and four weeks' dry storage at 40° C., the solution prepared from the reconstituted powder had around 11.6% aggregates.

After one day's vacuum drying and four weeks' dry storage at 40° C., the solution prepared from the reconstituted powder had around 6.2% aggregates.

Freeze Drying of a 4.5% (w/v) LS55P 0.5% (w/v) IgG1 Formulation 2.25 g LS55P were dissolved in around 40 ml demineralized water (with a pH of around 7.5). As the next step, 2.3 ml pure IgG1 with a concentration of around 109 mg/ml formulated in a pH 6 glycine-histidine buffer (see Materials) was diluted with demineralized water (with a pH of around 7.5) to a content of 50 mg/ml. The thus obtained solution contained around 4.5% (w/v) adjuvant or matrix and 0.5% (w/v) protein, was distributed in commercial 2R vials, and was freeze-dried as described above. The lyophilisate was lyophilised in the 2R vials by means of a spatula and further treated as described above. The aggregate content was investigated as described above.

The following aggregate contents were obtained for its storage stability:

After one week's open storage at 75% relative air humidity and 40° C. (forced storage stability), the solution prepared from the reconstituted powder had around 2.5% aggregates.

After one day's equilibration and four weeks' dry storage at 40° C., the solution prepared from the reconstituted powder had around 2.6% aggregates.

After one day's vacuum drying and four weeks' dry storage at 40° C., the solution prepared from the reconstituted powder had around 1.2% aggregates.

Freeze Drying of a 4.5% (w/v) Coupling Sugar 0.5% (w/v) IgG1 Formulation 2.25 g Coupling Sugar were dissolved in around 40 ml demineralized water (with a pH of around 7.5). As the next step, 2.3 ml pure IgG1 with a concentration of around 109 mg/ml formulated in a pH 6 glycine-histidine buffer (see Materials) was diluted with demineralized water (with a pH of around 7.5) to a content of 50 mg/ml. The thus obtained solution contained around 4.5% (w/v) adjuvant or matrix and 0.5% (w/v) protein, was distributed in commercial 2R vials, and was freeze-dried as described above. The lyophilisate was lyophilised in the 2R vials by means of a spatula and further treated as described above. The aggregate content was investigated as described above.

The following aggregate contents were obtained for its storage stability:

After one week's open storage at 75% relative air humidity and 40° C. (forced storage stability), the solution prepared from the reconstituted powder had around 5.5% aggregates.

After one day's equilibration and four weeks' dry storage at 40° C., the solution prepared from the reconstituted powder had around 4.6% aggregates.

After one day's vacuum drying and four weeks' dry storage at 40° C., the solution prepared from the reconstituted powder had around 1.5% aggregates.

General Glossary for Figures:
TS Total solids
Isoleucin Isoleucine
Citrullin Citrulline
Tri-isoleucin Tri-isoleucine
Lysozym Lysozyme

The invention claimed is:

1. A powder comprising a pharmaceutically active substance and an excipient combination comprising at least two excipients, wherein at least one of the excipients is a tripeptide wherein the tripeptide is not identical to the pharmaceutical active substance, and wherein at least one of the excipients is a 1,4 O-linked saccharose derivative selected from the compounds:

1,4 O-linked D-Gal-saccharose (lactosucrose);
1,4 O-linked D-Glu-saccharose (glucosyl sucrose); and
1,4 O-linked Glu-Glu-saccharose (maltosyl sucrose), wherein the powder is a spray-dried powder.

2. The powder according to claim 1, wherein lactosucrose is the saccharose derivative.

3. The powder according to claim 2, wherein at least one excipient is a mono- or disaccharide.

4. The powder according to claim 3, wherein the lactosucrose content is at least 55% (w/w) of the sugar content in the powder.

5. The powder according to claim 1, wherein the powder comprises a mixture of glucosyl sucrose and maltosyl sucrose.

6. The powder according to claim 5, wherein the powder comprises one or more mono- or disaccharides.

7. The powder according to claim 6, wherein the total content of glucosyl sucrose and maltosyl sucrose is at least 25% (w/w) of the sugar content in the powder.

8. The powder according to claim 7, wherein the respective content of maltosyl sucrose and glucosyl sucrose is at least 18% (w/w) of the sugar content in the powder.

9. The powder according to claim 1 comprising at least one further excipient selected from an amino acid, another sugar, a sugar alcohol, a polymer and/or a pharmaceutically acceptable salt.

10. The powder according to claim 9, wherein the powder comprises at least one amino acid as an excipient.

11. The powder according to claim 10, wherein the amino acid is isoleucine.

12. The powder according to claim 1, wherein the tripeptide is tri-isoleucine.

13. The powder according to claim 11, wherein the dry mass of the powder comprises between 60 and 80% (w/w) of a 1,4 O-linked saccharose derivative or a sugar mixture which comprises at least one 1,4 O-linked saccharose derivative, and comprises between 1 and 19.99% (w/w) isoleucine.

14. The powder according to claim 1, wherein the dry mass of the powder comprises between 60 and 80% (w/w) of a 1,4 O-linked saccharose derivative or a sugar mixture which comprises at least one 1,4 O-linked saccharose derivative, and comprises between 1 and 19.99% (w/w) of a tripeptide.

15. The powder according to claim 14, wherein the tripeptide is tri-isoleucine.

16. The powder according to claim 15, wherein the content of the excipient combination is between 25 and 99.99% (w/w) of the dry mass of the powder.

17. The powder according to claim 16, wherein the content of pharmaceutical active substance is between 0.01 and 75% (w/w) of the dry mass of the powder.

18. The powder according to claim 17, wherein the pharmaceutical active substance is a biological macromolecule.

19. The powder according to claim 18, wherein the dry mass of the powder comprises between 60 and 90% (w/w) of a combination of excipients with at least one 1,4 O-linked saccharose derivative or a sugar mixture which comprises at least one 1,4 O-linked saccharose derivative, and comprises up to 40% (w/w) of a pharmaceutical active substance, and the content of lactosucrose, maltosyl sucrose and/or glucosyl sucrose is at least 20% (w/w) of the dry mass of the powder and the maximum sum of the weight percentages is 100% (w/w).

20. The powder according to claim 19, wherein the particles in the powder have a mass mean diameter (MMD) between 1 and 10 µm.

21. The powder according to one of claim 1 or 10, wherein the particles in the powder have a mass mean aerodynamic diameter (MMAD) between 1 and 5 µm.

22. A pharmaceutical formulation comprising a powder according to one of claim 1, 10 or 21.

23. A method of preparing a powder according to claim 1 comprising
   a) dissolving a pharmaceutical active substance in an aqueous solution/suspension;
   b) dissolving in an aqueous solution/suspension an excipient combination comprising at least two excipients, wherein at least one excipient is a 1,4 O-linked saccharose derivative selected from the compounds lactosucrose, glucosyl sucrose and maltosyl sucrose;
   c) mixing the active substance and the excipient combination if they are in different solutions/suspension; and
   d) spray-drying the solution/suspension comprising the excipient combination and the pharmaceutical active substance to a dry mass.

24. The method according to claim 23, wherein the pharmaceutical active substance is a biological macromolecule.

25. The method according to claim 24, wherein the 1,4 O-linked saccharose derivative is lactosucrose.

26. The method according to claim 25, wherein the solution or suspension contains lactose and saccharose as further excipients.

27. The method according to claim 26, wherein the content of lactosucrose is at least 55% (w/w) or the sugar content present in the solution or suspension.

28. The method according to claim 23, wherein the 1,4 O-linked saccharose derivative is a mixture of glucosyl sucrose and maltosyl sucrose.

29. The method according to claim 28, wherein the solution or suspension comprises one or more further mono- and/or disaccharides.

30. The method according to claim 29, wherein the total content of glucosyl sucrose and maltosyl sucrose is at least 25% (w/w) of the sugar content present in the solution or suspension.

31. The method according to claim 30, wherein the respective content of maltosyl sucrose and glucosyl sucrose is at least 18% (w/w) of the sugar content present in the solution or suspension.

32. The method according to claim 31, wherein the solution or suspension comprises one or more amino acids, peptides, further sugars, sugar alcohols, polymers and/or pharmaceutically acceptable salts.

33. The method according to claim 32, wherein the excipient combination contains an amino acid.

34. The method according to claim 33, wherein the amino acid is isoleucine.

35. The method according to claim 32, wherein the excipient combination contains a peptide, wherein the peptide is not identical to the pharmaceutical active substance.

36. The method according to claim 35, wherein the peptide is an isoleucine-containing peptide.

37. The method according to claim 35, wherein the peptide is a di- or tripeptide.

38. The method according to claim 37, wherein the tripeptide is a tri-isoleucine.

39. The method according to claim 34, wherein the dry mass is between 60 and 80% (w/w) of a 1,4 O-linked saccharose derivative or a sugar mixture which contains at least 1,4 O-linked saccharose derivative and between 1 to 19.99% (w/w) isoleucine, wherein the maximum sum of the weight percentages is 100% (w/w).

40. The method according to claim 38, wherein the dry mass is between 60 and 80% (w/w) of a 1,4 O-linked saccharose derivative or a sugar mixture which contains at least one 1,4 O-linked saccharose derivative and between 1 and 19.99% (w/w) of a tripeptide.

41. The method according to claim 40, wherein the content of excipient is between 25 and 99% (w/w) of the dry mass.

42. The method according to claim 41, wherein the content of pharmaceutical active substance is between 0.01 and 75% (w/w) of the dry mass, wherein the maximum sum of the weight percentages is 100%.

43. The powder according to claim 3, wherein at least one excipient is lactose or saccharose.

44. The powder according to claim 6, wherein the one or more mono- or disaccharides are selected from fructose, glucose and saccharose.

45. The method according to claim 29, wherein the one or more mono- and /or disaccharides are selected from fructose, saccharose and/or glucose.

* * * * *